United States Patent [19]

Mitsudera et al.

[11] Patent Number: 5,498,774

[45] Date of Patent: Mar. 12, 1996

[54] CONDENSED HETEROCYCLIC COMPOUNDS, THEIR PRODUCTION AND USE

[75] Inventors: Hiroyuki Mitsudera, Toyonaka; Masato Konobe; Yasuo Ishida, both of Suita; Kazuho Matsuura, Kyoto, all of Japan

[73] Assignee: Takeda Chemical Industries, Ltd.', Osaka, Japan

[21] Appl. No.: 140,984

[22] Filed: Oct. 25, 1993

Related U.S. Application Data

[63] Continuation of Ser. No. 542,076, Jun. 22, 1990, abandoned.

[30] Foreign Application Priority Data

| Jun. 23, 1989 | [JP] | Japan | 1-161507 |
| Oct. 27, 1989 | [JP] | Japan | 1-280358 |
| Apr. 27, 1990 | [JP] | Japan | 2-114318 |

[51] Int. Cl.$^6$ .................. C07D 471/08; A01N 43/48
[52] U.S. Cl. .................. 504/246; 546/121
[58] Field of Search .................. 546/121; 504/246

[56] References Cited

U.S. PATENT DOCUMENTS

| 4,159,375 | 6/1979 | Trust et al. | 544/184 |
| 4,405,619 | 9/1983 | Heilman et al. | 544/184 |
| 4,478,845 | 10/1984 | Whitney | 548/324 |
| 4,507,481 | 3/1985 | Davidson et al. | 546/121 |
| 4,517,182 | 5/1985 | Cheng | 544/179 |
| 4,743,586 | 5/1988 | Chan | 514/243 |
| 5,028,605 | 7/1991 | Sablayrdler et al. | 544/350 |
| 5,055,587 | 10/1991 | Mizukana | 548/262.4 |

FOREIGN PATENT DOCUMENTS

| 0059536 | 9/1982 | European Pat. Off. . |
| 0061836 | 10/1982 | European Pat. Off. . |
| 0076030 | 4/1983 | European Pat. Off. . |
| 0238070 | 9/1987 | European Pat. Off. . |
| 0252682 | 1/1988 | European Pat. Off. . |
| 60-139672 | 7/1985 | Japan . |
| 2145588 | 11/1988 | Japan . |
| 1400999 | 7/1975 | United Kingdom . |
| 2104522 | 3/1983 | United Kingdom . |
| 2190375 | 11/1987 | United Kingdom . |

OTHER PUBLICATIONS

Derwent Publications Ltd., Japanese Unexamined Publication No. 135,364/1988.
Sigova et al., Chemical Abstracts, 103(7):53910y (1985).
V.I. Sigova et al., "Synthesis and Biological Activity of the Aryl Amides of 2–methylnicotinic and 2 phenylindolisine–8–carboxylic acids" Chemical Abstracts, vol. 103, No. 7, Aug. 19, 1985.

*Primary Examiner*—C. Warren Ivy
*Assistant Examiner*—D. Margaret M. Mach
*Attorney, Agent, or Firm*—Foley & Lardner

[57] ABSTRACT

A condensed heterocyclic compound of the general formula:

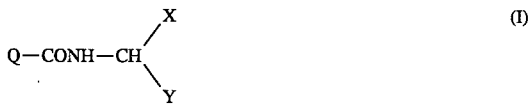

wherein Q is a condensed heterocyclic group having a nitrogen atom in the bridgehead which is unsubstituted or substituted, X is a hydrogen atom or a group attached through C, O, S or N, and Y is an electron attractive group, or its salt which is useful as agricultural chemical.

7 Claims, No Drawings

CONDENSED HETEROCYCLIC COMPOUNDS, THEIR PRODUCTION AND USE

This application is a continuation of U.S. application Ser. No. 07/542,076 filed Jun. 22, 1990, now abandoned.

BACKGROUND OF THE INVENTION

1. Field of the Invention

This invention relates to novel condensed heterocyclic compounds or salts thereof, intermediates thereof, method for preparing them and farming and gardening fungicides containing them.

2. Description of the Prior Art

It has been known that some kinds of amide compounds possess fungicidal activity against pathogenic fungi causing various kinds of plant blight. For instance, compounds described in Japanese Patent Unexamined Publication No. 135,364/1988, EP 61836A and GB 2190375A exhibit effects against downy mildew fungi of a vine and cucumber and pathogenic fungi of a tomato and potato. However, it is hard to say that those compounds exhibit sufficient controlling effects and safety.

Thus, it is desired to conquer the aforementioned defects, namely, to provide compounds possessing excellent control effects against plant blight, method for preparing those compounds and agent for controlling plant blight containing those compounds.

Downy mildew and other blight of vegetables and fruit trees are liable to happen and spread in a time of much rain. Accordingly, it is required to provide compounds which are not washed away by rain (rain-resisting quality) and exhibit excellent effect for controlling and curing plant blight, do not damage the cultivating plants and show less toxicity to warm-blooded animals and fish, and also to provide a simple and easy method for preparing those compounds in high yield and to provide a useful agricultural chemical containing those compounds.

SUMMARY OF THE INVENTION

The present inventors have studied intensively to attain the aforementioned problems, and succeeded in preparation of condensed heterocyclic compounds of the following general formula (I) and their salts and found that these compounds exhibit excellent effects for controlling various kinds of plant blight, especially downy mildew and blight, possess excellent rain-resisting quality, do not damage the plants and are less toxicity against warm-blooded animals and fish and that those compounds can be prepared by an industrially advantageous method.

Thus, the present invention relates to a condensed heterocyclic compound of the general formula:

(I)

wherein Q is a condensed heterocyclic group having a nitrogen atom in the bridgehead which is unsubstituted or substituted, X is a hydrogen atom or a group attached through C, O, S or N, and Y is an electron attractive group, and its salt.

This invention also relates to a method for preparing a condensed heterocyclic compound (I) or its salt by reacting a compound of the general formula:

(II)

wherein Q has the same meaning as defined in the above formula (I), and Z is a leaving group, or its salt with a compound of the general formula:

(III)

wherein X and Y are each as defined in the above formula (I), or its salt.

And further, this invention relates to a farming and gardening fungicide containing a condensed heterocyclic compound of the general formula (I) or its salt.

According to one aspect, the present invention provides a condensed heterocyclic carboxylic acid compound of the general formula:

(IV)

wherein $Q^1$ is a condensed heterocyclic group having a nitrogen atom in the bridgehead as follows

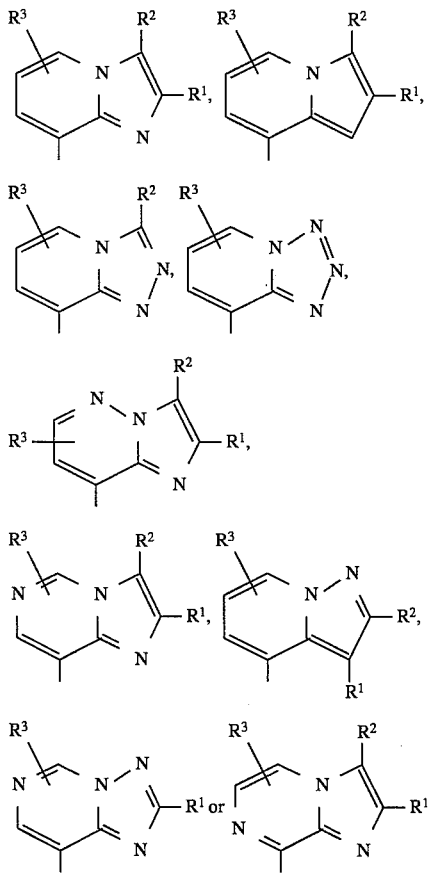

in which $R^1$ is an $C_{1-6}$ alkyl, halogen, $C_{1-4}$ alkoxy, $C_{1-4}$ alkylthio, $C_{6-10}$ aryloxy, $C_{6-10}$ arylthio, alkoxycarbonyl, phenyl, substituted phenyl or aromatic heterocyclic group; $R^2$ and $R^3$ are a hydrogen, $C_{1-6}$ alkyl, halogen, nitro, amino, sulfo, mono- or di-alkylsulfamoyl, alkoxycarbonyl, formyl, cyano, phenyl, substituted phenyl or aromatic heterocyclic group, provided that when $Q^1$ is

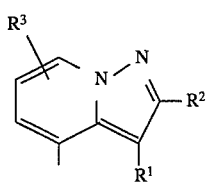

and $R^1$ is $COOCH_2CH_3$, either one of $R^2$ and $R^3$ is another group than hydrogen atom, and Z is a leaving group; or its salt.

According to another aspect, the present invention provides a process for preparing a compound of the general formula:

$$Q^2—CO—Z \quad (VIII)$$

wherein $Q^2$ is a group of the general formula:

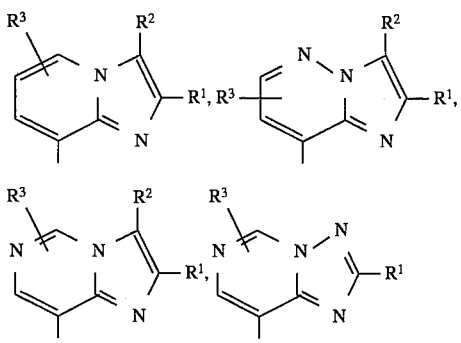

in which $R^1$, $R^2$ and $R^3$ have the same meanings as defined above or its salt which comprises reacting a compound of the general formula:

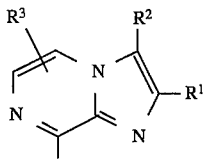

wherein the ring Ⓐ is a pyridine, pyridazine, pyrimidine or pyrazine group which is unsubstituted or substituted by an $C_{1-6}$ alkyl, halogen, nitro, amino, sulfo, mono- or di-alkyl-sulfamoyl alkoxycarbonyl, formyl, cyano, phenyl, substituted phenyl or aromatic heterocyclic group, and Z is a leaving group, or its salt with a compound of the general formula:

$$\begin{array}{c} R^2 \\ | \\ W—CH—CO—R^1 \end{array} \quad (VI)$$

or $$\begin{array}{c} R^1 \\ | \\ W—CH—NHOH \end{array} \quad (VII)$$

wherein W is a halogen atom, and $R^1$ and $R^2$ have the same meanings as defined above.

The compounds (I) or their salts of this invention have a novel structure characterized by the combination of a specific group, namely, a condensed heterocyclic group having at least one nitrogen atom in the bridgehead and the carbonyl group, which is different form the known amide compounds. The compounds of this invention have merits that they exhibit an excellent control effect for downy mildew and blight, possess excellent water-resisting quality, do not damage the plants and are less toxycity against warm-blooded animals and fish.

PREFERRED EMBODIMENT OF THE INVENTION

In the above formula (I) and (II), the symbol Q means a condensed heterocyclic group having a nitrogen atom in the bridgehead which is unsubstituted or substituted. The condensed heterocyclic group having a nitrogen atom in the bridgehead means a condensed heterocyclic group where the atom(s) of the head or end of the bridge bond, namely, both of them or either of them is a nitrogen atom, which is not ionized. The condensed heterocyclic group having a nitrogen atom in the bridgehead represented by the Q is a group which is formed by removing one hydrogen atom bonded to a ring-constituting carbon atom at a position other than the bridgehead of a condensed heterocyclic compound shown, for example, by the general formula:

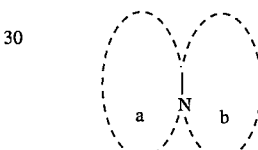

or

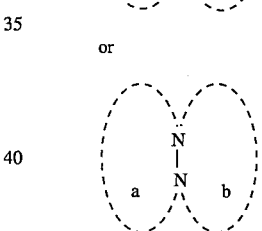

wherein the rings a and b are each a N-containing heterocyclic ring which is unsubstituted or substituted.

Those condensed heterocyclic groups can be represented, for example, by the general formula:

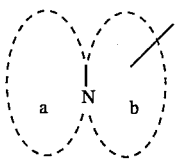

or

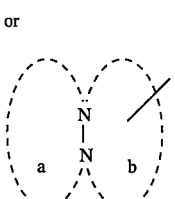

wherein—means a chemical bond, and the other symbols are each as defined above. The preferred one is a group shown by the above left formula.

The N-containing heterocyclic ring represented by the ring a and ring b means a 4 to 8-membered, preferably 5 to 6-membered heterocyclic ring containing 1 to 4 nitrogen atom(s), which may further contain 1 to 3 oxygen atom(s) and/or 1 to 3 sulfur atom(s) optionally mono- or di-oxidized. Such heterocyclic ring may further be condensed with a 5 to 6 membered aliphatic cycle (e.g. cyclopentane, cyclohexane), aromatic cycle (e.g. benzene or naphthalene) or heterocycle (preferably 5 to 6-membered heterocycle).

Among these condensed heterocyclic rings, heterocyclic groups formed by condensation of a 5-membered ring and 6-membered ring are preferable.

In the above formula, the ring a is preferably a 5-membered heterocycle containing 1 to 3 nitrogen atoms, and the ring b is preferably a 6-membered heterocycle containing 1 to 2 nitrogen atoms or a 5-membered heterocycle containing 1 to 2 nitrogen atoms and 1 sulfur atom optionally mono- or di-oxidized.

The rings a and b may be substituted by the same or different one to three substituents ($B^1$, $B^2$, $B^3$) as defined below.

Specifically, the group represented by the general formula:

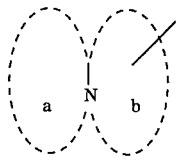

includes the groups shown, for example, by the general formulae:

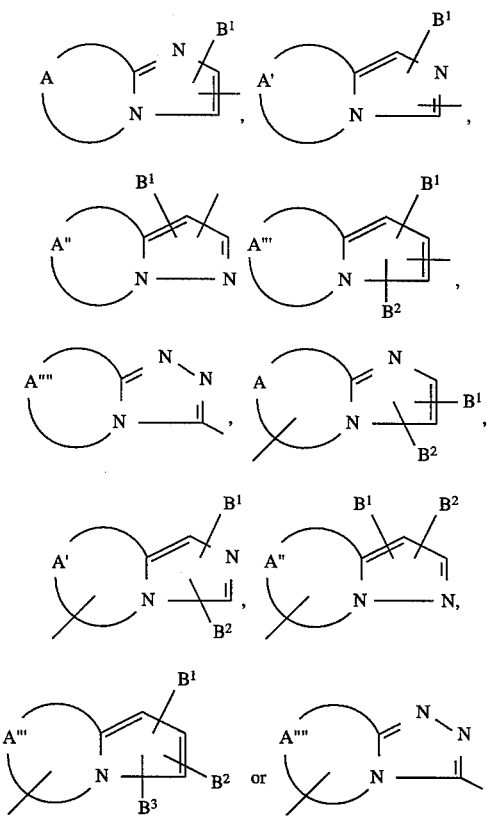

wherein A is a group forming a condensed ring at the [1,2] positions of the imidazole ring, A' is a group forming a condensed ring at the [1,5] positions of the imidazole ring, A'' is a group forming a condensed ring at the [1,5] positions of the pyrazole ring, A''' is a group forming a condensed ring at the [1,2]positions of the pyrrole ring, A'''' is a group forming a condensed ring at the [3,4] positions of the triazole ring, and $B^1$, $B^2$ and $B^3$ are each as defined below The group A, A', A'', A''' or A'''' contains 1 to 4, preferably 3 to 4 carbon atoms as the ring-constituting atom and may further contain 1 to 3 of nitrogen, oxygen and/or sulfur atom(s) (which may be in mono- or di-oxidized form).

Among the above condensed heterocyclic groups, the groups represented by the general formulas:

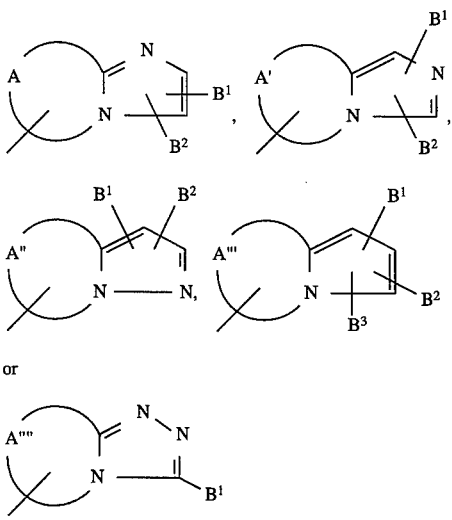

or

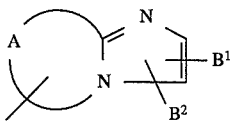

are preferable.

The group represented by the general formula:

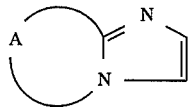

is more preferable.

Examples of the condensed rings represented by

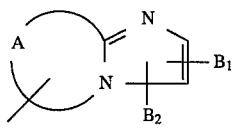

as the skeleton of the group of the general formula

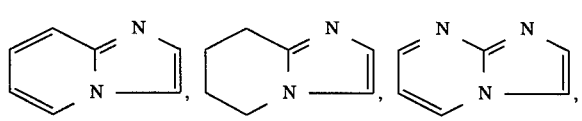

include:

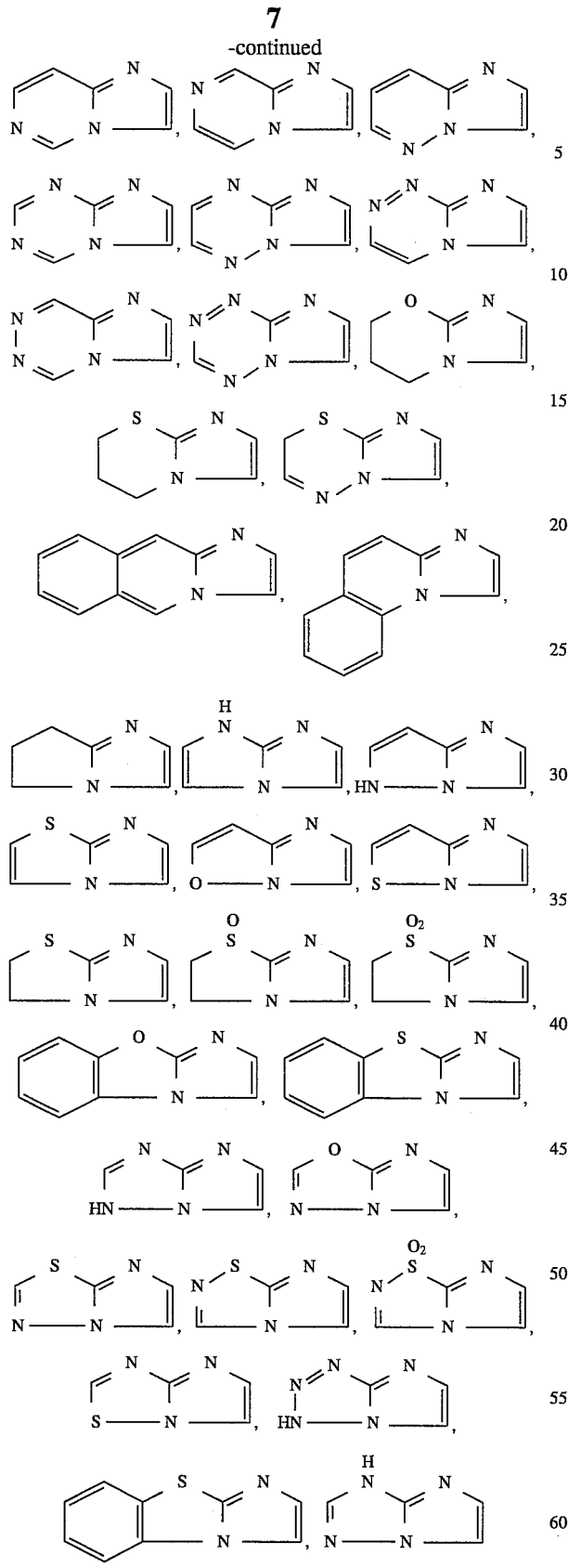
and
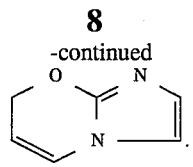
Examples of the condensed rings represented by
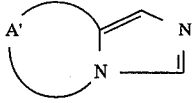
as the skeleton of the group of the general formula:
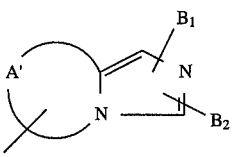
are:
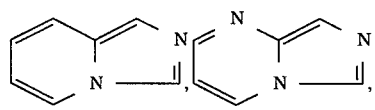
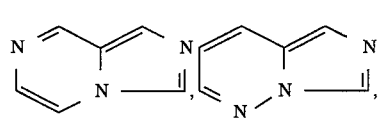
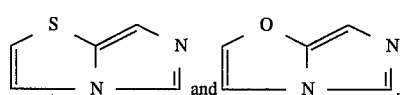
Examples of the condensed rings represented by
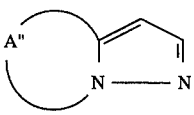
as the skeleton of the group of the general formula:
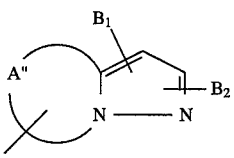
are:
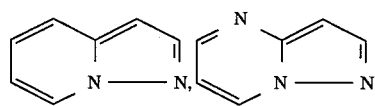
and
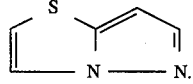
Examples of the condensed rings represented by

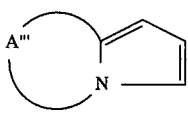

as the skeleton of the group of the general formula:

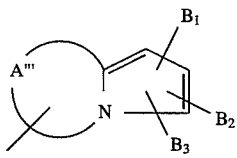

are:

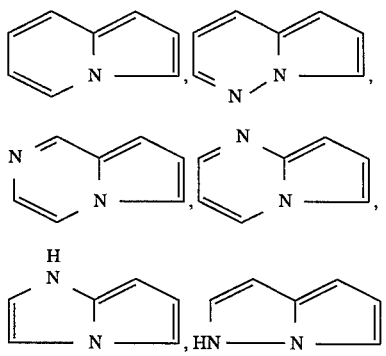

and

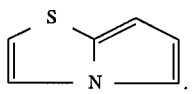

Examples of the condensed rings represented by

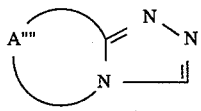

as the skeleton of the group of the general formula:

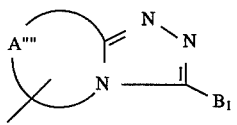

are:

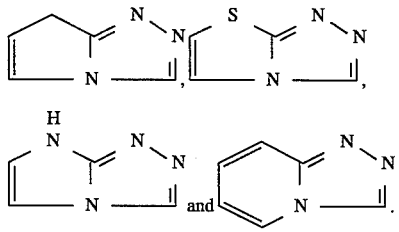

More specifically, these condensed heterocyclic groups include imidazo[1,2-a]pyridine, imidazo[1,2-a]pyrimidine, imidazo[1,2-c]pyrimidine, imidazo[1,2-a]pyrazine, imidazo[1,2-b]pyridazine, imidazo[1,2-b](1,2,4)-triazine, imidazo[2,1-a]imidazole, imidazo[1,2-b]pyrazole, imidazo[2,1-b]thiazole, imidazo[2,1-b](1,3,4)thiazole, 2,3-dihydroimidazo[2,1-b]thiazole, pyrazolo[1,5-a]pyrimidine, pyrazolo[5,1-a]thiazole, pyrazolo[1,5-a]pyridine, pyrrolo[1,3-b]pyridine, imidazo[1,5-a]pyridine and (1,2,4)triazolo[3,4-b]thiazole.

On the other hand, the group represented by the general formula:

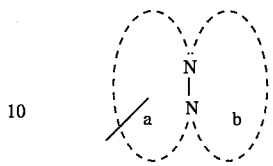

includes the groups represented, for example, by the general formulae:

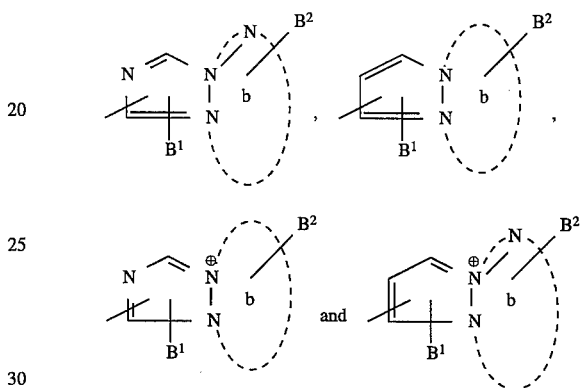

wherein $B^1$ and $B^2$ are each as defined below.

More specifically, 6H-(1,2,4)triazolo[ 1,2-b](1,2,3,4)tetrazyl, 1H-[1,2,4]triazolo[ 1,2-a](1,2,4)triazyl, (1,2,3)triazolo[2,1-a](1,2,3)triazin-4-ium, (1,2,4)triazolo[1,2-a]pyridazin-4-ium and 6H-pyrazolo[1,2-a](1,2,4,5)tetrazyl are exemplified.

The substituents $B^1$, $B^2$ and $B^3$ on the condensed heterocyclic group for Q may be the same or different each other. Examples of the substituents are hydrogen atom, nitro, amino, hydroxyl, cyano, $C_{1-3}$ acyl (formyl, etc. ), carbamoyl, carboxyl, alkoxycarbonyl (e.g., $C_{1-4}$ alkoxycarbonyl such as methoxycarbonyl, ethoxycarbonyl, n-propoxycarbonyl, isopropoxycarbonyl, etc.), sulfo, halogen (chlorine, bromine, iodine, fluorine, etc.), $C_{1-4}$ alkoxy (methoxy, ethoxy, propoxy, isopropoxy, butoxy, isobutoxy, sec-butoxy, tert-butoxy, etc.), $C_{6-10}$ aryloxy (phenoxy, etc.), $C_{6-10}$ arylcarbonyl (benzoyl, etc.), $C_{6-10}$ aryl (phenyl, etc.), $C_{7-10}$ aralkyl (benzyl, phenethyl, etc.), $C_{3-7}$ cycloalkyl (cyclohexyl, etc.), $C_{1-4}$ alkylthio (methylthio, ethylthio, propylthio, isopropylthio, butylthio, iso-butylthio, sec-butylthio, tertbutylthio, etc.), $C_{6-10}$ arylthio (phenylthio, etc.), $C_{7-10}$ aralkylthio (benzylthio, etc.), mono- or di-alkylsulfamoyl (e.g., mono- or di-$C_{1-4}$ alkylsulfamoyl such as mono- or di-methylsulfamoyl, mono- or di-ethylsulfamoyl, mono- or di-n-propylsulfamoyl), $C_{1-6}$ alkyl (methyl, ethyl, propyl, isopropyl, pentyl, hexyl, etc.), substituted phenyl(mono-, di-, tri or tetra-halogen-substituted phenyl such as 2-chlorophenyl, 3-chlorophenyl, 4-chlorophenyl, 2-fluorophenyl, 4-bromophenyl, 2,3-dichlorophenyl, 2,4-dichlorophenyl, 2,6-dichlorophenyl, 2,4-difluorophenyl, 2,6-difluorophenyl, etc., mono, di-, tri or tetra-$C_{1-4}$ alkyl-substituted phenyl such as 2-methylphenyl, 3-methylphenyl, 4-ethylphenyl, 4-isopropylphenyl, 2,4- dimethylphenyl, 2,5-dimethylphenyl, 3,4-dimethylphenyl, 2,5-diethylphenyl, 2,4,6-trimethylphenyl, etc., mono-, di-, tri or tetra-$C_{1-4}$ alkoxy-substituted phenyl such as 2-methoxyphenyl, 3-methoxyphenyl, 4-methoxyphenyl, 3,4-dimethoxyphenyl, etc., mono-, di-, tri or tetra-$C_{1-4}$ alkylthio-substituted phenyl such as 2-methylthiophenyl, 3,4-dimethylthiophenyl, etc., 2-chloro-4-nitrophenyl, 4-nitrophenyl, 2-methyl-4-aminophenyl, 2-bromo-4-nitrophenyl, 2-nitro-4-methylphenyl, etc.), aromatic heterocyclic group (5 or 6 membered heterocyclic group such as pyridyl, furyl, thienyl, thiazolyl, etc.). Especially, one of $B^1$, $B^2$ and $B^3$ is preferably $C_{1-6}$ alkyl, phenyl or substituted phenyl.

$Q^1$ in the above mentioned general formula {IV} means a condensed heterocyclic group having a nitrogen atom in the bridgehead shown by the following formula:

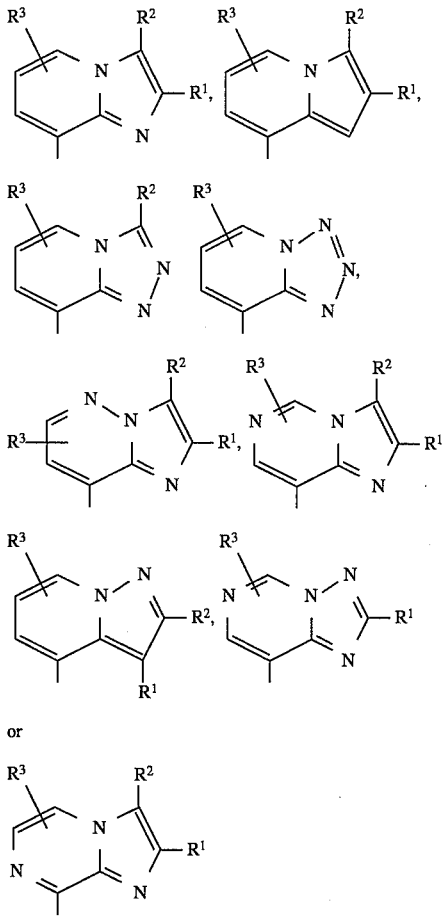

The substituents $R^1$ $R^s$ and $R^3$ are the same or different and have the same meanings as mentioned above but either one of $R^2$ and $R^3$ is a group other than hydrogen atom when $Q^1$ is

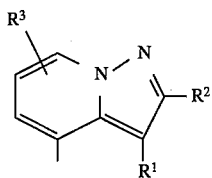

and $R^1$ is $COOCH_2CH_3$.

Examples of the substituent $R^1$ include the $C_{1-6}$ alkyl, halogen, $C_{1-4}$ alkoxy, $C_{1-4}$ alkylthio, $C_{6-10}$ aryloxy, $C_{6-10}$ arylthio, alkoxycarbonyl, phenyl, substituted phenyl or aromatic heterocyclic group as stated in the above $B^1$, $B^2$ and $B^3$ Examples of the substitutents $R^2$ and $R^3$ include hydrogen, nitro, amino, sulfo, formyl, cyano or phenyl group, and also the $C_{1-6}$ alkyl, halogen, mono- or di-alkylsulfamoyl, alkoxycarbonyl, substituted phenyl or aromatic heterocyclic groups as stated in the above $B^1$, $B^2$ and $B^3$ The substituent $R^1$ is preferably phenyl or a substituted phenyl.

Preferable ones of $Q^1$ are $Q'$ or $Q''$ as described below.

The symbol X in the general formula (I) is a hydrogen atom or a group attached through C, O, S or N atom. The group attached through a C atom may be an alkyl, alkenyl, haloalkyl, cycloalkyl, cycloalkenyl, aryl or aralkyl group or an aromatic heterocyclic group having a chemical bond at a carbon atom; the group attached through an O atom may be an alkoxy, aryloxy or aralkyloxy group; the group attached through a S atom may be an alkylthio, arylthio or aralkylthio group; and the group attached through a N atom may be an alkylamino, arylamino or aralkylamino group or an aromatic heterocyclic group having a chemical bond at a N atom.

The above alkyl group and alkyl moiety of the haloalkyl, alkoxy, alkylthio and alkylamino groups include a straight or branched one containing 1 to 10 carbon atoms such as methyl, ethyl, propyl, isopropyl, n-butyl, isobutyl, sec-butyl, tert-butyl, n-pentyl, sec-pentyl, isopentyl, neopentyl, n-hexyl, isohexyl, n-octyl, n-decyl and the like.

The above alkenyl group may be one containing 2 to 4 carbon atoms such as vinyl, allyl, 2-methalyl, 3-methalyl, 3-butenyl or the like.

The above cycloalkyl group may be a 3- to 6-membered one such as cyclopropyl, cyclopentyl, cyclohexyl or the like.

The above cycloalkenyl group may be a 3- to 6-membered one such as cyclopropenyl, cyclopentenyl, cyclohexenyl or the like.

The above aryl group and aryl moiety of the aryloxy, arylthio and arylamino groups may be one containing 6 to 10 carbon atoms such as phenyl, tolyl, xylyl, naphthyl or the like.

The above aralkyl group and aralkyl moiety of the aralkyloxy, aralkylthio and aralkylamino groups may be one containing 7–10 carbon atoms such as benzyl, phenethyl or the like.

The aromatic heterocyclic group having a chemical bond at a C atom may be a 5 or 6-membered aromatic heterocyclic one such as

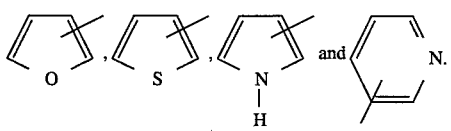

The aromatic heterocyclic group having a chemical bond at a N atom may be a 5 or 6-membered N-containing one such as

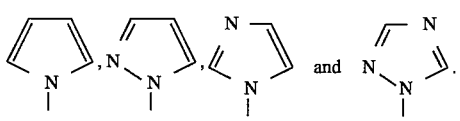

Each of the above mentioned groups attached through C, O, S or N atom may further have one to four substituents such as nitro, amino, hydroxyl, cyano, carboxyl, sulfo, a halogen (fluorine, chlorine, bromine, etc.), an alkoxy containing 1 to 4 carbon atoms (methoxy, ethoxy, etc.), an alkylthio containing 1 to 4 carbon atom(s) (methylthio, ethylthio, etc.), phenylthio, benzylthio and the like.

Suitable examples of X include hydrogen atom, an $C_{1-10}$ alkyl, $C_{2-4}$ alkenyl, $C_{1-10}$ alkoxy, $C_{1-10}$ alkylthio, phenyl, halogen-substituted phenyl, aromatic heterocyclic group having a chemical bond at C or N atom or the like. Specific examples of these groups include the ones exemplified for $B^1$, $B^2$ and $B^3$ in the above.

The symbol Y in the general formula (I) means an electron attractive group, such as cyano, carbamoyl, thiocarbamoyl or trichloromethyl group or the like. Cyano group is preferable as an example of Y.

Especially interesting compounds of this invention are ones represented by the following formula (I'):

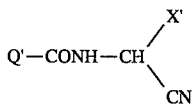  (I')

wherein Q' is a group of the formula:

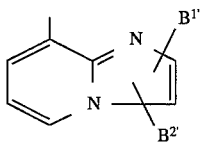

(one of $B^{1'}$ and $B^{2'}$ is an $C_{1-6}$ alkyl, phenyl or substituted phenyl group and the other is a hydrogen atom), X' is a phenyl, halogen-substituted phenyl or aromatic heterocyclic group having a chemical bond at a C atom.

Another group of interesting compounds (I) is one represented by the following formula (I"):

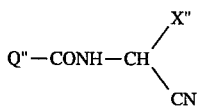  (I")

wherein Q" is

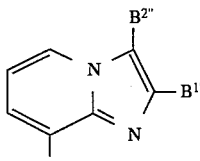

($B^{1'''}$ is a phenyl or substituted phenyl group, $B^{2''}$ is a hydrogen atom or a $C_{1-6}$ alkyl group), and X" is a phenyl, fluorine-substituted phenyl, thienyl or furyl group.

The $C_{1-6}$ alkyl group and substituted phenyl group exemplified in the above $B^1$, $B^2$ and $B^3$ are applicable to those in $B^{1'}$, $B^{1'''}$, $B^{2'}$ and $B^{2''}$ of the formulas (I') and (I"). The halogen-substituted phenyl group for X' may be a phenyl group substituted by one to four halogens of fluorine, chlorine, bromine and so on. The fluorine-substituted phenyl group for X" may be o-, m- or p-fluorophenyl, o,m- or o,p-difluorophenyl or 2,4,6-trifluorophenyl. The aromatic heterocyclic groups having a chemical bond at C atom mentioned in the symbol X are applicable to those of X'.

Preferable example of the symbols Q' and Q" is

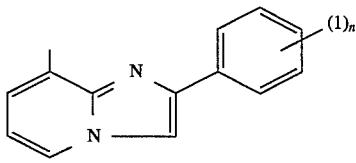

wherein n is 0, 1, 2, 3 or 4 and l is the same or different a $C_{1-4}$ alkyl, $C_{1-4}$ alkoxy, $C_{1-4}$ alkylthio or halogen. The substituted phenyl groups mentioned in $B^1$ $B^2$ and $B^3$ are applicable to the group:

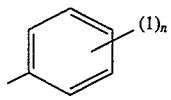

(n≠0). X' and X" is preferably 2-thienyl group, etc.

The compounds(I) of this invention contain an asymmetric carbon atom, and this invention include each isomer due to the asymmetric carbon atom and a mixture thereof.

The salt of the compounds (I) of this invention may be a salt formed by an alkali metal or alkaline earth metal such as sodium, magnesium, potassium, calcium, etc. with an acidic group (e.g., carboxy, etc.) contained as a substituent, or a salt formed by a mineral acid such as hydrochloric acid, phosphoric acid, sulfuric acid, etc. or an organic acid such as oxalic acid, acetic acid, benzoic acid, etc. with a basic group contained in the substituent(s) or condensed heterocycle.

The carboxylic acids (II) and (IV) having condensed heterocycle, which are used as the starting materials in this invention, or their salts can be prepared by a method similar to the known methods described in, for example, J. Org. Chem., Vol. 37, page 3107 (1972); J. Org. Chem., Vol. 36, page 2678 (1971); J. Org. Chem., Vol. 42, page 4197 (1977); J. Med. Chem., Vol. 17, page 645 (1974); J. Med. Chem., Vol. 20, page 386 (1977); J. Med. Chem., Vol. 15, page 982 (1972); J. Med. Chem., Vol. 28, page 876 (1985); Tetrahedron Lett., Vol. 21, page 2195 (1980); J. Chem., Soc., Perkin Trans. I. page 1159 (1987), and the like.

In more detail, some of the carboxylic acids (II) or (IV) or their salts can be prepared, for example, by reacting an aromatic heterocyclic aminocarboxylic acid, its reactive derivative or salt with a compound of the formula (VI) or (VII).

Especially, a compound (VIII) or its salt which is frequently used among novel compounds (IV) or their salts can be prepared by reacting a compound (V) or its salt with a compound (VI) or a compound (VII).

In the formulas (II), (IV), (V) and (VIII), Z denotes a leaving group and accordingly —COZ can denote —COOH or its reactive derivate. Thus, the compound (II) or its salt can be represented by a carboxylic acid of the formula:

  (II')

wherein Q has the same meaning as defined above, or its reactive derivative, or its salt; the compound (IV) or its salt be represented by a carboxylic acid of the formula:

  (IV')

wherein Q' has the same meaning as defined above, or its reactive derivative, or its salt; the compound (V) or its salt be represented by a carboxylic acid of the formula:

  (V')

wherein the ring Ⓐ has the same meaning as defined above or its reactive derivative, or its salt; the compound (VIII) or its salt be represented by a carboxylic acid of the formula:

  (VIII')

wherein $Q^2$ has the same meaning as defined above, or its reactive derivative, or its salt, respectively.

Examples of the reactive derivatives at the carboxyl group in the aromatic heterocyclic amino carboxylic acid and carboxylic acids (II'), (IV'), (V') and (VIII') include the acid anhydrides, active amides, active esters or the like. Specific examples of such reactive derivatives are as follows:

1) Acid anhydrides may be mixed anhydrides with halogenic acids (e.g., hydrochloric acid or hydrobromic acid), mono-alkyl carbonates, aliphatic carboxylic acids (e.g., acetic acid, pivaloic acid, valeric acid, isovaleric acid or trichloroacetic acid) or aromatic carboxylic acids (e.g., benzoic acid), or symmetric acid anhydrides.
2) Active amides may be amides with pyrazole, imidazole, 4-substituted imidazole, dimethylpyrazole or benztriazole.
3) Active esters may be methyl ester, ethyl ester, methoxymethyl ester, propargyl ester, 4-nitrophenyl ester, 2,4-dinitrophenyl ester, trichlorophenyl ester, pentachlorophenylester or mesylphenyl ester, or other esters with 1-hydroxy-1H-2-pyrrolidone, N-hydroxysuccinimide or N- hydroxyphthalimide.

Such reactive derivatives at carboxyl group are suitably selected and used depending upon the kind of the used carboxylic acids.

Further, the above mentioned aromatic heterocyclic amino carboxylic acid and carboxylic acids (II'), (IV'), (V') and (VIII') may be used in their free form (i.e., carboxylic acid form), preferably in the presence of a condensing agent such as N,N'-dicyclohexylcarbodiimide, N-cyclohexyl-N'-morpholinoethylcarbodiimide, N-cyclohexyl-N'-(4-diethylaminocyclohexyl)carbodiimide or N-ethyl-N'-(3-dimethylaminopropyl)carbodiimide. In addition, the above carboxylic acids may be used as the salts with an alkali metal or alkaline earth metal.

The symbol W in the formula (VI) and (VII) denotes a halogen atom such as chlorine, bromine or fluorine. The ring Ⓐ in the formula (V) may be pyridine, pyridazine, pyrimidine or pyrazine ring, which may be substituted by a group as mentioned in $R^3$, $Q^2$ is preferably Q' or Q".

This reaction can be carried out without solvent or in a suitable solvent and in the presence of a condensing agent such as a base, if necessary. The suitable solvents may be, alcohols such as ethanol, isopropyl alcohol, etc., aromatic hydrocarbons such as benzene, toluene, xylene, etc., halogenated hydrocarbons such as methylene chloride, chloroform, carbon tetrachloride, etc., ethers such as diethyl ether, dioxane, tetrahydrofuran, dimethoxyethane, etc., ketones such as acetone, methyl ethyl ketone, etc., nitriles such as acetonitrile, propionitrile, etc., amides such as dimethylformamide, dimethylacetamide, etc., esters such as methyl acetate, ethyl acetate, butyl acetate, etc., or a mixture thereof. If necessary, a mixed solvent of water and an aromatic hydrocarbon or halogenated hydrocarbon may be used. The solvent is usually used in ratios of 1 to 50 times (weight), preferably 5 to 10 times, to the carboxylic acids or their reactive derivatives or salts. The reaction may be accelerated by adding a base to the solvent. Suitable base may be, tertiary amines such as triethylamine, pyridine, 4-dimethylaminopyridine, DBU (1,8-diazabicyclo[5,4,0]-undec-7-ene), etc., alkali metal or alkaline earth metal hydroxide, carbonate or bicarbonate or alkali metal alcoholate such as sodium carbonate, potassium carbonate, sodium bicarbonate, sodium hydroxide, potassium hydroxide, sodium alcoholate, etc., or organic metal salt such as n-butyl lithium, etc. The base is usually used in i to 5 equivalents, preferably, 1 to 3 equivalents, to the carboxylic acids or their reactive derivatives or salts.

The compound of the formula (VI) or (VII) is used in an amount of 1.1 to 2.0 moles, to 1 mole of the carboxylic acid or its reactive derivative or salt in this reaction. This reaction may be carried out at room temperature (e.g., −10° C. to 30° C.) or at an elevated temperature (e.g., 30° to 100° C.) for accelerating the reaction. The reaction time depends on the reaction temperature, etc., and it is usually 15 minutes to 24 hours, preferably 30 minutes to 10 hours.

Thus, the resulting compound (II) or (IV) can be isolated and purified as a free base by a known method such as chromatography on silica gel (Kiesel gel®60 manufactured by Merck & Co., Inc., eluting solvent: chloroform, ethyl acetate, etc.), or isolated and purified as an acid addition salt with an inorganic acid such as hydrochloric acid, sulfuric acid, phosphoric acid, etc., or with an organic acid such as acetic acid, benzenesulfonic acid, p-toluenesulfonic acid, methanesulfonic acid, citric acid, tartaric acid, oxalic acid, propionic acid, maleic acid, malic acid, malonic acid, fumaric acid, mandelic acid, ascorbic acid, etc. according to a conventional method by conventional means such as concentration, concentration under reduced pressure, extraction, phase transfer, crystallization, recrystallization or chromatography. In case where a carboxy group or the like is contained as a substituent in the compound, said compound can be converted to a salt with alkali metal or alkaline earth metal as exemplified before according to a conventional method, which can be further isolated and purified by conventional means as mentioned above.

The condensed heterocyclic carboxylic acid derivative (II) or (IV) or its salt prepared by the above reaction can also converted to a nitro-substituted compound by a conventional nitration, or to a halogenated compound by using a halogenating agent such as N-bromosuccinimide (NBS), N-chlorosuccinimide (NCS), or the like.

The amines (III) and their salts (salts with the acids as mentioned in the above compounds (II) and (IV)) can be prepared by a known method or method similar thereto.

A compound (I) or its salt can be prepared by reacting a compound (II) or its salt with a compound (III) or its salt.

In more detail, a compound (I) or its salt can usually be prepared by reacting a compound (II) or its salt with a compound (III) or its salt without solvent or in a suitable solvent and in the presence of a suitable base or condensing agent. The suitable solvents may be, aromatic hydrocarbons such as benzene, toluene, xylene, etc., hologenated hydrocarbons such as methylene chloride, chloroform, carbon tetrachloride, etc., ethers such as diethyl ether, dioxane, tetrahydrofuran, etc., ketones such as acetone, methyl ethyl ketone, etc., nitriles such as acetonitrile, propionitrile, etc., amides such as dimethylformamide, dimethylacetamide, etc., esters such as methyl acetate, ethyl acetate, butyl acetate, etc., or a mixture thereof. If necessary, a mixture of water and an aromatic hydrocarbon or halogenated hydrocarbon may be used. The solvent is usually used in 1 to 50 times (weight), preferably 5 to 10 times, to the compound (II) or its salt. The reaction can be accelerated by adding a base to the solvent. The suitable bases may be, tertiary amines such as tri- ethylamine, pyridine, 4-dimethylaminopyridine, DBU (1,8-diazabicyclo[5,4,0]undec- 7-ene), etc., alkali metal or alkaline earth metal hydroxides, carbonates or bicarbonates or alkali metal alcoholates such as sodium carbonate, potassium carbonate, sodium bicarbonate, sodium hydroxide, potassium hydroxide, sodium alcoholate, etc., or organic metal salt such as n-butyl lithium, etc. Such base is usually used in 1 to 20 equivalents, preferably 2 to 5 equivalents, to the compound (II) or its salt. The suitable condensing agents may be, thionyl chloride, phosphorus oxy- chloride, carbonyldiimidazole, N-methyl-2-bromo-pyridinium iodide, dicyclohexylimide, etc., or a mixture thereof. Such condensing agent is usually used in 1 to 10 equivalents, preferably 2 to 5 equivalents, to the compound (II) or its salt.

In the reaction, the compound (II) or its salt is used in an amount of 1.1 to 1.5 moles to 1 mole of the compound (III) or its salt. The reaction may be carried out under cooling or at up to room temperature (−20° to 30° C.), or at an elevated temperature such as about 30° to 100° C. to accelerate the reaction. Though the reaction time depends on the reaction temperature, etc., it is usually 15 minutes to 15 hours, preferably about 30 minutes to 8 hours.

Thus the resulting compound (I) can be isolated and purified as a free base by a known method such as chromatography on silica gel (Kiesel gel 60 manufactured by Merck & Co, Inc., eluting solvent:chloroform, ethyl acetate etc.), or isolated and purified as an acid addition salt with an inorganic acid such as hydrochloric acid, sulfuric acid, phosphoric acid, etc., or with an organic acid such as acetic acid, benzenesulfonic acid, p-toluenesulfonic acid, methanesulfonic acid, citric acid, tartaric acid, oxalic acid, propionic acid, maleic acid, malic acid, malonic acid, fumaric acid, mandelic acid, ascorbic acid, etc. according to a conventional method, by conventional means as mentioned above. In case where a carboxy group or the like is contained as a substituent in the compound, said compound can be converted to a salt with alkali metal or alkaline earth metal as exemplified before according to a conventional method, and can be isolated and purified by conventional means as mentioned above.

Thus prepared compounds (I) of this invention or their salts possess an excellent effect for preventing and controlling various kinds of plant diseases caused by pathogenic fungi, especially downy mildew of vegetables such as cucumber, Chinese cabbage, onion, pulse, etc. and fruit trees such as vine, citrus, apple, etc., plant blight of tomato, potato, egg plant, green pepper, pumpkin, etc. Further, the compounds of this invention and their salts maintain the stable fungicidal effect for a considerably long period of time after applying to plants (long-lasting effect), and suffer less in reduction of the efficacy due to a little washing off by rain after application by spraying (rain-resistance effect). Thus, the compounds (I) and their salts exert sufficient effects even in the rainy season when downy mildew or plant blight occurs frequently. And further, the compounds (I) of this invention and their salts possess safe and advantageous qualities as an agricultural fungicide, because damage to plants is low and toxicity to fish is also low.

The compound (I) of this invention or its salt can be used as a fungicide in a conventional form of agricultural chemicals. That is, a kind or two or more kinds of the compounds (I) of this invention and their salts may preferably be used in accordance with the purpose in a form of emulsifiable concentrate, oily preparation, spray, wettable powder, powder, tablet, ointment, etc., which can be formed with a suitable carrier or carriers in a conventional manner, for example, by dissolving or dispersing in a proper liquid carrier, by mixing with a proper solid carrier or adsorbing on a proper solid carrier. If necessary, an emulsifying agent, suspending agent, spreading agent, penetrating agent, moisturizing agent, adhesive, stabilizing agent, etc. may be added to the aforementioned preparations, which can be prepared by a conventional method.

The suitable ratio of the compound (I) of this invention or its salt to the total fungicidal composition is about 1 to 80% by weight for emulsifiable concentrate or wettable powder, about 0.1 to 10% by weight for oily preparation and powder, and about 5 to 50% by weight for granules, though the concentration of the active ingredient may be varied in accordance with the purpose. The emulsifiable concentrates, wettable powders or the like are suitably diluted and extended (for example to 100–5000 times) with water or the like on the occasion of use, and then scattered.

Suitable liquid carrier (solvent) to be used may be, for example, water, alcohols (e.g. methanol, ethanol, n-propanol, isopropyl alcohol, ethylene glycol, etc.), ethers (e.g. dioxane, tetrahydrofuran, ethylene glycol monomethyl ether, diethylene glycol monomethyl ether, propylene glycol monomethyl ether, etc.), ketones (e.g. acetone, methyl ethyl ketone, etc.), aliphatic hydrocarbons (e.g. kerosine, kerosene, fuel oil, machine oil, etc.), aromatic hydrocarbons (e.g. benzene, toluene, xylene, solvent naphtha, methylnaphthanlene, etc.), halogenated hydrocarbons (e.g. methylene chloride, chloroform, carbon tetrachloride, etc.), acid amides (e.g. dimethylformamide, dimethylacetamide, etc.), esters (e.g. ethyl acetate, butyl acetate, fatty acid glycerol ester, etc.), nitriles (e.g. acetonitrile, propionitrile, etc.), or the like. These liquid carriers may be used individually or as an optional mixture thereof.

Suitable solid carrier (diluent or extender) may be vegetable powders (e.g. soybean flour, tobacco flour, wheat flour, sawdust, etc.), mineral powders (e.g. clays such as kaolin, bentonite, acid clay, talcs such as talc powder, pyropyllite, silicas such as diatomaceous earth, mica powder, etc.), alumina, sulfur powder, active carbon, or the like. These solid carriers may be used individually or as an optional mixture thereof.

Suitable base for the ointment may be, for example, polyethylene glycol, pectin, polyalcohol esters of higher fatty acids such as glycerin mono-stearate, etc. cellulose derivatives such as methyl cellulose, etc., sodium alginate, bentonite, higher alcohols, polyalcohols such as glycerin, etc., vaseline, white petrolatum, liquid paraffin, lard, various kinds of vegetable oils, lanolin, dehydrated lanolin, hard oil, resins, or the like. These bases may be used individually or as an optional mixture thereof, or together with the surface active agent exemplified in the following.

Suitable surface active agent to be used, if necessary, as the emulsifying agent, spreading agent, penetrating agent, dispersing agent, etc. may be nonionic or anionic surface active agents such as soaps, polyoxyalkyl aryl esters (e.g. Nonal®, manufactured by Takemoto Yushi K.K., Japan), alkyl sulfates (e.g. Emal 10®, Eemal 40®, manufactured by Kao-Atlas K.K., Japan), alkyl sulfonates (e.g. Neogen®, Neogen T®, manufactured by Dai-ichi Kogyo Seiyaku K.K., Japan: Neopellex®, manufactured by Kao-Atlas K.K., Japan), polyethylene glycol ethers (e.g. Nonipol 85®, Nonipol 100®, Nonipol 160®,manufactured by Sanyo Kasei K.K. Japan), polyalcohol esters (e.g. Tween 20®, Tween 80®, manufactured by Kao-Atlas K.K., Japan), or the like.

The fungicide of this invention can be applied at any time from seeds nursery plant to harvest. The fungicide of this invention can be used for controlling the outbreak of plant blight by previous administration and also for curing the plant blight by administration after the outbreak according to a conventional method.

The amount of the compound (I) of this invention or its salt to be used as agricultural chemicals is variable in accordance with conditions such as growth stage and growth situation of the plant to be applied, kind of the plant blight, situation of the outbreak, administration time and method of the fungicide, etc. The compound (I) or its salt is usually used in an amount of about 3 to 300 g, preferably about 10 to 100 g per 10 are. The concentration of the active ingredient to be applied is preferably about 10 to 1000 ppm. The fungicide is usually applied by direct scattering, direct powdering or irrigating to the plant or by powdering to seeds. The amount, concentration and method of application may optionally be varied so far as the fungicide is used safely and effectively. The fungicide of this invention may be used, if necessary, in an optional combination with another kind of fungicides (e.g. organic chlorine fungicide, organic phosphorus fungicide, benzimidazole-type fungicide, copper fungicide, organic sulfur fungicide, phenolic fungicide, triazole-type fungicide, pyrimidine-type fungicide, acrylic acid-type fungicide, sulfenamide-type fungicide, amino acid-type fungicide, antibiotic substance, etc.), insecticides (e.g. natural insecticide, carbamate-type insecticide, organic phosphorus insecticide, neraistoxin-type insecticide, synthesized pyrethroid, etc.), miticides, nematicides, herbicides, plant hormone drugs, plant growth regulators, stabilizing agents, synergists, attracting agents, repellents, perfumes, coloring agents, fertilizers, plant nutrients, various kinds of aminoacids, low or high molecular phosphoric acids, or the like. Metal salts (e.g. copper chloride, copper sulfate, etc.) may also be added for the purpose of synergy.

The compounds (I) provided by this invention and their salts exhibit an excellent control or preventive effect against downy mildew and blight of vegetables and fruit trees. The compounds (I) or their salts are not washed away, possess an excellent rain-resistant property and accordingly exhibit the excellent control or prevent effect especially in a rainy season. The compounds (I) of this invention and their salts decrease the blight of vegetables and fruit trees, and can be used as an advantageous fungicide with no substantial damage to the crops.

Test 1 Prevention of blight of tomato

A compound of this invention was dissolved in dimethylformamide (final concentration: 1% by weight). xylene (final concentration: 0.02% by weight) and Tween 20® (final concentration 0.02% by weight) were added to the solution, and the mixture was diluted with water to a fixed concentration of the active ingredient. To this solution was added a spreading agent, Dyne® (manufactured by Takeda Chemical Industries, Ltd., containing 20% (w/w) of polyoxyethylene nonyl phenyl ether and 12% of calcium lignin sulfonate) in a rate of 0.05% (w/w) (final concentration) to give a scattering solution. The solution was sprayed to young seedlings (about 4 weeks seedling) of tomato to an extent that the solution fell in drops. After air-drying, a suspension of zoosporangia of pathogen of tomato blight (concentration: about $10^5$/ml) was inoculated by spraying. After the inoculation, the plants were kept in a humid room at 17° C. for 5 days. The rate of area of the affected spots in the plant was surveyed, and the prevention value was shown in accordance with the following coefficients.

Prevention value 3: affected area 0–5%
Prevention value 2: affected area 6–15%
Prevention value 1: affected area 16–30%
Prevention value 0: affected area 31% or more.
The results are shown in Table 1.

Test 2 Prevention of downy mildew of cucumber.

A scattering solution containing a compound of this invention in a fixed concentration was prepared by the method described in the above Test 1, and the solution was sprayed to young seedlings (about 3 weeks seedling) of cucumber to an extent that the solution fell in drops. After air-drying, a suspension of zoosporangia of pathogen of downy mildew of cucumber (concentration: about $10^5$/ml) was inoculated by spraying. After the inoculation, the plants were kept in a humid room at 20° C. for one day and further in a humid room for 6 days. The rate of area of the affected spots in the plant was surveyed, and the prevention value was shown in accordance with the following coefficients.

Prevention value 3: affected area 0–5%
Prevention value 2: affected area 6–15%
Prevention value 1: affected area 16–30%
Prevention value 0: affected area 31% or more
The results are shown in Table 2.

Test 3 Prevention of downy mildew of vine.

A scattering solution containing a compound of this invention in a fixed concentration was prepared by the method described in the above Test 1, and the solution was sprayed on young trees of vine (about 6 weeks seedling) to an extent that the solution fell in drops. After air-drying, a suspension of zoosporangia of pathogen of downy mildew of vine (concentration: about $10^5$/ml) was inoculated by spraying. After inoculation, the plants were kept in a humid room at 18° C. for 10 days. The rate of area of the affected spots in the plant was surveyed, and the prevention value was shown in accordance with the following coefficients.

Prevention value 3: affected area 0–5%
Prevention value 2: affected area 6–15%
Prevention value 1: affected area 16–30%
Prevention value 0: affected are 31% or more
The results are shown in Table 3.

In the following Tables 1–3, the numbers in the column of the test compound mean the compound No. obtained in the Examples described below.

TABLE 1

| Prevention of blight of tomato | | | |
|---|---|---|---|
| Compound No. | 200 ppm | Compound No. | 200 ppm |
| 2-1 | 3 | 2-45 | 3 |
| 2-2 | 3 | 2-46 | 3 |
| 2-3 | 3 | 2-52 | 3 |
| 2-4 | 3 | 2-54 | 3 |
| 2-5 | 3 | 2-55 | 3 |
| 2-7 | 3 | 2-56 | 3 |
| 2-9 | 3 | 2-57 | 3 |
| 2-10 | 3 | 2-58 | 3 |
| 2-11 | 2 | 2-59 | 3 |
| 2-15 | 3 | 2-63 | 3 |
| 2-18 | 3 | 2-64 | 3 |
| 2-19 | 3 | 2-65 | 3 |
| 2-20 | 3 | 2-66 | 3 |
| 2-24 | 3 | 2-67 | 3 |
| 2-25 | 3 | 2-68 | 3 |
| 2-26 | 3 | 2-69 | 3 |
| 2-27 | 3 | 2-70 | 2 |
| 2-32 | 3 | 2-71 | 3 |
| 2-33 | 3 | 2-72 | 3 |
| 2-34 | 3 | 2-73 | 3 |
| 2-35 | 2 | 2-78 | 3 |
| 2-41 | 2 | | |
| 2-79 | 3 | 2-145 | 3 |
| 2-80 | 3 | 2-146 | 3 |
| 2-81 | 1 | 2-147 | 3 |
| 2-82 | 3 | 2-148 | 3 |
| 2-83 | 3 | 2-149 | 3 |
| 2-92 | 2 | 2-150 | 3 |
| 2-104 | 3 | 2-151 | 3 |
| 2-109 | 3 | 2-152 | 3 |
| 2-114 | 3 | 2-153 | 3 |
| 2-115 | 2 | 2-154 | 3 |
| 2-119 | 3 | 2-155 | 3 |
| 2-120 | 3 | 2-156 | 3 |
| 2-121 | 3 | 2-157 | 3 |

TABLE 1-continued

Prevention of blight of tomato

| Compound No. | 200 ppm | Compound No. | 200 ppm |
|---|---|---|---|
| 2-122 | 3 | 2-158 | 3 |
| 2-123 | 3 | 2-159 | 3 |
| 2-127 | 3 | 2-160 | 3 |
| 2-128 | 3 | 2-161 | 3 |
| 2-134 | 3 | 2-162 | 3 |
| 2-135 | 3 | 2-163 | 3 |
| 2-136 | 3 | 2-164 | 3 |
| 2-137 | 3 | 2-166 | 3 |
| 2-138 | 3 | 2-167 | 3 |
| 2-139 | 3 | 2-168 | 3 |
| 2-140 | 3 | 2-170 | 3 |
| 2-141 | 3 | 2-171 | 3 |
| 2-142 | 3 | 2-173 | 3 |
| 2-143 | 3 | 2-174 | 3 |
| 2-144 | 3 | 2-175 | 3 |
| 2-176 | 3 | 2-190 | 3 |
| 2-177 | 3 | 2-194 | 3 |
| 2-178 | 3 | 2-195 | 3 |
| 2-179 | 3 | 2-196 | 3 |
| 2-180 | 3 | 2-197 | 3 |
| 2-181 | 3 | 2-198 | 3 |
| 2-182 | 3 | 2-200 | 3 |
| 2-183 | 3 | 2-201 | 3 |
| 2-184 | 3 | 2-203 | 3 |
| 2-185 | 3 | 2-204 | 3 |
| 2-186 | 3 | 2-211 | 3 |
| 2-187 | 3 | 2-212 | 3 |
| 2-188 | 3 | 2-214 | 3 |
| 2-189 | 3 | 2-215 | 3 |

TABLE 2

Prevention of downy mildew of cucumber

| Compound No. | 200 ppm | Compound No. | 200 ppm |
|---|---|---|---|
| 2-1 | 3 | 2-41 | 3 |
| 2-2 | 3 | 2-42 | 3 |
| 2-3 | 3 | 2-45 | 3 |
| 2-4 | 3 | 2-46 | 3 |
| 2-5 | 3 | 2-48 | 3 |
| 2-7 | 3 | 2-52 | 3 |
| 2-9 | 3 | 2-54 | 3 |
| 2-10 | 3 | 2-55 | 3 |
| 2-11 | 3 | 2-56 | 3 |
| 2-15 | 3 | 2-57 | 3 |
| 2-18 | 3 | 2-58 | 3 |
| 2-19 | 3 | 2-59 | 3 |
| 2-20 | 3 | 2-63 | 3 |
| 2-24 | 3 | 2-64 | 3 |
| 2-25 | 3 | 2-65 | 3 |
| 2-26 | 3 | 2-66 | 3 |
| 2-27 | 3 | 2-67 | 3 |
| 2-28 | 3 | 2-68 | 3 |
| 2-29 | 3 | 2-69 | 3 |
| 2-32 | 3 | 2-70 | 3 |
| 2-33 | 3 | 2-71 | 3 |
| 2-34 | 3 | 2-72 | 3 |
| 2-35 | 2 | 2-73 | 3 |
| 2-37 | 3 | 2-78 | 3 |
| 2-40 | 1 | 2-79 | 3 |
| 2-81 | 3 | 2-148 | 3 |
| 2-82 | 3 | 2-149 | 3 |
| 2-83 | 3 | 2-150 | 3 |
| 2-92 | 3 | 2-151 | 3 |
| 2-104 | 3 | 2-152 | 2 |
| 2-109 | 3 | 2-153 | 3 |
| 2-114 | 3 | 2-154 | 3 |
| 2-115 | 3 | 2-155 | 3 |
| 2-119 | 3 | 2-156 | 3 |
| 2-120 | 3 | 2-157 | 3 |
| 2-121 | 3 | 2-158 | 3 |
| 2-122 | 3 | 2-159 | 3 |

TABLE 2-continued

Prevention of downy mildew of cucumber

| Compound No. | 200 ppm | Compound No. | 200 ppm |
|---|---|---|---|
| 2-123 | 3 | 2-160 | 3 |
| 2-127 | 3 | 2-161 | 3 |
| 2-128 | 3 | 2-162 | 3 |
| 2-134 | 3 | 2-163 | 3 |
| 2-135 | 3 | 2-164 | 3 |
| 2-136 | 3 | 2-166 | 3 |
| 2-137 | 3 | 2-167 | 3 |
| 2-138 | 3 | 2-168 | 3 |
| 2-139 | 3 | 2-170 | 3 |
| 2-140 | 3 | 2-171 | 3 |
| 2-141 | 3 | 2-173 | 3 |
| 2-142 | 3 | 2-174 | 3 |
| 2-143 | 3 | 2-175 | 3 |
| 2-144 | 3 | 2-176 | 3 |
| 2-145 | 3 | 2-177 | 3 |
| 2-146 | 3 | 2-178 | 3 |
| 2-147 | 3 | 2-179 | 3 |
| 2-180 | 3 | 2-195 | 3 |
| 2-181 | 3 | 2-196 | 3 |
| 2-182 | 3 | 2-197 | 3 |
| 2-183 | 3 | 2-200 | 3 |
| 2-184 | 3 | 2-201 | 3 |
| 2-185 | 3 | 2-203 | 3 |
| 2-186 | 3 | 2-204 | 3 |
| 2-187 | 3 | 2-211 | 3 |
| 2-188 | 3 | 2-212 | 3 |
| 2-189 | 3 | 2-214 | 3 |
| 2-190 | 3 | 2-215 | 3 |
| 2-194 | 3 | | |

TABLE 3

Prevention of downy mildew of vine

| Compound No. | 200 ppm | Compound No. | 200 ppm |
|---|---|---|---|
| 2-1 | 3 | 2-35 | 3 |
| 2-2 | 3 | 2-36 | 3 |
| 2-4 | 3 | 2-37 | 3 |
| 2-5 | 3 | 2-41 | 3 |
| 2-7 | 3 | 2-42 | 1 |
| 2-9 | 2 | 2-46 | 2 |
| 2-10 | 2 | 2-48 | 3 |
| 2-11 | 3 | 2-49 | 3 |
| 2-15 | 3 | 2-50 | 2 |
| 2-18 | 2 | 2-54 | 2 |
| 2-19 | 3 | 2-55 | 3 |
| 2-20 | 2 | 2-56 | 3 |
| 2-24 | 3 | 2-57 | 3 |
| 2-25 | 3 | 2-58 | 3 |
| 2-26 | 3 | 2-59 | 3 |
| 2-27 | 3 | 2-63 | 2 |
| 2-34 | 3 | 2-64 | 2 |
| 2-65 | 3 | 2-143 | 3 |
| 2-66 | 3 | 2-144 | 3 |
| 2-67 | 3 | 2-145 | 3 |
| 2-68 | 2 | 2-146 | 3 |
| 2-69 | 3 | 2-147 | 3 |
| 2-70 | 3 | 2-148 | 3 |
| 2-71 | 2 | 2-149 | 3 |
| 2-72 | 2 | 2-150 | 3 |
| 2-73 | 3 | 2-151 | 3 |
| 2-78 | 2 | 2-152 | 3 |
| 2-79 | 3 | 2-153 | 3 |
| 2-82 | 3 | 2-154 | 3 |
| 2-83 | 3 | 2-155 | 3 |
| 2-92 | 3 | 2-156 | 3 |
| 2-104 | 1 | 2-157 | 3 |
| 2-109 | 3 | 2-158 | 3 |
| 2-119 | 3 | 2-159 | 3 |
| 2-120 | 3 | 2-160 | 3 |
| 2-121 | 3 | 2-161 | 3 |
| 2-122 | 3 | 2-162 | 3 |

TABLE 3-continued

Prevention of downy mildew of vine

| Compound No. | 200 ppm | Compound No. | 200 ppm |
| --- | --- | --- | --- |
| 2-123 | 3 | 2-163 | 3 |
| 2-127 | 3 | 2-164 | 2 |
| 2-128 | 3 | 2-165 | 2 |
| 2-134 | 2 | 2-166 | 3 |
| 2-135 | 3 | 2-167 | 3 |
| 2-140 | 3 | 2-168 | 3 |
| 2-141 | 3 | 2-170 | 3 |
| 2-142 | 3 | 2-171 | 3 |

It is shown by the above test results that the compounds (I) of this invention and their salts possess an excellent effect in preventing the downy mildew and blight of vegetables and fruit trees.

(f) Examples

This invention is explained in more detail by the following Examples. However, this invention shall not be limited to these Examples.

In the following Examples, elution in the column chromatography was carried out under the observation of TLC (Thin Layer Chromatography). The observation of TLC was conducted by using Kiesel gel 60F 254 (Art·5715) manufactured by Merck & Co. as a TLC plate, the same solvent as the one used as an eluent of column chromatography as a developing solvent, and UV detector as a detecting method. The silica gel filled in a column was Kiesel gel 60 (70–230 mesh, Art. 7734) manufactured by Merck & Co. The NMR spectrum means proton NMR ($^1$HNMR), and tetramethylsilane was used as an internal or external standard. The NMR spectrum was measured by VARIAN EM 390 (90 MHz) type spectrometer in case special description is not given, and each δ value was shown by ppm. Numerical value in the parentheses means mixing rate by volume of each solvent used in a mixed solvent as an eluent.

Each abridgment used in the following Examples has the following meanings.

s: singlet, d: doublet, m: multiplet, br: broad, J: coupling constant, Hz: Hertz, $CDCl_3$: heavy chloroform, $DMSOd_6$: heavy dimethyl sulfoxide, % (except for yield) : w/w %.

The room temperature means about 15° to 25° C.

Example 1

Syntheses of methyl imidazo[1,2-a]pyridine-8-carboxylate (Compound No. 1-1)

47% Hydrogen bromide (2.5ml, 14.4 m moles) was added to diethoxybromoethane (2.0ml, 13.2 m moles), and the mixture was stirred at 50° C. for 2 hours. The reaction mixture was cooled to room temperature, and ethanol (7.0 ml) and sodium bicarbonate (1.0 g, 11.9 m moles) were added thereto. The mixture was stirred, and insoluble substance was filtered off. To the filtrate were added methyl 2-aminonicotinate (1.0 g, 6.6 m moles), sodium bicarbonate (2.0 g, 13.8 m moles) and ethanol (7.0 ml), and the mixture was refluxed under heating for 4 hours. The reaction mixture was cooled to room temperature, and saturated aqueous solution of sodium bicarbonate was added thereto. The mixture was extracted with dichloromethane (100 ml×3), and the extract was washed with water, dried over anhydrous magnesium sulfate ($MgSO_4$) and concentrated under reduced pressure. The concentrate was purified by column chromatography on silica gel (eluent: chloroform and then chloroform/methanol=9/1) to give the object compound (0.6 g, yield 55%) as yellow crystals. m.p. 67°–69° C.

Example 2

Synthesis of methyl 2-methylimidazo[1,2-a]pyridine- 8-carboxylate (Compound No. 1-3)

Bromoacetone (6.5 g, 42.7 m moles) and methyl 2-aminonicotinate (4.8 g, 31.5 m moles) were added to ethanol (50 ml), and the mixture was refluxed under heating for 17 hours. The reaction mixture was cooled to room temperature, and the solvent was distilled off under reduced pressure. Saturated aqueous solution of sodium bicarbonate (50 ml) was added to the residue, and the mixture was extracted with chloroform (100 ml×3). The extract was washed with water, dried over $MgSO_4$ and concentrated under reduced pressure. The concentrate was purified by column chromatography on silica gel (eluent:chloroform and then chloroform/methanol=9/1) to give the object compound (4.0 g, yield 85%) as an oily substance.

Example 3

Synthesis of hydrogen bromide salt of ethyl 2-phenyl-imidazo[1,2-a]pyridine-8-carboxylate (Compound No. 1-25).

Phenacyl bromide (11.0 g, 55.3 m moles) and ethyl 2-aminonicotinate 18.68 g, 52.2 m moles) were added to methyl ethyl ketone (100 ml), and the mixture was refluxed under heating for 5.5 hours. The reaction mixture was left to stand at room temperature overnight, and the precipitating crystals were collected by filtration to give the object compound (16.3 g, yield 89.96%) as crystals. m.p. 174°–176° C.

Example 4

Synthesis of methyl 3-chloro-2-methylimidazo[ 1,2-a] pyridine-8-carboxylate (Compound No. 1-15).

Methyl 2-methylimidazo[1,2-a]pyridine-8carboxylate (5.3 g, 27.9 m moles) was dissolved in chloroform (30 ml), and N-chlorosuccinimide (3.7 g, 27.9 m moles) was added to the solution and reacted at room temperature for 40 minutes. To the reaction mixture was added 10% aqueous solution of sodium carbonate (80 ml), and the mixture was stirred for 30 minutes. The organic layer was separated from the reaction mixture, and the aqueous layer was extracted with chloroform (10 ml×3). The extracts were combined, washed with water, dried over $MgSO_4$ and concentrated under reduced pressure. The concentrate was purified by column chromatography on silica gel (eluent:chloroform) to give the object compound (3.6 g, yield 57%) as an oily substance.

Example 5

Synthesis of methyl 3-dimethylaminomethyl-2-methylimidazo[ 1,2-a]pyridine-8-carboxylate (Compound No. 1-17).

To acetonitrile (10 ml) were added 37% formaldehyde (0.3 ml) and acetic acid (0.4 ml), and 50% aqueous solution of dimethylamine (0.3 ml) was added slowly to the mixture at 0° C. with stirring. Methyl 2-methylimidazo[1,2-a]pyridine-8-carboxylate (1.0 g, 3.7 m moles) was added to the mixture and reacted at 50° C. for 2 hours and then at room temperature for 2.5 hours. The reaction mixture was concentrated under reduced pressure and neutralized with saturated aqueous solution of NaHCO₃. The solution was extracted with dichloromethane, and the extract was washed with water, dried over anhydrous sodium sulfate and concentrated under reduced pressure to give the object compound (0.48 g, Yield 52%) as crystals. m.p. 123°–124° C.

Example 6

Synthesis of
2-methylimidazo[1,2-a]pyridine-8-carboxylic acid
(Compound No. 1-4)

Methyl 2-methylimidazo[1,2-a]pyridine-8-carboxylate (4 g, 21 m moles) was dissolved in a mixture of ethanol (45 ml) and water (20 ml), and sodium hydroxide (2.5 g, 63 m moles) was added thereto and refluxed under heating for 30 minutes. The reaction mixture was cooled to room temperature and concentrated under reduced pressure. Water (40 ml) was added to the concentrate, and the mixture was adjusted to pH 4 with conc. hydrochloric acid. The precipitating crystals were collected by filtration to give the object compound (2.3 g, yield 64%).

Example 7

Synthesis of
2-phenylimidazo[1,2-a]pyridine-8-carboxylic acid
(Compound No. 1-26)

Hydrogen bromide salt of ethyl 2-phenylimidazo-[1,2.-a]pyridine-8-carboxylate (8.4 g, 24.2 m moles) was added to 20% aqueous solution of NaOH (200 ml) and ethanol (100 ml), and the mixture was refluxed under heating for 1 hour. The reaction mixture was cooled to room temperature, and alcohol was distilled off under reduced pressure. The concentrate was adjusted to pH 4 with conc. hydrochloric acid, and the precipitating crystals were collected by filtration to give the object compound (5.67 g, yield 98.4%) as crystals. m.p. 226° C.

Example 8

Synthesis of
2-chloromethylimidazo[1,2-a]-pyridine-
8-carboxylic acid (Compound No. 1-90)

Ethyl 2-chloromethylimidazo[1,2-a]pyridine-8-carboxylate (8.4 g, 35.2 m moles) was added to conc. hydrochloric acid 1100 ml), and the mixture was refluxed under heating for 5 hours. The reaction mixture was cooled to room temperature and adjusted to pH 4 with saturated aqueous solution of sodium bicarbonate. The precipitating crystals were collected by filtration to give the object compound (5.67 g, yield 98.4%) as crystal. m.p. 250° C. (decomp.).

Example 9

Synthesis of 3-nitro-2-(4-nitrophenyl)-imidazo
[1,2-a]pyridine-3-carboxylic acid (Compound No.
1-96)

Ethyl 2-phenylimidazo[1,2-a]pyridine-8-carboxylate (2.9, 10 m mol) was dissolved in conc. sulfuric acid (5 ml), and to the solution was slowly added 70% nitric acid (1.3 ml) at 10° C. After addition, the mixture was stirred at room temperature for 30 minutes, poured into ice water and adjusted to pH 7 by adding 20% sodium hydroxide. The precipitated crystals were collected by filtration, which were ethyl ester of the title compound (3.6 g, yield 99.2%). A solution of the crystals in conc. hydrochloric acid (35 ml) was refluxed for 1.5 hours and cooled to room temperature. The precipitated crystals were collected by filtration and dried to give the object compound (2.9 g, yield 87.3%). m.p. >300° C.

Example 10

Synthesis of
3-nitromidazo[1,2-a]pyridine-8-carboxylic acid
(Compound No. 1 - 125)

Ethyl 2-ethoxycarbonylimidazo[1,2-a]pyridine-8-carboxylate (3.8 g, 14.5 m mol) was dissolved in conc. sulfuric acid (10 ml), and to the solution was slowly added 70% nitric acid (1.5 ml) at 10° C. The mixture was stirred at room temperature for 30 minutes, poured into ice water and adjusted to pH 7 by adding 20% sodium hydroxide. The precipitated crystals were filtered to obtain ethyl 2-ethoxycarbonyl-3-nitro-imidazo[1,2-a]pyridine- 8-carboxylate (2.4 g, yield 53.8%) as crystals of m.p. 139°–140° C. A solution of the crystals in conc. hydrochloric acid (35 ml) was refluxed for 1.5 hours and cooled to room temperature. The precipitated crystals were collected by filtration and dried to give the object compound (1.2 g, yield 74.3%) of m.p.>300° C.

Example 11

Synthesis of ethyl 3-formyl-2-phenyl-imidazo
[1,2-a]pyridine-8-carboxylate (Compound No. 1 -
119)

To a solution of ethyl 2-phenyl-imidazo[1,2-a]-pyridine-8-carboxylate hydrogen bromide (14.7 g, 4 m mol) in DMF (8 ml) was dropwise added phosphorus oxychloride (2 ml) keeping the inner temperature to below 15° C. Then, the mixture was allowed to react at room temperature for 30 minutes and at 70° C. for 2 hours. After completion of the reaction, the reaction mixture was cooled, poured into ice water and adjusted to pH 7 by adding 20% sodium hydroxide. The precipitated crystals were collected by filtration and recrystallized from ethanol to obtain the object compound (1.0 g, yield 85.5%) as colorless crystals. m.p. 139° C.

Example 12

Synthesis of ethyl 3-cyano-2-phenyl-imidazo
[1,2-a]pyridin-8-carboxylate (Compound No. 1-121)

Ethyl 2-phenyl-imidazo[1,2-a]pyridine-8-carboxylate hydrogen bromide (1.96 g, 5.35 m mol), and triethylamine (0.55 g, 5.44 m mol) were added to acetonitrile (20 ml). To this solution was dropwise added a solution of chlorosulfonylisocyanate (ClSO₂NCO) (0.8 ml, 9.19 m mol) in acetonitrile (5 ml) at an inner temperature of 0°–20° C. Then, the mixture was allowed to react at room temperature for an hour. After completion of the reaction, the mixture was concentrated under reduced pressure. The resulting concentrate to which water was added was extracted with dichloromethane, and the extract was washed with water, dried over anhydrous sodium sulfate and concentrated under reduced pressure. The residue was purified by silica gel column chromatography (eluent: chloroform) to give the object compound (1.06 g, yield 67.9%) as crystals. m.p. 87°–89° C.

Example 13

Synthesis of ethyl 2-ethoxycarbonyl-imidazo[1,2-a]pyridine-8-carboxylate (Compound No. 1-123)

A mixture of ethyl bromopyruvate (2.3 g, 10.2 m mol and ethyl 2-aminonicotinate (1.7 g, 10 m mol) in methyl ethyl ketone (17 ml) was refluxed for 5 hours. After completion of the reaction, the mixture was cooled to room temperature and distilled under reduced pressure to remove the solvent. The residue to which saturated sodium hydrogen carbonate aqueous solution (50 ml) was added was extracted with chloroform (100 ml×3). The extract was washed with water, dried over $MgSO_4$ and concentrated under reduced pressure. The concentrate was purified by silica gel column chromatography (eluent: ethyl acetate) to give the object compound (0.7 g, yield 26.7%) as crystals. m.p. 97° C.

Example 14

Synthesis of ethyl 2-methyl-3-sulfoimidazo[1,2-a]imidazo[1,2-a]pyridine-8-carboxylate (Compound No. 1-127)

To a solution of ethyl 2-methyl-imidazo[1,2-a]-pyridine-8-carboxylate (1.2 g, 5.9 m mol) in chloroform (15 ml) was added chlorsulfonic acid (0.6 ml). The mixture was reflexed for 3 hours, and then concentrated under reduced pressure. The precipitated crystals were collected by filtration, washed sufficiently with water and dried to give the object compound (1.2 g, yield 71.4%) as crystals. m.p. 247°–250° C. (decomp.).

Example 15

Synthesis of ethyl 2-methyl-3-N-methylsulfamoylimidazo[1,2-a]pyridine-8-carboxylate (Compound No. 1-129)

Ethyl 2-methyl-3-sulfo-imidazo[1,2-a]pyridine-8-carboxylate (1.7 g) and tri-n-propylamine (2.6 g) were added to acetonitrile (17 ml). Phosphorus oxychloride (1.1 ml) was added to the mixture, keeping the inner temperature to 50°–60° C. Then, the mixture was allowed to react at the same temperature for an hour. After completion of the reaction, the mixture was concentrated under reduced pressure, and water was added to the residue. The precipitated crystals were collected by filtration, washed with water and dried to obtain ethyl 2-methyl-3-chlorosulfonyl-imidazo[1,2-a]-pyridine- 8-carboxylate (1.2 g, yield 66.3%) as crystals of m.p. 182°–183° C.

The crystals (1.2 g) were dissolved in acetonitrile (12 ml), to which a solution of 40% methylamine aqueous solution (0.75 g) in acetonitrile (3 ml) was dropwise added at an inner temperature of 0°–10° C. Then, the mixture was allowed to react at room temperature for an hour. After completion of the reaction, the mixture was concentrated under reduced pressure. The concentrate to which water was added was adjusted to pH 7 with dilute hydrochloric acid. The precipitated crystals were collected by filtration, washed with water and dried to obtain the object compound (1.1 g, yield 93.2%) as crystals. m.p. 184°–185° C.

Example 16

Synthesis of 2-chloro-imidazo[1,2-a]pyridine-8-carboxylic acid (Compound No. 1-135)

A mixture of diethyl bromomalonate (26 ml) and ethyl 2-aminonicotinate (13.3 g) was allowed to react at 80°–90° C. for 6 hours under nitrogen atmosphere. After completion of the reaction, the mixture was cooled to room temperature, and acetone (100 ml) was added thereto. The precipitated crystals were collected by filtration, affording 3,8-diethoxycarbonyl-2-hydroxy-imidazo[1,2-a]pyridine hydrobromide (9.98 g, yield 34.8%).

A mixture of the crystals (6.6 g) in phosphorus oxychloride (30 ml) was reacted at 160° C. for 2 hours in a pressure reaction vessel. After completion of the reaction, excess phosphorus oxychloride was removed under reduced pressure. Ethanol was added to the residue, and the mixture was concentrated under reduced pressure. The concentrate was purified by silica gel column chromatography (eluent: chloroform) to obtain 2-chloro-3,8-diethoxycarbonyl-imidazo-[1,2-a]pyridine (Compound No. 1-133) (2.2 g, yield 40.3%) as crystals of m.p. 105°–106° C.

The crystals (0.9 g) were dissolved in ethanol (10 ml), and 10% sodium hydroxide (5 ml) was added thereto. The mixture was allowed to react at room temperature for an hour and then adjusted to pH 4 with conc. hydrochloric acid. The precipitated crystals were collected by filtration, washed with water and dried to obtain 2-chloro-imidazo[1,2-a]pyridine-3,8-dicarboxylic acid (0.73 g, yield 100%) as crystals of m.p. 210°–212° C. (decomp.). Then, a mixture of the crystals (0.73 g) in conc. hydrochloric acid (5 ml) was refluxed for 2 hours. The reaction solution was adjusted to pH 4 with saturated sodium hydrogen carbonate aqueous solution, to yield crystals of the object compound (0.5 g, yield 83.9%). m.p. 237° C.

Example 17

Synthesis of α-(imidazo[1,2-a]pyridin-8-ylcarbonylamino)-(2-furyl)acetonitrile (Compund No. 2-1)

α-(2-Furyl)-α-aminoacetonitrile (0.7 g, 5.5 m mols) was dissolved in acetonitrile (20 ml), and imidazo[1,2-a]pyridine-8-carboxylic acid chloride (1.0 g, 5.5 m moles) was added thereto with stirring and reacted at room temperature for 2 hours. After completion of the reaction, the solvent was removed from the reaction mixture under reduced pressure. To the residue were added water (20 ml), saturated aqueous solution of sodium. bicarbonate (50 ml) and chloroform (50 ml), and the mixture was stirred. The organic layer was separated, dried over anhydrous magnesium sulfate and concentrated. The concentrate was purified by column chromatography on silica gel (eluent:ethyl acetate/n-hexane= 2/1) to give the object compound (0.16 g, yield 11%) as crystals. m.p. 149°–151° C.

Example 18

Synthesis of α-(imidazo[1,2-a]pyridin-5-ylcarbonylamino)-(2-furyl)acetonitrile (Compound No.2-134)

α-(2-Furyl)-α-aminoacetonitrile (0.7 g, 5.5 m moles) was dissolved in acetonitrile (20 ml), and imidazo[1,2-a]pyridine-5-carboxylic acid chloride (1.0 g, 5.5 m moles) was added thereto and reacted at room temperature for 2 hours. After completion of the reaction, the solvent was removed from the reaction mixture. To the residue were added water (20 ml), saturated aqueous solution of sodium bicarbonate (50 ml) and chloroform (50 ml), and the mixture was stirred. The organic layer was separated, dried over anhydrous magnesium sulfate and concentrated. The concentrate was purified by column chromatography on silica gel (eluent: methanol/chloroform=1/9) to give the object compound (0.9 g, yield 64%) as amorphous solid.

Example 19

Synthesis of α-(2-phenyl-imidazo[1,2-a]pyridin-8-ylcarbonylamino)-( 2-furyl)acetonitrile (Compound No. 2-24)

2-Phenyl-imidazo[1,2-a]pyridine-8-carboxylic acid (1.5 g, 5.5 m moles) was added to dried tetrahydrofuran (100 ml), and carbonyldiimidazole (1.5 g, 5.5 m moles) was added slowly thereto with stirring at room temperature in an atmosphere of nitrogen gas. The mixture was stirred at room temperature for 8 hours, and α-(2-furyl)-60 -aminoacetonitrile (0.7 g, 5.5 m moles) was added to the mixture and reacted at room temperature for 5 hours. The solvent was removed from the reaction mixture under reduced pressure, and water (20 ml) and ethyl acetate (50 ml) were added to the residue and stirred. The organic layer was separated, dried over anhydrous magnesium sulfate and then concentrated. The concentrate was purified by column chromatography on silica gel (eluent: ethyl acetate/n-hexane=1/1) to give the object compound (0.9 g, yield 64%) as crystals. m.p. 197°–199° C.

Example 20

Synthesis of α-(3-chloro-imidazo[1,2-a]pyridin-8-ylcarbonylamino)-( 2-furyl)acetonitrile (Compound No. 2-10)

3-Chloro-imidazo[1,2-a]pyridine-8-carboxylic acid (1.8 g, 9.2 m moles) was added to thionyl chloride (20 ml), and the mixture was refluxed under heating and stirring for 30 minutes and then concentrated under reduced pressure. The resultant crude acid chloride and α-(2-furyl)-α-aminoacetonitrile (1.1 g, 8.5 m moles) were added to acetonitrile (50 ml) and reacted at room temperature for 1 hour with stirring. The solvent was removed from the reaction mixture under reduced pressure, and water (20 ml), saturated aqueous solution of sodium bicarbonate (50 ml) and chloroform (50 ml) were added to the residue and stirred. The organic layer was separated, dried over anhydrous magnesium sulfate and then concentrated. The concentrate was purified by column chromatography on silica gel (eluent: ethyl acetate/n-hexane=1/2) to give the object compound (0.6 g, yield 22%) as crystals. m.p. 142°–143° C.

Example 21

Synthesis of α-(2-phenyl-imidazo[1,2-a]pyridin-8-ylcarbonylamino)-( 3-chlorophenyl)acetonitrile (Compound No. 2-35)

2-phenyl-imidazo[1,2-a]pyridine-8-carboxylic acid (1.0 g, 4.2 m moles), α-(3-chlorophenyl)-aminoacetonitrile (0.77 g, 4.6 m moles) and NaHCO$_3$ (1.1 g, 13.1 m moles) were added to acetonitrile 110 ml). Phosphorus oxychloride (0.7 ml, 7.51 m moles, dissolved in 5 ml of acetonitrile) was added slowly to the mixture with stirring under ice-cooling. The mixture was reacted at room temperature for 10 hours, and the solvent was removed from the reaction mixture under reduced pressure. Water (50 ml) was added to the residue and the mixture was adjusted to pH 7 with saturated aqueous solution of sodium bicarbonate and then extracted with dichloromethane/ethyl acetate (10/1) (100 ml×2). The extract was dried over anhydrous magnesium sulfate and concentrated. Acetonitrile (5 ml) was added to the concentrate, and the precipitating crystals were collected by filtration to give the object compound (0.44 g, yield 27.2%) as crystals. m.p. 210°–211° C.

Example 22

Synthesis of α-(3-dimethylaminomethyl-2-phenylimidazo[ 1,2-a]pyridin-8-ylcarbonylamino)-(3-fluorophenyl)acetonitrile (Compound No. 2-79)

To acetonitrile (10 ml) were added 37% formaldehyde (0.3 ml) and acetic acid (0.4 ml), and 50% aqueous solution of dimethylamine (0.3 ml) was added slowly thereto at 0° C. with stirring. To the mixture was added α-(2-phenyl-imidazo[1,2-a]pyridin-8-ylcarbonylamino)-( 3-fluorophenyl)acetonitrile (1.0 g, 2.7 m moles), and the mixture was reacted at 50° C. for 2 hours and further stirred at room temperature for 2.5 hours. The reaction mixture was concentrated under reduced pressure, and the concentrate was neutralized with saturated aqueous solution of NaHCO$_3$. The solution was extracted with dichloromethane, and the extract was washed with water, dried over anhydrous sodium sulfate and concentrated under reduced pressure. The concentrate was purified by column chromatography on silica gel (eluent: chloroform) to give the object compound (0.47 g, yield 40.8%) as crystals. m.p. 123°–124° C.

Example 23

Synthesis of α-(3-methylsulfinylmethyl-imidzo [1,2-a]pyridin-8-ylcarbonylamino)-(2-furyl)-acetonitrile (Compound No. 2-122)

α-(2-Methylthiomethyl-imidazo[1,2-a]pyridin-8-ylcarbonylamino)-( 2-furyl)acetonitrile (0.33 g, 1 m mole) was added to chloroform (10 ml), and m-chloroperbenzoic acid (0.25 g, 1.1 m moles) was added to the mixture at internal temperature of 5° C. The mixture was stirred at room temperature for 2.5 hours, and the reaction mixture was treated with saturated aqueous solution of NaHCO$_3$. The chloroform layer was separated, washed with water, dried over anhydrous sodium sulfate and then concentrated under reduced pressure. The concentrate was purified by column chromatography or silica gel (eluent: ethyl acetate) to give the object compound (0.1 g, yield 30.3%) as crystals. m.p. 214°–216° C.

Example 24

Synthesis of α-(2-(trifluoromethyl-imidazo[ 1,2-a]pyridin-8-ylcarbonylamino)-(3-fluorophenyl)acetamide (Compound No. 2-169)

A mixture of α-(2-trifluoromethyl-imidazo[1,2-a]-pyridin- 8-ylcarbonylamino)-(3-fluorophenyl)acetonitrile (1.26 g) and chlorosulfonic acid (0.5 ml) in chloroform (13 ml) was refluxed for 1.5 hours. The reaction solution was concentrated under reduced pressure, and water was added to the residue. The precipitated crystals were collected by filtration and recrystallized from ethanol to obtain the object compound (0.45 g, yield 34.1%) as crystals. m.p. 118°–120° C.

The compounds (II) obtained in a similar manner to those of Examples 1–16 are shown in Table 4, their melting points and NMR data are shown in Table 5, the compounds (I) obtained in a similar manner to those of Examples 17–24 are shown in Table 6, and their melting points and NMR data are shown in Table 7, respectively.

TABLE 4

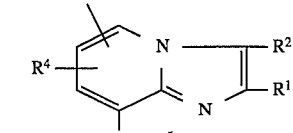

| Compound No. | $R^1$ | $R^2$ | $R^3$ | $R^4$ | $R^5$ |
|---|---|---|---|---|---|
| 1-1 | H | H | H | H | Me |
| 1-2 | H | H | H | H | H |
| 1-3 | Me | H | H | H | Me |
| 1-4 | Me | H | H | H | H |
| 1-5 | Et | H | H | H | Me |
| 1-6 | Et | H | H | H | H |
| 1-7 | nPr | H | H | H | H |
| 1-8 | iPr | H | H | H | Me |
| 1-9 | iPr | H | H | H | H |
| 1-10 | nBu | H | H | H | H |
| 1-11 | tBu | H | H | H | Me |
| 1-12 | tBu | H | H | H | H |
| 1-13 | H | Cl | H | H | Et |
| 1-14 | H | Cl | H | H | H |
| 1-15 | Me | Cl | H | H | Me |
| 1-16 | Me | Cl | H | H | H |
| 1-17 | Me | $CH_2NMe_2$ | H | H | Me |
| 1-18 | Me | $CH_2NMe_2$ | H | H | H |
| 1-19 | Me | Me | H | H | H |
| 1-20 | Me | $CH_2CH_2CN$ | H | H | H |
| 1-21 | Me | CHO | H | H | H |
| 1-22 | Me | $NO_2$ | H | H | H |
| 1-23 | Me | $CH=CMe_2$ | H | H | H |
| 1-24 | $C_6H_5$ | H | H | H | Me |
| 1-25 | $C_6H_5$ | H | H | H | Et |
| 1-26 | $C_6H_5$ | H | H | H | H |
| 1-27 | 2-$MeC_6H_4$ | H | H | H | Me |
| 1-28 | 2-$MeC_6H_4$ | H | H | H | H |
| 1-29 | 2-$MeC_6H_4$ | H | H | H | Et |
| 1-30 | 3-$MeC_6H_4$ | H | H | H | Me |
| 1-31 | 3-$MeC_6H_4$ | H | H | H | H |
| 1-32 | 4-$MeC_6H_4$ | H | H | H | Me |
| 1-33 | 4-$MeC_6H_4$ | H | H | H | H |
| 1-34 | 2,5-$Me_2C_6H_3$ | H | H | H | H |
| 1-35 | 2,4,6-$Me_3C_6H_2$ | H | H | H | H |
| 1-36 | 2-$MeOC_6H_4$ | H | H | H | Me |
| 1-37 | 2-$MeOC_6H_4$ | H | H | H | H |
| 1-38 | 3-$MeOC_6H_4$ | H | H | H | Me |
| 1-39 | 3-$MeOC_6H_4$ | H | H | H | H |
| 1-40 | 4-$MeOC_6H_4$ | H | H | H | Me |
| 1-41 | 4-$MeOC_6H_4$ | H | H | H | H |
| 1-42 | 3,4-$(MeO)_2C_6H_3$ | H | H | H | Et |
| 1-43 | 3,4-$(MeO)_2C_6H_3$ | H | H | H | H |
| 1-44 | 2-$ClC_6H_4$ | H | H | H | Me |
| 1-45 | 2-$ClC_6H_4$ | H | H | H | H |
| 1-46 | 3-$ClC_6H_4$ | H | H | H | Me |
| 1-47 | 3-$ClC_6H_4$ | H | H | H | H |
| 1-48 | 4-$ClC_6H_4$ | H | H | H | Me |
| 1-49 | 4-$ClC_6H_4$ | H | H | H | H |
| 1-50 | 4-$BrC_6H_4$ | H | H | H | Me |
| 1-51 | 4-$BrC_6H_4$ | H | H | H | H |
| 1-52 | 4-$NO_2C_6H_4$ | H | H | H | Me |
| 1-53 | 4-$NO_2C_6H_4$ | H | H | H | H |

TABLE 4-continued

| Compound No. | $R^1$ | $R^2$ | $R^3$ | $R^4$ | $R^5$ |
|---|---|---|---|---|---|
| 1-54 | 2-$FC_6H_4$ | H | H | H | H |
| 1-55 | 2-F,4-$MeC_6H_3$ | H | H | H | H |
| 1-56 | 2-Me,4-$MeSC_6H_3$ | H | H | H | H |
| 1-57 | 2,4,6-$Cl_3C_6H_2$ | H | H | H | H |
| 1-58 | $C_6H_5$ | $CH_2NMe_2$ | H | H | Me |
| 1-59 | $C_6H_5$ | $CH_2NMe_2$ | H | H | H |
| 1-60 | $C_6H_5$ | Cl | H | H | Me |
| 1-61 | $C_6H_5$ | Cl | H | H | H |
| 1-62 | $C_6H_5$ | Me | H | H | H |
| 1-63 | $C_6H_5$ | $C_6H_5$ | H | H | Me |
| 1-64 | $C_6H_5$ | $C_6H_5$ | H | H | H |
| 1-65 | $C_6H_5$ | CHO | H | H | Et |
| 1-66 | $C_6H_5$ | $NO_2$ | H | H | H |
| 1-67 | $C_6H_5$ | CN | H | H | H |
| 1-68 | $C_6H_5$ | $CH_2CH_2CN$ | H | H | H |
| 1-69 | $C_6H_5$ | $CH=CMe_2$ | H | H | H |
| 1-70 | $C_6H_5CH_2$ | H | H | H | H |
| 1-71 | $CF_3$ | H | H | H | Et |
| 1-72 | $CF_3$ | H | H | H | H |
| 1-73 | Cl | H | H | H | Et |
| 1-74 | Cl | Cl | H | H | Et |
| 1-75 | OMe | H | H | H | Et |
| 1-76 | OMe | H | H | H | H |
| 1-77 | SMe | H | H | H | H |
| 1-78 | H | OMe | H | H | H |
| 1-79 | 2-thienyl | H | H | H | Et |
| 1-80 | 2-thienyl | H | H | H | H |
| 1-81 | $C_6H_5$ | H | 5-Me | H | Me |
| 1-82 | $C_6H_5$ | H | 5-Me | H | H |
| 1-83 | $C_6H_5$ | H | 5-Me | 7-Me | Et |
| 1-84 | $C_6H_5$ | H | 5-Me | 7-Me | H |
| 1-85 | $C_6H_5OCH_2$ | H | H | H | Me |
| 1-86 | $C_6H_5OCH_2$ | H | H | H | H |
| 1-87 | $C_6H_5SCH_2$ | H | H | H | Et |
| 1-88 | $C_6H_5SCH_2$ | H | H | H | H |
| 1-89 | $CH_2Cl$ | H | H | H | Et |
| 1-90 | $CH_2Cl$ | H | H | H | H |
| 1-91 | $C_6H_5OCH_2$ | $CH_2NMe_2$ | H | H | Et |
| 1-92 | $CH_2OMe$ | H | H | H | Et |
| 1-93 | $CH_2SMe$ | H | H | H | Me |
| 1-94 | $CH_2SMe$ | H | H | H | H |
| 1-95 | 4-$NO_2C_6H_4$ | $NO_2$ | H | H | Et |
| 1-96 | 4-$NO_2C_6H_4$ | $NO_2$ | H | H | H |
| 1-97 | 2,4-$(NO_2)_2C_6H_3$ | $NO_2$ | H | H | H |
| 1-98 | 2-thiazolyl | H | H | H | H |
| 1-99 | 4-Me,3-$NO_2C_6H_3$ | $NO_2$ | H | H | H |
| 1-100 | 2-Me,4-$tBuC_6H_3$ | H | H | H | Et |
| 1-101 | 2-Me,4-$tBuC_6H_3$ | H | H | H | H |
| 1-102 | 2-Me,5-$tBuC_6H_3$ | H | H | H | Et |
| 1-103 | 2-Me,5-$tBuC_6H_3$ | H | H | H | H |
| 1-104 | 2,4-$Me_2C_6H_3$ | H | H | H | H |
| 1-105 | 3,4-$Me_2C_6H_3$ | H | H | H | H |
| 1-106 | 2,3,4,5-$Me_4C_6H$ | H | H | H | Et |
| 1-107 | 2,3,4,5-$Me_4C_6H$ | H | H | H | H |
| 1-108 | 2,5-$Et_2C_6H_3$ | H | H | H | Et |
| 1-109 | 2,5-$Et_2C_6H_3$ | H | H | H | H |
| 1-110 | 4-$EtC_6H_4$ | H | H | H | H |
| 1-111 | 4-$EtC_6H_4$ | H | H | H | Et |
| 1-112 | 2,5-$Cl_2C_6H_3$ | H | H | H | H |
| 1-113 | 2,5-$(MeO)_2C_6H_3$ | H | H | H | H |
| 1-114 | 2-OMe,5-$ClC_6H_3$ | H | H | H | H |
| 1-115 | 2-OMe,5-$MeC_6H_3$ | H | H | H | H |
| 1-116 | 2-SMe,5-t-$BuC_6H_3$ | H | H | H | H |
| 1-117 | 2-SMe,5-$MeC_6H_3$ | H | H | H | H |
| 1-118 | 2-Me,4-$MeSC_6H_3$ | H | H | H | Et |
| 1-119 | $C_6H_5$ | CHO | H | H | Et |

TABLE 4-continued

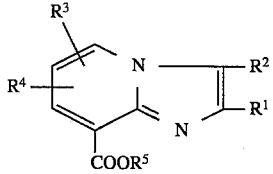

| Compound No. | R¹ | R² | R³ | R⁴ | R⁵ |
| --- | --- | --- | --- | --- | --- |
| 1-120 | C₆H₅ | CHO | H | H | H |
| 1-121 | C₆H₅ | CN | H | H | Et |
| 1-122 | C₆H₅ | CN | H | H | H |
| 1-123 | COOEt | H | H | H | Et |
| 1-124 | COOEt | NO₂ | H | H | H |
| 1-125 | H | NO₂ | H | H | H |
| 1-126 | 4-SO₃HC₆H₄ | H | H | H | H |
| 1-127 | Me | SO₃H | H | H | Et |
| 1-128 | Me | SO₃H | H | H | H |
| 1-129 | Me | SO₂NHMe | H | H | Et |
| 1-130 | Me | SO₂NHMe | H | H | H |
| 1-131 | Me | SO₂Cl | H | H | Et |
| 1-132 | OH | COOEt | H | H | Et |
| 1-133 | Cl | COOEt | H | H | Et |
| 1-134 | Cl | COOH | H | H | H |
| 1-135 | Cl | H | H | H | H |
| 1-136 | Me | NH₂ | H | H | Et |
| 1-137 | Me | C₆H₅CH=N | H | H | H |
| 1-138 | C₆H₅O | H | H | H | H |
| 1-139 | 2-FC₆H₄ | H | H | H | Et |
| 1-140 | 4-FC₆H₄ | H | H | H | Et |
| 1-141 | 4-FC₆H₄ | H | H | H | H |
| 1-142 | 2,4-F₂C₆H₃ | H | H | H | Et |
| 1-143 | 2,4-F₂C₆H₃ | H | H | H | H |
| 1-144 | 2,6-F₂C₆H₃ | H | H | H | Et |
| 1-145 | 2,6-F₂C₆H₃ | H | H | H | H |
| 1-146 | Me | NO₂ | H | H | Et |
| 1-147 | 2-thiazolyl | H | H | H | Et |
| 1-148 | 2-SMe,5-MeC₆H₃ | H | H | H | H |
| 1-149 | 2-Me,4-MeSC₆H₃ | H | H | H | Et |
| 1-150 | 4-FC₆H₄ | H | H | H | H |
| 1-151 | 2,4-(i-Pr)₂C₆H₃ | H | H | H | Et |
| 1-152 | 2,4-(i-Pr)₂C₆H₃ | H | H | H | H |
| 1-153 | 2-phenyl-imidazo[1,2-b]pyridazine-8-carboxylic acid | | | | |
| 1-154 | 6-chloro-2-phenyl-imidazo[1,2-b]-pyidazine-8-carboxylic acid | | | | |

TABLE 5

| Compound No. | m.p. (°C.) | NMR (δ value) |
| --- | --- | --- |
| 1-1 | 67~68 | 4.13(3H, s), 6.90(1H, t, J=6.75Hz), 7.70(1H, d, J=0.9Hz), 7.80(1H, d, J=0.9Hz), 8.37(1H, dd, J=6.75Hz, 1.2Hz). (CDCl₃) |
| 1-2 | 210 (decomp.) | 7.70(1H, d, J=7.5Hz), 8.20(1H, d, J=1.5Hz), 8.55(1H, d, J=7.5Hz), 8.65(1H, d, J=1.5Hz), 9.32(1H, d, J=7.5Hz). (DMSOd₆) |
| 1-3 | oil | 2.45(3H, s), 4.03(3H, s), 6.82(1H, t, J=6.75Hz), 7.45(1H, s), 7.95(1H, d, J=6.75Hz), 8.25(1H, d, J=6.75Hz). (CDCl₃) |
| 1-4 | | 2.50(3H, s), 7.45(1H, t, J=6.75Hz), 8.15(1H, s), 8.25(1H, d, J=6.75Hz), 9.00(1H, d, J=6.75Hz). (DMSOd₆) |
| 1-5 | 132~134 (HBr salt) | 1.32(3H, t, J=7.0Hz), 2.95(2H, q, J=7.0Hz), 4.05(3H, s), 7.60(1H, d, J=7.5Hz), 8.35(1H, s), 8.50(1H, d, J=6.75Hz), 9.25(1H, d, J=6.75Hz). (DMSOd₆) |
| 1-6 | 125~127 | 1.38(3H, t, J=7.5Hz), 3.00(2H, q, J=7.5Hz), 7.62(1H, t, J=6.75Hz), 8.50 (1H, d, J=6.75Hz), 8.55(1H, s), 9.45(1H, d, J=6.75Hz). (DMSOd₆) |
| 1-8 | oil | 1.40(6H, d, J=7.5Hz), 3.00–3.50(1H, m), 4.00(3H, s), 6.75(1H, t, J=6.75Hz), 7.45(1H, s), 7.90(1H, d, J=6.75Hz), 8.26(1H, d, J=6.75Hz, 1.5Hz). (DMSOd₆) |
| 1-9 | 135~137 | 1.30(6H, d, J=7.5Hz), 3.00–3.60(1H, m), 7.07(1H, t, J=6.75Hz), 7.85(1H, s), 7.99(1H, d, J=6.75Hz), 8.75(1H, d, J=6.75Hz). (DMSOd₆) |
| 1-11 | 157~158 (HBr salt) | 1.48(9H, s), 4.03(3H, s), 7.58(1H, t, J=6.75Hz), 8.33(1H, s), 8.45(1H, d, J=6.75Hz), 9.12(1H, t, J=6.75Hz). (DMSOd₆) |
| 1-12 | 228 | 1.50(9H, s), 7.69(1H, t, J=6.3Hz), 8.40–8.60(2H, m), 9.26(1H, d, J=6.3Hz). (DMSOd₆) |
| 1-13 | oil | 1.45(3H, t, J=6.0Hz), 4.55(2H, q, J=6.0Hz), 7.05(1H, t, J=6.75Hz), 7.70 (1H, s), 8.00(1H, d, J=6.75Hz), 8.28 (1H, d, J=6.75Hz). (CDCl₃) |
| 1-14 | | 7.56(1H, t, J=6.75Hz), 8.20(1H, s), 8.38(1H, d, J=6.75Hz), 8.90(1H, d, J=6.75Hz). (DMSOd₆) |
| 1-15 | oil | 2.50(3H, s), 4.05(3H, s), 6.95(1H, t, J=6.75Hz), 8.00(1H, d, J=6.75Hz), 9.00(1H, d, J=6.75Hz). (CDCl₃) |
| 1-17 | 123~124 | 2.20(6H, s), 2.50(3H, s), 3.65(2H, s), 6.73(1H, t, J=6.75Hz), 7.95(1H, d, J=6.75Hz), 8.42(1H, d, J=6.75Hz). (CDCl₃) |
| 1-22 | 255 (sublimed) | 3.20(3H, s), 8.04(1H, t, J=6.75Hz), 9.09(1H, d, J=6.75Hz), 10.04(1H, d, J=6.75Hz). (CF₃COOD) |
| 1-24 | oil | 4.05(3H, s), 6.83(1H, t, J=7.5Hz), 7.35–7.60(3H, m), 7.95(1H, s), 7.98–8.15(3H, m), 8.30(1H, d, J=7.5Hz). (CDCl₃) |
| 1-26 | 226 | 7.40–7.70(4H, m), 7.95–8.10(2H, m), 8.33(1H, d, J=6.75Hz), 8.80(1H, s), 9.10(1H, d, J=6.75Hz). (DMSOd₆) |
| 1-27 | oil | 2.60(3H, s), 4.05(3H, s), 6.88(1H, t, J=6.75Hz), 7.25–7.40(3H, m), 7.80 (1H, s), 7.90–8.10(1H, m), 8.35(1H, d, J=6.75Hz). (CDCl₃) |
| 1-28 | 220 (sublimed) | 2.38(3H, s), 7.30–7.80(5H, m), 8.50 (1H, J=6.75Hz), 8.75(1H, s), 9.28(1H, d, J=6.75Hz). (DMSOd₆) |
| 1-30 | | 2.48(3H, s), 4.03(3H, s), 7.30–7.90(5H, m), 8.42(1H, d, J=6.75Hz), 8.87(1H, s), 9.15(1H, d, J=6.75Hz). (DMSOd₆) |
| 1-31 | 225~227 | 2.40(3H, s), 7.10–7.50(3H, m), 7.70–7.90(2H, m), 8.10(1H, d, J=6.75Hz), 8.65(1H, s), 8.90(1H, d, J=6.75Hz). (DMSOd₆) |
| 1-32 | 122~124 | 2.35(3H, s), 4.06(3H, s), 6.80(1H, d, J=6.75Hz), 7.25(2H, d, J=8.25Hz), 7.85–8.05(3H, m), 7.90(1H, s), 8.28 (1H, dd, J=6.75Hz, 1.5Hz). (DMSOd₆) |
| 1-33 | 178~180 | 2.38(3H, s), 7.30–7.50(3H, m), 7.85 (2H, d, J=8.25Hz), 8.25(1H, d, J=6.75Hz), 8.70(1H, s), 9.04(1H, d, J=6.75Hz). (DMSOd₆) |
| 1-34 | 233~235 | 2.33(3H, s), 2.48(3H, s), 7.02–7.30(2H, m), 7.67(1H, m), 8.02(1H, dd, J=7.5Hz, 1.5Hz), 8.37(1H, s), 8.85 (1H, dd, J=7.5Hz, 1.5Hz). (DMSOd₆) |
| 1-36 | (HBr salt) | 4.00(3H, s), 4.08(3H, s), 7.10–7.40(2H, m), 7.50–7.80(2H, m), 7.93(1H, dd, J=1.5Hz, 7.5Hz), 8.54(1H, d, J=6.75Hz), 8.95(1H, s), 9.34(1H, d, J=6.75Hz). (DMSOd₆) |
| 1-37 | 238~240 | 4.00(3H, s), 7.00–7.60(4H, m), 8.05 |

TABLE 5-continued

| Compound No. | m.p. (°C.) | NMR (δ value) |
|---|---|---|
| | | (1H, dd, J=1.5Hz, 7.5Hz), 8.27(1H, d, J=6.75Hz), 8.75(1H, s), 9.10(1H, d, J=6.75Hz). (DMSOd$_6$) |
| 1-38 | 172~174 (HBr salt) | 4.00(3H, s), 4.17(3H, s), 7.20(1H, m), 7.50-7.80(4H, m), 8.54(1H, d, J=6.75Hz), 8.99(1H, s), 9.25(1H, d, J=6.75Hz). (DMSOd$_6$) |
| 1-39 | 209~211 | 3.90(3H, s), 7.10(1H, m), 7.30-7.75 (4H, m), 8.48(1H, d, J=6.75Hz), 9.00 (1H, s), 9.25(1H, d, J=6.75Hz). (DMSOd$_6$) |
| 1-40 | oil | 3.84(3H, s), 4.05(3H, s), 6.83(1H, d, J=6.75Hz), 7.00(3H, d, J=8.25Hz), 7.80-8.10(4H, m), 8.25(1H, dd, J=6.75Hz, 1.5Hz). (CDCl$_3$) |
| 1-41 | 171~173 | 3.78(3H, s), 7.05(1H, d, J=8.25Hz), 7.30(3H, t, J=6.75Hz), 7.88(2H, d, J=6.75Hz), 8.60 (1H, s), 8.98(1H, d, J=6.75Hz). (DMSOd$_6$) |
| 1-42 | 224~225 (HBr salt) | 1.43(3H, t, J=6.6Hz), 3.88(3H, s), 3.90(3H, s) 4.47(2H, q, J=6.6Hz), 7.15(1H, d, J=9.0Hz), 7.48-7.68(2H, m), 8.42(1H, dd, J=7.5Hz, 1.5Hz), 8.88(1H, s) 9.12(1H, d, J=7.5Hz). (DMSOd$_6$) |
| 1-43 | 243~245 | 3.85(3H, s), 3.90(3H, s), 7.10(1H, d, J=9.0Hz), 7.40-7.78(2H, m), 8.35(1H, d, J=7.5Hz), 8.83(1H, s), 9.10(1H, d, J=7.5Hz). (DMSOd$_6$) |
| 1-45 | 205 (sublimed) | 7.25(1H, t, J=6.3Hz), 7.40-7.60(3H, m), 8.00-8.30(2H, m), 8.84(1H, s), 9.00 (1H, d, J=6.75Hz). (DMSOd$_6$) |
| 1-46 | 220 (sublimed) (HBr salt) | 4.05(3H, s), 7.50-7.80(3H, m), 7.95 (1H, s), 8.10(1H, br), 8.45(1H, d, J=6.75Hz) 8.96(1H, s), 9.15(1H, d, J=6.75Hz). (DMSOd$_6$) |
| 1-47 | 225 (sublimed) | 7.40-7.60(3H, m), 7.95(1H, m), 8.15 (1H, br), 8.35(1H, d, J=6.75Hz), 8.92 (1H, s), 9.11(1H, d, J=6.75Hz), (DMSOd$_6$) |
| 1-48 | 132~133 | 4.05(3H, s), 6.85(1H, t, J=6.7Hz), 7.45(2H, d, J=8.3Hz), 7.90(1H, s), 7.80-8.10(3H, m), 8.30(1H, dd, J=6.75Hz, 1.5Hz). (CDCl$_3$) |
| 1-49 | 220~222 | 7.50-7.70(3H, m), 8.05(2H, d, J=8.3Hz), 8.50(1H, d, J=6.75Hz), 8.85(1H, s), 9.15(1H, d, J=6.75Hz). (DMSOd$_6$) |
| 1-50 | 160~162 (HBr salt) | 4.20(3H, s), 7.60-8.00(5H, m), 8.60-8.80(2H, m), 9.10(1H, d, J=7.78Hz). (DMSOd$_6$) |
| 1-51 | 205 (sublimed) | 7.41(1H, t, J=6.75Hz), 7.68(2H, d, J=8.25Hz), 7.94(2H, d, J=8.25Hz), 8.23(1H, d, J=6.75Hz), 8.85(1H, s), 9.08(1H, d, J=6.75Hz). (DMSOd$_6$) |
| 1-52 | 157~158 | 4.00(3H, s), 7.08(1H, t, J=6.75Hz), 7.96(1H, d, J=6.75Hz), 8.35(4H, s) 8.78(1H, s), 8.85(1H, d, J=6.75Hz). (DMSOd$_6$) |
| 1-53 | 240 (sublimed) | 7.28(1H, t, J=6.75Hz), 8.20(1H, d, J=6.75Hz), 8.30-8.50(4H, m), 8.82 (1H, s), 8.95(1H, d, J=6.75Hz). (DMSOd$_6$) |
| 1-54 | 266 | 7.20(1H, t, J=6.75Hz), 7.25-7.55(3H, m), 8.10(1H, d, J=6.75Hz), 8.18-8.40 (1H, m), 8.54(1H, d, J=4.5Hz), 8.95 (1H, d, J=6.75Hz). (DMSOd$_6$) |
| 1-56 | 199~201 | 2.48(6H, m), 7.15-7.70(4H, m), 8.32 (1H, d, J=6.75Hz), 8.55(1H, s), 9.04 (1H, d, J=6.75Hz). (DMSOd$_6$) |
| 1-60 | 97~98 | 4.18(3H, s), 6.99(1H, t, J=6.9Hz), 7.25-7.63(3H, m), 7.93-8.38(4H, m). (CDCl$_3$) |
| 1-61 | 194~196 | 7.26(1H, t, J=7.25Hz), 7.92-8.25(3H, m), 8.64(1H, dd, J=1.5Hz, 7.2Hz). (DMSOd$_6$) |
| 1-63 | 129~131 | 4.08(3H, s), 6.80(3H, t, J=6.3Hz), 7.21-7.35(3H, m), 7.35-7.62(4H, m), 7.65-7.82(3H, m), 7.98(1H, d, J=6.3Hz), 8.08(1H, d, J=6.3Hz). (CDCl$_3$) |
| 1-71 | oil | 1.43(3H, t, J=6.0Hz), 4.48(2H, q, J=6.0Hz), 7.00(1H, t, J=6.3Hz), 8.01 (1H, dd, J=7.5Hz, 0.8Hz), 8.42(1H, dd, J=7.5Hz, 0.8Hz), 8.00-8.10(1H, m). (CDCl$_3$) |
| 1-72 | 203~205 | 7.20(1H, t, J=6.0Hz), 8.55(1H, dd, J=9.0Hz, 1.5Hz), 8.60-8.67(1H, m), 8.83(1H, dd, J=9.0Hz, 1.5Hz). (DMSOd$_6$) |
| 1-79 | 89~91 | 6.71-6.70(2H, m), 6.70-6.95(2H, m), 7.21-7.35(3H, m), 7.35-7.62(4H, m), 7.65-7.82(3H, m), 8.08(1H, d, J=6.3Hz). (DMSOd$_6$) |
| 1-81 | 250 (sublimed) (HBr salt) | 2.50(3H, s), 4.05(3H, s), 7.48-7.70(3H, m), 7.88-8.08(2H, m), 8.40(1H, d, J=1.0Hz), 8.80(1H, s), 9.02(1H, d, J=1.0Hz). (DMSOd$_6$) |
| 1-82 | 250~252 | 2.40(3H, s), 7.39-7.65(3H, m), 7.95-8.10(2H, m), 8.09(1H, d, J=1.5Hz), 8.50(1H, s), 8.78(1H, d, J=1.5Hz). (DMSOd$_6$) |
| 1-83 | 157~158 | 1.50(3H, t, J=6.3Hz), 2.41(3H, s), 2.55(3H, s), 4.58(2H, q, J=6.3Hz), 6.42(1H, s), 7.20-7.50(4H, m), 7.65(1H, s), 7.85-8.10(2H, m). (CDCl$_3$) |
| 1-84 | 121~122 | 2.68(3H, s), 2.71(3H, s), 7.05(1H, s), 7.40-7.70(4H, m), 8.60(1H, s). (DMSOd$_6$) |
| 1-85 | | 2.18(3H, s), 3.94(2H, s), 4.02(3H, s), 6.81(1H, t, J=6.6Hz), 7.68(1H, s), 7.93(1H, dd, J=6.6Hz, 1.5Hz), 8.28(1H, dd, J=6.6Hz, 1.5Hz). (DMSOd$_6$) |
| 1-86 | 250 (sublimed) | 5.38(2H, s), 6.88-7.20(3H, m), 7.21-7.55(3H, m), 8.27(1H, d, J=7.5Hz), 8.42(1H, s), 9.05(1H, d, J=7.5Hz). (DMSOd$_6$) |
| 1-88 | 255 (sublimed) | 4.48(2H, s), 7.15-7.55(6H, m), 8.13 (1H, s), 8.10(1H, d, J=6.6Hz), 8.89 (1H, d, J=6.6Hz). (DMSOd$_6$) |
| 1-89 | 138~139 | 1.42(3H, t, J=6.3Hz), 4.47(2H, q, J=6.3Hz), 4.86(2H, s), 6.87(1H, t, J=7.5Hz), 7.72(1H, s), 7.93(1H, dd, J=7.5Hz, 1.5Hz). 8.28(1H, dd, J=7.5Hz, 1.5Hz). (CDCl$_3$) |
| 1-90 | 250 (decomp.) | 4.86(2H, s), 6.87(1H, t, J=7.5Hz), 7.72(1H, s), 7.93(1H, dd, J=7.5Hz, 1.5Hz), 8.28(1H, dd, J=7.5Hz, 1.5Hz). (CDCl$_3$) |
| 1-94 | oil | 2.18(3H, s), 3.94(2H, s), 4.02(3H, s), 6.81(1H, t, J=6.6Hz), 7.68(1H, s), 7.93(1H, dd, J=6.6Hz, 1.5Hz), 8.28 (1H, dd, J=6.6Hz, 1.5Hz). (CDCl$_3$) |
| 1-96 | more than 300 | 7.60(1H, t, J=7.8Hz), 8.04-8.52(5H, m), 9.56-9.72(1H, m). (DMSOd$_6$) |
| 1-98 | 210 (sublimed) | 7.22(1H, t, J=6.75Hz), 7.83(1H, d, J=3.0Hz), 8.00(1H, d, J=3.0Hz), 8.05 (1H, d, J=6.75Hz), 8.67(1H, s), 8.92 (1H, d, J=6.75Hz). (DMSOd$_6$) |
| 1-100 | oil | 1.32(9H, s), 1.45(3H, t, J=7.0Hz), 2.60(3H, s), 4.52(2H, q, J=7.0Hz), 6.75(1H, t, J=6.75Hz), 7.20-7.40(2H, m), 7.70-8.00(3H, m), 8.33(1H, d, J=6.75Hz) (CDCl$_3$) |
| 1-101 | 191~192 | 1.30(9H, s), 2.56(3H, s), 7.20(1H, t, J=6.75Hz), 7.36(2H, m), 7.82(1H, d, J=9.0Hz), 8.40(1H, s), 8.94(1H, d, J=6.75Hz). (DMSOd$_6$) |
| 1-102 | oil | 1.35(9H, s), 1.50(3H, t, J=7.0Hz), 2.51(3H, s), 4.51(2H, q, J=7.0Hz), |

TABLE 5-continued

| Compound No. | m.p. (°C.) | NMR (δ value) |
|---|---|---|
| | | 6.78(1H, t, J=6.75Hz), 7.05–7.40(2H, m), 7.76(1H, s), 7.90(1H, d, J=6.75Hz), 8.05(1H, m), 8.32(1H, d, J=6.75Hz). (CDCl$_3$) |
| 1-103 | 194~195 | 1.32(9H, s), 2.45(3H, s), 7.15(1H, t, J=6.75Hz), 7.30(2H, m), 7.85(1H, m), 8.08(1H, d, J=6.75Hz), 8.45(1H, s), 8.90(1H, d, J=6.75Hz). (DMSOd$_6$) |
| 1-104 | 240~241 | 2.37(3H, s), 2.45(3H, s), 7.17(1H, d, J=7.5Hz), 7.23(1H, S), 7.60(1H, d, J=5.6Hz), 7.45(1H, t, J=6.5Hz), 8.28(1H, dd, J=6.6, 1.5Hz), 8.52(1H, s), 9.05(1H, dd, J=6.6, 1.5Hz). (DMSOd$_6$) |
| 1-105 | 249~250 | 2.30(3H, s), 2.34(3H, s), 7.31(1H, d, J=6.6Hz), 7.42(1H, d, J=7.5Hz), 7.72(1H, dd, J=7.5Hz, 1.5Hz), 7.77(1H, d, J=1.5Hz), 8.28(1H, dd, J=6.6, 1.5Hz), 8.70(1H, s), 9.03(1H, dd, J=6.6, 1.5Hz). (DMSOd$_6$) |
| 1-106 | 211~212 (HBr salt) | 1.45(3H, t, J=7.0Hz), 2.20–2.45(12H, br), 4.55(2H, q, J=7.0Hz). 7.19(1H, s), 7.63(1H, d, J=6.75Hz), 8.52(1H, d, J=6.75Hz), 8.52(1H, d, J=6.75Hz), 8.59(1H, s), 9.33(1H, d, J=6.75Hz). (DMSOd$_6$) |
| 1-107 | 265~266 | 2.20–2.45(12H, m), 7.15(1H, s), 7.67(1H, d, J=6.75Hz), 8.45–8.60(2H, m), 9.29(1H, d, J=6.75Hz). (DMSOd$_6$) |
| 1-110 | 212~213 (HBr salt) | 1.28(3H, t, J=7.0Hz), 1.48(3H, t, J=7.0Hz), 2.74(2H, q, J=7.0Hz), 4.57(2H, q, J=7.0Hz), 7.43(2H, d, J=7.5Hz), 7.64(1H, t, J=6.75Hz), 7.95(2H, d, J=7.5Hz), 8.53(1H, d, J=6.75Hz), 8.88(1H, s), 9.25(1H, d, J=6.75Hz). (DMSOd$_6$) |
| 1-111 | 214~215 | 1.25(3H, t, J=7.0Hz), 2.75(2H, q, J=7.0Hz), 7.25–7.60(3H, m), 7.91(2H, d, J=7.5Hz), 8.33(1H, d, J=6.75Hz), 8.79(1H, s), 9.10(1H, d, J=6.75Hz). (DMSOd$_6$) |
| 1-112 | 260 (sublimed) | 2.35(3H, s), 3.98(3H, s), 7.15(1H, t, J=7.5Hz), 7.30(1H, dd, J=8.0, 1.5Hz), 7.45(1H, d, J=1.5Hz), 7.87(1H, d, J=1.5Hz), 8.25(1H, d, J=7.5Hz), 8.73(1H, s), 9.05(1H, d, J=7.5Hz). (DMSOd$_6$) |
| 1-113 | 225 (sublimed) | 2.37(3H, s), 2.45(3H, s), 7.17(1H, d, J=7.5Hz), 7.23(1H, s), 7.60(1H, d, J=6.6Hz), 7.45(1H, t, J=6.6Hz), 8.28(1H, dd, J=6.6, 1.5Hz), 8.52(1H, s), 9.05(1H, dd, J=6.6, 1.5Hz). (DMSOd$_6$) |
| 1-114 | 283~285 | 4.00(3H, s), 7.33(1H, t, J=6.6Hz), 7.49(1H, d, J=6.3Hz), 7.69(1H, dd, J=6.3, 2.5Hz), 8.12(1H, d, J=2.5Hz), 8.40(1H, d, J=6.3Hz), 8.89(1H, s), 9.16(1H, d, J=6.3Hz). (DMSOd$_6$) |
| 1-115 | 235~237 | 2.35(3H, s), 3.98(3H, s), 7.15(1H, t, J=7.5Hz), 7.30(1H, dd, J=8.0, 1.5Hz), 7.45(1H, d, J=1.5Hz), 7.87(1H, d, J=1.5Hz), 8.25(1H, d, J=7.5Hz), 8.73(1H, s), 9.05(1H, d, J=7.5Hz). (DMSOd$_6$) |
| 1-118 | 164~167 (HBr salt) | 1.45(3H, t, J=7.0Hz), 2.44(3H, s), 2.53(3H, s), 4.55(2H, q, J=7.0Hz), 7.15–7.40(2H, m), 7.50–7.75(2H, m), 8.47(1H, d, J=6.75Hz), 8.64(1H, s), 9.22(1H, d, J=6.75Hz). (DMSOd$_6$) |
| 1-119 | 139 | 1.48(3H, t, J=6.9Hz), 4.53(2H, q, J=6.9Hz), 7.20(1H, t, J=7.2Hz), 7.50–7.65(3H, m), 7.82–8.03(2H, m), 8.27(1H, dd, J=1.35, 7.2Hz), 9.90(1H, dd, J=1.35, 7.21Hz), 10.15(1H, s). (CDCl$_3$) |
| 1-120 | 214~216 | 7.35–7.70(4H, m), 7.88–8.09(2H, m), 8.32(1H, dd, J=1.35, 6.6Hz), 9.80(1H, dd, J=1.35, 6.6Hz), 10.12(1H, s). (DMSOd$_6$) |
| 1-121 | 87~89 | 1.49(3H, t, J=7.5Hz), 4.52(2H, q, J=7.5Hz), 6.99(1H, s), 7.21(1H, t, J=7.35Hz), 7.36–7.69(3H, m), 8.01(1H, dd, J=7.35, 7.35Hz), 8.17–8.49(3H, m). (CDCl$_3$) |
| 1-122 | 200~201 | 7.28(1H, t, J=6.9Hz), 7.40–7.70(3H, m), 8.00–8.23(3H, m), 8.68(1H, dd, J=1.35, 6.9Hz). (DMSOd$_6$) |
| 1-123 | 97 | 1.43(3H, t, J=3.9Hz), 1.45(3H, t, J=3.9Hz), 4.03–4.68(4H, m), 6.99(1H, t, J=6.9Hz), 7.94–8.12(1H, m), 8.30(1H, s), 8.40(1H, d, J=6.9Hz). (CDCl$_3$) |
| 1-124 | 139~140 | 1.39(6H, t, J=7.8Hz), 4.45(2H, q, J=7.8Hz), 4.48(2H, q, J=7.8Hz), 7.63(1H, t, J=7.65Hz), 8.37(1H, dd, J=1.35, 7.65Hz), 9.52(1H, dd, J=1.35, 7.65Hz). (DMSOd$_6$) |
| 1-125 | >300 | 7.57(1H, t, J=7.5Hz), 8.30(1H, dd, J=1.35, 7.5Hz), 8.80(1H, s), 9.55(1H, dd, J=1.35, 7.5Hz). (DMSOd$_6$) |
| 1-127 | 247~250 (decomp.) | 1.40(3H, t, J=7.5Hz), 2.71(3H, s), 2.90–4.24(1H, br), 4.51(2H, q, J=7.5 Hz), 7.72(1H, t, J=7.8Hz), 8.57(1H, dd, J=1.35, 7.8Hz), 9.30(1H, dd, J=1.35, 7.8Hz). (DMSOd$_6$) |
| 1-128 | >300 | 2.71(3H, s), 7.70(1H, t, J=7.5Hz), 8.52(1H, dd, J=1.35, 7.5Hz), 9.30(1H, dd, J=1.35, 7.5Hz). (DMSOd$_6$) |
| 1-129 | 184~185 | 1.42(3H, t, J=7.5Hz), 2.65(3H, s), 2.77(3H, s), 4.47(2H, q, J=7.5Hz), 5.25(1H, br), 7.03(1H, t, J=7.5Hz), 8.11(1H, dd, J=1.35, 7.5Hz) 8.87(1H, dd, J=1.35, 7.5Hz). (CDCl$_3$) |
| 1-130 | 235~236 | 2.49(3H, d, J=5.4Hz), 2.70(3H, s), 5.40–6.90(1H, br), 7.60(1H, t, J=6.6Hz), 8.34–8.74(2H, m), 9.02–9.20(1H, m), (DMSOd$_6$) |
| 1-131 | 182~183 | 1.47(3H, t, J=7.5Hz), 2.85(3H, s), 4.53(2H, q, J=7.5Hz), 7.30(1H, t, J=7.1Hz), 8.28(1H, dd, J=1.5, 7.1Hz), 8.98(1H, dd, J=1.5, 7.1Hz). (CDCl$_3$) |
| 1-132 | (HBr salt) | 1.20–1.49(6H, m), 4.12–4.60(4H, m), 7.20–7.42(1H, m), 8.11(1H, dd, J=1.35, 7.8Hz), 9.67(1H, dd, J=1.35, 7.2Hz). (DMSOd$_6$) |
| 1-133 | 105~106 | 1.44(6H, t, J=7.5Hz), 4.31–4.66(4H, m), 7.15(1H, t, J=7.5Hz), 8.17(1H, dd, J=1.35, 7.5Hz), 9.57(1H, dd, J=1.35, 7.5Hz). (CDCl$_3$) |
| 1-134 | 210–212 (decomp.) | 5.40–8.00(2H, br), 7.38(1H, t, J=6.6Hz), 8.18(1H, dd, J=1.35, 6.6Hz), 9.55(1H, dd, J=1.35, 6.6Hz). (DMSOd$_6$) |
| 1-135 | 237 | 7.25(1H, t, J=7.5Hz), 8.19(1H, dd, J=1.35, 7.5Hz), 7.65–8.29(1H, br), 8.35(1H, s), 8.88(1H, dd, J=1.35, 7.5Hz). (DMSOd$_6$) |
| 1-136 | amorphous | 1.42(3H, t, J=7.2Hz), 2.43(3H, s), 2.91(2H, br), 4.47(2H, q, J=7.2Hz), 6.81(1H, t, J=7.5Hz), 7.82(1H, dd, J=1.35, 7.5Hz), 8.20(1H, dd, J=1.35, 7.5Hz). (CDCl$_3$) |
| 1-137 | 231~233 | 2.70(3H, s), 7.20(3H, t, J=6.9Hz), 7.47–7.68(3H, m), 7.93–8.21(3H, m), 8.76–8.95(2H, m). (DMSOd$_6$) |
| 1-139 | 270 (decomp.) (HBr salt) | 1.42(3H, t, J=7.0Hz), 4.54(2H, q, J=7.0Hz), 7.30–7.70(4H, m), 8.00–8.25(1H, m), 8.39(1H, d, J=6.75Hz), 8.77(1H, d, J=4.5Hz), 9.20(1H, d, J=6.75Hz). (DMSOd$_6$) |
| 1-140 | 177~178 | 1.42(3H, t, J=7.0Hz), 4.55(2H, q, |

TABLE 5-continued

| Compound No. | m.p. (°C.) | NMR (δ value) |
|---|---|---|
| | (HBr salt) | J=7.0Hz), 7.40(2H, t, J=9.0Hz), 7.62(1H, t, J=6.75Hz), 8.03(2H, dd, J=9.0, 6.0Hz), 8.48(1H, d, J=6.75Hz), 8.88(1H, s), 9.20(1H, d, J=6.75Hz). (DMSOd$_6$) |
| 1-141 | 220 (sublimed) | 7.20–7.50(3H, m), 8.05(2H, dd, J=9.0, 6.0Hz), 8.28(1H, d, J=6.75Hz), 8.73 (1H, s), 9.06(1H, d, J=6.75Hz). (DMSOd$_6$) |
| 1-142 | 97–99 | 1.50(3H, t, J=7.0Hz), 4.65(2H, q, J=7.0Hz), 6.80–7.20(3H, m), 7.90(1H, d, J=6.75Hz), 8.06(1H, d, J=4.0Hz), 8.34(1H, d, J=6.75Hz), 8.45–8.65(1H, m) (CDCl$_3$) |
| 1-143 | 240 (sublimed) | 7.00–7.40(2H, m), 7.65–8.10(2H, m), 8.56(1H, s), 8.85(1H, d, J=6.75Hz), 9.01(1H, d, J=6.75Hz). (CF$_3$COOD) |
| 1-144 | 206–208 (HBr salt) | 1.41(3H, t, J=7.0Hz), 4.55(2H, q, J=7.0Hz), 7.20–7.90(4H, m), 8.55(1H, d, J=6.75Hz), 8.88(1H, s), 8.32(1H, d, J=6.75Hz). (DMSOd$_6$) |
| 1-145 | 280–282 | 7.15–7.80(3H, m), 8.12(1H, d, J=6.75Hz), 8.55(1H, d, J=1.5Hz), 8.99(1H, d, J=6.75Hz). (DMSOd$_6$) |
| 1-146 | 143–144 | 1.45(3H, t, J=7.0Hz), 2.78(3H, s), 4.42(2H, q, J=7.0Hz), 7.50(1H, d, J=6.75Hz), 8.25(1H, d, J=6.75Hz), 9.55(1H, d, J=6.75Hz). (DMSOd$_6$) |
| 1-147 | 143–146 (HBr salt) | 1.38(3H, t, J=7.0Hz), 4.42(2H, q, J=7.0Hz), 7.30(1H, m), 8.88(2H, m), 8.30(1H, m), 8.70(2H, m). (DMSOd$_6$) |
| 1-151 | oil | 1.30(12H, d, J=6.0Hz), 1.45(3H, t, J=7.0Hz), 2.95(1H, m, J=6.0Hz), 3.48(1H, m, J=6.0Hz), 4.45(2H, q, J=7.0Hz), 6.75–7.75(5H, m), 7.95(1H, d, J=6.75Hz), 8.35(1H, d, J=6.75Hz). (CDCl$_3$) |
| 1-152 | 99–101 | 1.15–1.40(12H, m), 2.80–3.40(2H, m), 7.10–7.60(4H, m), 8.35(1H, d, J=6.75Hz), 8.48(1H, s), 9.09(1H, d, J=6.75Hz). (DMSOd$_6$) |

TABLE 6

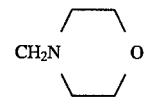

| Compound No. | R$^1$ | R$^2$ | R$^3$ | R$^4$ | R$^6$ |
|---|---|---|---|---|---|
| 2-1 | H | H | H | H | A-1 |
| 2-2 | Me | H | H | H | A-1 |
| 2-3 | Me | H | H | H | A-2 |
| 2-4 | Me | H | H | H | A-4 |
| 2-5 | Et | H | H | H | A-1 |
| 2-6 | nPr | H | H | H | A-1 |
| 2-7 | iPr | H | H | H | A-1 |
| 2-8 | nBu | H | H | H | A-1 |
| 2-9 | tBu | H | H | H | A-1 |
| 2-10 | H | Cl | H | H | A-1 |
| 2-11 | Me | Cl | H | H | A-1 |
| 2-12 | Me | Me | H | H | A-1 |
| 2-13 | Me | CHO | H | H | A-1 |
| 2-14 | Me | NO$_2$ | H | H | A-1 |
| 2-15 | Me | CH$_2$NMe$_2$ | H | H | A-1 |
| 2-16 | Me | CF$_2$CHF$_2$ | H | H | A-1 |
| 2-17 | Me | CH$_2$NMe$_2$ | H | H | A-2 |
| 2-18 | Me | CH$_2$NMe$_2$ | H | H | A-4 |
| 2-19 | Me | CH$_2$NMe$_2$·HCl* | H | H | A-4 |
| 2-20 | Me | CH$_2$N(morpholine) | H | H | A-1 |
| 2-21 | Me | CH$_2$S-iPr | H | H | A-4 |
| 2-22 | Me | CH$_2$CH$_2$CN | H | H | A-4 |
| 2-23 | Me | CH=CMe$_2$ | H | H | A-4 |
| 2-24 | C$_6$H$_5$ | H | H | H | A-1 |
| 2-25 | C$_6$H$_5$ | H | H | H | A-2 |
| 2-26 | C$_6$H$_5$ | H | H | H | A-3 |
| 2-27 | C$_6$H$_5$ | H | H | H | A-4 |
| 2-28 | C$_6$H$_5$ | H | H | H | A-5 |
| 2-29 | C$_6$H$_5$ | H | H | H | A-6 |
| 2-30 | C$_6$H$_5$ | H | H | H | A-7 |
| 2-31 | C$_6$H$_5$ | H | H | H | A-8 |
| 2-32 | C$_6$H$_5$ | H | H | H | A-9 |
| 2-33 | C$_6$H$_5$ | H | H | H | A-10 |
| 2-34 | C$_6$H$_5$ | H | H | H | A-11 |

TABLE 6-continued

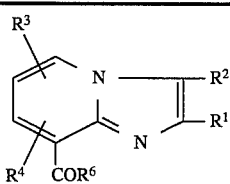

| Compound No. | R¹ | R² | R³ | R⁴ | R⁶ |
|---|---|---|---|---|---|
| 2-35 | $C_6H_5$ | H | H | H | A-12 |
| 2-36 | $C_6H_5$ | H | H | H | A-13 |
| 2-37 | $C_6H_5$ | H | H | H | A-14 |
| 2-38 | $C_6H_5$ | H | H | H | A-15 |
| 2-39 | $C_6H_5$ | H | H | H | A-16 |
| 2-40 | $C_6H_5$ | H | H | H | A-17 |
| 2-41 | $C_6H_5$ | H | H | H | A-18 |
| 2-42 | $C_6H_5$ | H | H | H | A-19 |
| 2-43 | $C_6H_5$ | H | H | H | A-20 |
| 2-44 | $C_6H_5$ | H | H | H | A-21 |
| 2-45 | $C_6H_5$ | H | H | H | A-22 |
| 2-46 | $C_6H_5$ | H | H | H | A-23 |
| 2-47 | $C_6H_5$ | H | H | H | A-24 |
| 2-48 | $C_6H_5$ | H | H | H | A-25 |
| 2-49 | $C_6H_5$ | H | H | H | A-26 |
| 2-50 | $C_6H_5$ | H | H | H | A-27 |
| 2-51 | $C_6H_5$ | H | H | H | A-28 |
| 2-52 | $C_6H_5$ | H | H | H | A-29 |
| 2-53 | $C_6H_5$ | H | H | H | A-30 |
| 2-54 | $2\text{-MeC}_6H_4$ | H | H | H | A-1 |
| 2-55 | $2\text{-MeC}_6H_4$ | H | H | H | A-2 |
| 2-56 | $2\text{-MeC}_6H_4$ | H | H | H | A-4 |
| 2-57 | $3\text{-MeC}_6H_4$ | H | H | H | A-1 |
| 2-58 | $4\text{-MeC}_6H_4$ | H | H | H | A-1 |
| 2-59 | $2,5\text{-Me}_2C_6H_3$ | H | H | H | A-1 |
| 2-60 | $2,5\text{-Me}_2C_6H_3$ | H | H | H | A-2 |
| 2-61 | $2,5\text{-Me}_2C_6H_3$ | H | H | H | A-4 |
| 2-62 | $2,4,6\text{-Me}_3C_6H_2$ | H | H | H | A-1 |
| 2-63 | $2\text{-MeOC}_6H_4$ | H | H | H | A-1 |
| 2-64 | $3\text{-MeOC}_6H_4$ | H | H | H | A-1 |
| 2-65 | $4\text{-MeOC}_6H_4$ | H | H | H | A-1 |
| 2-66 | $3,4\text{-(MeO)}_2C_6H_3$ | H | H | H | A-1 |
| 2-67 | $3,4\text{-(MeO)}_2C_6H_3$ | H | H | H | A-4 |
| 2-68 | $2\text{-ClC}_6H_4$ | H | H | H | A-1 |
| 2-69 | $3\text{-ClC}_6H_4$ | H | H | H | A-1 |
| 2-70 | $4\text{-ClC}_6H_4$ | H | H | H | A-1 |
| 2-71 | $4\text{-BrC}_6H_4$ | H | H | H | A-1 |
| 2-72 | $4\text{-NO}_2C_6H_4$ | H | H | H | A-1 |
| 2-73 | $2\text{-FC}_6H_4$ | H | H | H | A-1 |
| 2-74 | $2\text{-F,4-MeC}_6H_3$ | H | H | H | A-1 |
| 2-75 | $2\text{-Me,4-MeSC}_6H_3$ | H | H | H | A-4 |
| 2-76 | $2,4,6\text{-Cl}_3C_6H_2$ | H | H | H | A-1 |
| 2-77 | $C_6H_5$ | $CH_2NMe_2$ | H | H | A-1 |
| 2-78 | $C_6H_5$ | $CH_2NMe_2$ | H | H | A-2 |
| 2-79 | $C_6H_5$ | $CH_2NMe_2$ | H | H | A-4 |
| 2-80 | $C_6H_5$ | $CH_2NMe_2\cdot HO^*$ | H | H | A-4 |
| 2-81 | $C_6H_5$ | Cl | H | H | A-1 |
| 2-82 | $C_6H_5$ | Me | H | H | A-4 |
| 2-83 | $C_6H_5$ | $C_6H_5$ | H | H | A-4 |
| 2-84 | $C_6H_5$ | $CF_2CHF_2$ | H | H | A-1 |
| 2-85 | $C_6H_5$ | CHO | H | H | A-1 |
| 2-86 | $C_6H_5$ | $NO_2$ | H | H | A-1 |
| 2-87 | $C_6H_5$ | CN | H | H | A-1 |
| 2-88 | $C_6H_5$ | $CH_2CH_2CN$ | H | H | A-1 |
| 2-89 | $C_6H_5$ | $CH=CMe_2$ | H | H | A-1 |
| 2-90 | $C_6H_5$ | $CH(OH)CCl_3$ | H | H | A-1 |
| 2-91 | $C_6H_5CH_2$ | H | H | H | A-1 |
| 2-92 | $CF_3$ | H | H | H | A-1 |
| 2-93 | Cl | H | H | H | A-1 |
| 2-94 | Cl | Cl | H | H | A-1 |
| 2-95 | CHO | H | H | H | A-2 |
| 2-96 | CN | H | H | H | A-2 |
| 2-97 | $CH=CMe_2$ | H | H | H | A-2 |
| 2-98 | $CH=NOEt$ | H | H | H | A-2 |
| 2-99 | OMe | H | H | H | A-1 |
| 2-100 | OMe | H | H | H | A-2 |
| 2-101 | OMe | H | H | H | A-4 |
| 2-102 | SMe | H | H | H | A-1 |

TABLE 6-continued

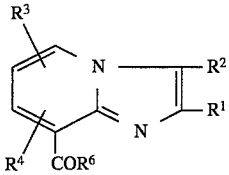

| Compound No. | R¹ | R² | R³ | R⁴ | R⁶ |
|---|---|---|---|---|---|
| 2-103 | H | OMe | H | H | A-1 |
| 2-104 | 2-thienyl | H | H | H | A-1 |
| 2-105 | 2-furyl | H | H | H | A-1 |
| 2-106 | 2-pyridyl | H | H | H | A-1 |
| 2-107 | $C_6H_5$ | H | 5-Me | H | A-1 |
| 2-108 | $C_6H_5$ | H | 5-Me | H | A-2 |
| 2-109 | $C_6H_5$ | H | 5-Me | H | A-4 |
| 2-110 | Me | H | 5-Me | H | A-4 |
| 2-111 | Me | $CH_2NMe_2$ | 5-Me | H | A-2 |
| 2-112 | $C_6H_5$ | H | 5-Me | 7-Me | A-1 |
| 2-113 | $C_6H_5$ | H | 5-$CF_3$ | 7-$CF_3$ | A-1 |
| 2-114 | $C_6H_5OCH_2$ | H | H | H | A-4 |
| 2-115 | $C_6H_5SCH_2$ | H | H | H | A-4 |
| 2-116 | $C_6H_4SOCH_2$ | H | H | H | A-4 |
| 2-117 | $C_6H_5SO_2CH_2$ | H | H | H | A-4 |
| 2-118 | $C_6H_5OCH_2$ | $CH_2NMe_2$ | H | H | A-4 |
| 2-119 | $MeOCH_2$ | H | H | H | A-1 |
| 2-120 | $MeOCH_2$ | 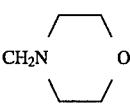 | H | H | A-1 |
| 2-121 | $MeSCH_2$ | H | H | H | A-1 |
| 2-122 | $MeSCH_2$ | H | H | H | A-1 |
| 2-123 | $MeSCH_2$ | $CH_2NMe_2$ | H | H | A-1 |
| 2-124 | $MeSO_2CH_2$ | H | H | H | A-4 |
| 2-125 | 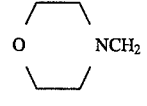 | H | H | H | A-4 |
| 2-126 | $(EtO)_2P(O)CH_2$ | H | H | H | A-4 |
| 2-127 | $Me_2NCSSCH_2$ | H | H | H | A-1 |
| 2-128 | $ClCH_2$ | H | H | H | A-1 |
| 2-129 | $CF_3$ | $C_6H_5NHCO$ | H | H | A-4 |
| 2-130 | H | $C_6H_5CO$ | H | H | A-2 |
| 2-131 | H | $C_6H_5C(OH)$ | H | H | A-2 |
| 2-132 | H | $C_6H_5CH_2$ | H | H | A-2 |
| 2-133 | H | Et | H | H | A-2 |
| 2-134 | $C_6H_5$ | H | H | H | A-4 |
| 2-135 | 2-$MeC_6H_4$ | CHO | H | H | A-1 |
| 2-136 | 2-$FC_6H_4$ | H | H | H | A-4 |
| 2-137 | 2-$FC_6H_4$ | H | H | H | A-2 |
| 2-138 | 3,4-$MeO_2C_6H_3$ | H | H | H | " |
| 2-139 | 2,5-$Me_2C_6H_3$ | H | 6-Me | H | A-1 |
| 2-140 | 4-$FC_6H_4$ | H | H | H | A-2 |
| 2-141 | 2,4-$F_2C_6H_3$ | H | H | H | " |
| 2-142 | 2,6-$F_2C_6H_3$ | H | H | H | " |
| 2-143 | $C_6H_5$ | $CH_2SO_3H$ | H | H | " |
| 2-144 | 4-$Me_2NC_6H_4$ | H | H | H | " |
| 2-145 | 4-$NO_2C_6H_4$ | $NO_2$ | H | H | " |
| 2-146 | $C_6H_5$ | CHO | H | H | " |
| 2-147 | $C_6H_5$ | F | H | H | " |
| 2-148 | $C_6H_5$ | $CH=NC_6H_5$ | H | H | " |
| 2-149 | 4-Me,3-$NO_2C_6H_3$ | $NO_2$ | H | H | " |
| 2-150 | Me | H | H | H | A-11 |
| 2-151 | Et | H | H | H | " |
| 2-152 | 2-$MeC_6H_4$ | H | H | H | " |
| 2-153 | 4-$FC_6H_4$ | H | H | H | " |
| 2-154 | Me | $NO_2$ | H | H | A-2 |
| 2-155 | 4-$C_6H_5-C_6H_5$ | H | H | H | " |
| 2-156 | $C_6H_5$ | H | H | H | " |
| 2-157 | $C_6H_5$ | CN | H | H | " |
| 2-158 | H | $NO_2$ | H | H | " |
| 2-159 | 4-Me,3-$NO_2C_6H_3$ | H | H | H | " |
| 2-160 | 2,4-$(NO_2)_2C_6H_3$ | $NO_2$ | H | H | " |

TABLE 6-continued

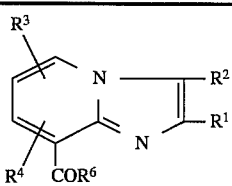

| Compound No. | R¹ | R² | R³ | R⁴ | R⁶ |
|---|---|---|---|---|---|
| 2-161 | 4-SO₃HC₆H₄ | H | H | H | " |
| 2-162 | 2,5-Cl₂C₆H₃ | H | H | H | " |
| 2-163 | 2,5-(MeO)₂C₆H₃ | H | H | H | " |
| 2-164 | Me | SO₃H | H | H | " |
| 2-165 | Me | SO₂NHMe | H | H | " |
| 2-166 | C₆H₅ | H | H | H | " |
| 2-167 | Cl | H | H | H | " |
| 2-168 | 4-NO₂C₆H₄ | H | H | H | " |
| 2-169 | Me | NO₂ | H | H | HNCH(OEt)CONH₂ |
| 2-170 | Me | NO₂ | H | H | A-11 |
| 2-171 | 2-thiazolyl | H | H | H | A-2 |
| 2-272 | CF₃ | H | H | H | HNCH(3-FC₆H₄)CONH |
| 2-173 | 3-HOC₆H₄ | H | H | H | A-2 |
| 2-174 | 2-HOC₆H₄ | H | H | H | " |
| 2-175 | 2-MeOC₆H₄ | H | H | H | " |
| 2-176 | 3-MeOC₆H₄ | H | H | H | " |
| 2-177 | 4-MeOC₆H₄ | H | H | H | " |
| 2-178 | 2-ClC₆H₄ | H | H | H | " |
| 2-179 | 3-ClC₆H₄ | H | H | H | " |
| 2-180 | 4-ClC₆H₄ | H | H | H | " |
| 2-181 | 2,4-Me₂C₆H₃ | H | H | H | " |
| 2-182 | 3,4-Me₂C₆H₃ | H | H | H | " |
| 2-183 | 2-Me,4-MeSC₆H₃ | H | H | H | " |
| 2-184 | 2-Me,4-tBuC₆H₃ | H | H | H | " |
| 2-185 | 2-Me,5-tBuC₆H₃ | H | H | H | " |
| 2-186 | 2-Cl,5-MeC₆H₃ | H | H | H | " |
| 2-187 | 3-MeC₆H₄ | H | H | H | " |
| 2-188 | 4-MeC₆H₄ | H | H | H | " |
| 2-189 | Me | N=CHC₆H₅ | H | H | " |
| 2-190 | OC₆H₅ | H | H | H | " |
| 2-191 | SC₆H₅ | H | H | H | " |
| 2-192 | OMe | H | H | H | " |
| 2-193 | C₆H₅ | H | 5-OH | 6-Cl | " |
| 2-194 | β-naphthyl | H | H | H | " |
| 2-195 | Me | NH₂ | H | H | " |
| 2-196 | 2,3,4,5-Me₄C₆H | H | H | H | " |
| 2-197 | Et | H | H | H | " |
| 2-198 | 2-EtC₆H₄ | H | H | H | " |
| 2-199 | 3-EtC₆H₄ | H | H | H | " |
| 2-200 | 4-EtC₆H₄ | H | H | H | " |
| 2-201 | 4-BrC₆H₄ | H | H | H | " |
| 2-202 | 2,5-Et₂C₆H₃ | H | H | H | " |
| 2-203 | 2-Me,5-ClC₆H₃ | H | H | H | " |
| 2-204 | 2-Me,5-EtC₆H₃ | H | H | H | " |
| 2-205 | 2-Et,5-MeC₆H₃ | H | H | H | " |
| 2-206 | 2,4-(MeO)₂C₆H₃ | H | H | H | " |
| 2-207 | 2-Me₂NCOC₆H₄ | H | H | H | " |
| 2-208 | 2-MeOCH₂C₆H₄ | H | H | H | " |
| 2-209 | 2-Me,4-MeSOC₆H₃ | H | H | H | " |
| 2-210 | 2-Me,4-MeSO₂C₆H₃ | H | H | H | " |
| 2-211 | 5-Me,2-MeOC₆H₃ | H | H | H | " |
| 2-212 | 5-Cl,2-MeOC₆H₃ | H | H | H | " |
| 2-213 | 2,4-(i-Pr)₂C₆H₃ | H | H | H | " |
| 2-214 | 2,5-(i-Pr)₂C₆H₃ | H | H | H | " |
| 2-215 | 4-iPrC₆H₄ | H | H | H | " |
| 2-216 | 5-Me,2-MeSC₆H₃ | H | H | H | " |
| 2-217 | C₆H₁₁ | H | H | H | " |
| 2-218 | 5-t-Bu,2-MeSC₆H₃ | H | H | H | " |
| 2-219 | 5-Cl,2-MeSC₆H₃ | H | H | H | " |
| 2-220 | 4-CNC₆H₄ | H | H | H | " |
| 2-221 | 2-CF₃C₆H₄ | H | H | H | " |
| 2-222 | 3-CF₃C₆H₄ | H | H | H | " |
| 2-223 | 2-Me,5-CF₃C₆H₃ | H | H | H | " |
| 2-224 | α-(imidazo[1,2-a]pyridin-5-ylcarbonylamino)-(2-furyl)acetonitrile | | | | |
| 2-225 | α-(imidazo[1,2-a]pyridin-6-ylcarbonylamino)-(2-furyl)acetonitrile | | | | |
| 2-226 | α-(3-chloro-2-phenyl-imidazo[1,2-b]thiazol-5- | | | | |

TABLE 6-continued

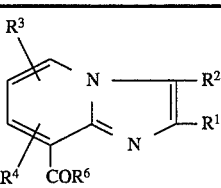

| Compound No. | R$^1$ | R$^2$ | R$^3$ | R$^4$ | R$^6$ |
|---|---|---|---|---|---|
| 2-227 | | α-(imidazo[1,2-b]pyridazin-3-ylcarbonylamino)-(2-furyl)acetonitrile ylcarbonylamino)-(2-furyl)acetonitrile | | | |
| 2-228 | | α-(6-methoxy-imidazo[1,2-b]pyridazin-3-ylcarbonylamino)-(2-furyl)acetonitrile | | | |
| 2-229 | | α-(pyrazolo[1,2-b]pyrimidin-3-ylcarbonylamino)-(2-furyl)acetonitrile | | | |
| 2-230 | | α-(2-methylindolizin-8-ylcarbonylamino)-(2-thienyl)acetonitrile | | | |
| 2-231 | | α-(2-phenyl-imidazo[1,2-b]pyridazin-8-ylcarbonylamino)-(2-thienyl)acetonitrile | | | |
| 2-232 | | α-(6-chloro-2-phenyl-imidazo[1,2-b]pyridazin-8-ylcarbonylamino)-(2-thienyl)acetonitrile | | | |

*HCl: hydrochloride,
*HO: oxalate

A-1 to A-30 for R$^6$ in Table 6 mean the following groups.

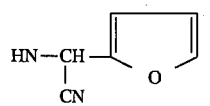 A-1

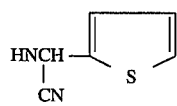 A-2

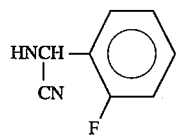 A-3

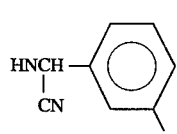 A-4

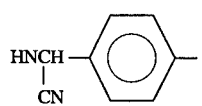 A-5

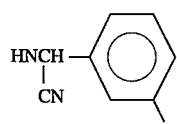 A-6

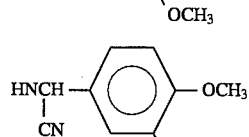 A-7

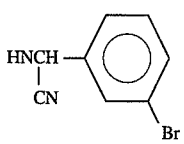 A-8

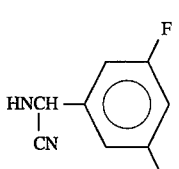 A-9

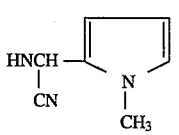 A-10

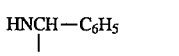 A-11

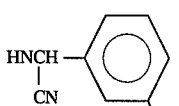 A-12

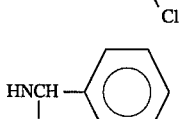 A-13

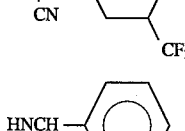 A-14

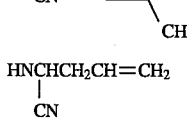 A-15

-continued

| Structure | Code |
|---|---|
| HNCHCH₂CH₂OMe / CN | A-16 |
| NHCHMe / CN | A-17 |
| HNCH-(2-pyridyl) / CN | A-18 |
| HNCH-(4-pyridyl) / CN | A-19 |
| HNCH-(3-pyridyl) / CN | A-20 |
| HNCH-(naphthyl) / CN | A-21 |
| HNCHCH₂C₆H₅ / CN | A-22 |
| N—CH-(furyl) / Me CN | A-23 |
| HNCMe-(furyl) / CN | A-24 |
| HNCH-(5-methylfuryl) / CN | A-25 |
| HNCH₂CN | A-26 |
| HNC(Me)₂CO₂Et | A-27 |
| HNCHCH₂-(2-pyridyl) / CN | A-28 |
| Me-(thienyl)-HNCH / CN | A-29 |
| HNCH-(2-chloropyridyl) / CN | A-30 |

TABLE 7

| Compound No. | m.p. (°C.) | NMR (δ value) |
|---|---|---|
| 2-1 | 149–151 | 6.40–6.55(2H, m), 6.65(1H, d, J=3.0Hz), 6.90(1H, t, J=6.75Hz), 7.50(1H, br), 7.55(1H, d, J=0.9Hz), 7.72(1H, d, J=0.9Hz), 8.12(1H, d, J=6.75Hz), 8.32(1H, d, J=6.75 Hz), 11.30(1H, d, J=8.75Hz). (CDCl₃) |
| 2-2 | 130–131 | 2.45(3H, s), 6.50(2H, m), 6.67(1H, d, J=3.0 Hz), 6.90(1H, t, J=6.75Hz), 7.40(1H, br), 7.55(1H, d, J=1.5Hz), 8.10–8.30(2H, m), 11.45(1H, d, J=7.5Hz). (CDCl₃) |
| 2-3 | 140–141 | 2.40(3H, s), 6.78(1H, d, J=7.5Hz), 7.15(2H, m), 7.45(1H, m), 7.66(1H, d, J=6.0Hz), 7.88 (1H, s), 8.08(1H, d, J=6.75Hz), 8.78(1H, d, J=6.75Hz), 11.28(1H, d, J=7.5Hz). (DMSOd₆) |
| 2-4 | 204–205 | 2.40(3H, s), 6.55(1H, d, J=7.5Hz), 7.08(1H, t, J=6.75Hz), 7.20–7.70(4H, m), 7.88(1H, s), 8.05(1H, d, J=6.75Hz), 8.75(1H, d, J=6.75Hz), 11.24(1H, d, J=7.5 Hz). (DMSOd₆) |
| 2-5 | 102–103 | 1.30(3H, t, J=7.5Hz), 2.80(2H, q, J=7.5Hz), 6.55–6.70(2H, m), 6.75(1H, d, J=3.0Hz), 7.08 (1H, t, J=6.75Hz), 7.83(1H, m), 7.88(1H, s), 8.07(1H, dd, J=6.75Hz, 1.5Hz), 8.78(1H, dd, J=6.75Hz, 1.5Hz) 11.35(1H, d, J=6.75Hz). (DMSOd₆) |
| 2-7 | 85–87 | 1.35(6H, d, J=6.0Hz), 3.08(1H, m), 6.45–6.70 (2H, m), 6.70(1H, d, J=3.0Hz), 7.03(1H, t, J=6.75Hz), 7.75(1H, m), 7.80(1H, s), 8.06(1H, dd, J=6.75Hz, 1.5Hz), 8.73(1H, dd, J=6.75Hz, 1.5Hz), 11.48(1H, d, J=6.75Hz). (DMSOd₆) |
| 2-9 | 112–114 | 1.32(9H, s), 6.48–6.65(2H, m), 6.73(1H, d, J=3.0Hz), 7.05(1H, t, J=6.75Hz), 7.78(1H, m), 7.84(1H, s), 8.07(1H, d, J=6.75Hz), 8.74(1H, d, J=6.75Hz), 11.53(1H, d, J=6.75Hz). (DMSOd₆) |
| 2-10 | 142–143 | 6.50(2H, m), 6.65(1H, d, J=3.75Hz), 7.15(1H, t, J=6.75Hz), 7.45(1H, d, J=1.5Hz), 7.58(1H, s), 8.25(2H, m), 10.95(1H, d, J=7.5Hz). (CDCl₃) |
| 2-11 | 157–159 | 2.45(3H, s), 6.35–6.50(2H, m), 6.65(1H, d, J=3.95Hz), 7.08(1H, t, J=6.75Hz), 7.50(1H, d, J=1.5Hz), 8.10–8.30(2H, m), 11.05(1H, d, J=8.25Hz) (CDCl₃) |
| 2-15 | 162–164 | 2.20(6H, s), 2.40(3H, s), 3.65(2H, s), 6.50 (2H, m), 6.68(1H, d, J=3.0Hz), 6.92(1H, t, J=6.75Hz), 7.48(1H, br), 8.12(1H, d, J=6.75Hz), 8.40(1H, d, J=6.75Hz), 11.58(1H, d, J=7.50 Hz). (CDCl₃) |
| 2-17 | 123–124 | 2.20(6H, s), 2.40(3H, s), 3.70(2H, s), 6.47(1H, d, J=7.5Hz), 6.95(1H, d, J=6.75Hz), 7.10–7.50 (4H, m), 8.20(1H, d, J=6.75Hz), 8.45(1H, d, J=6.75Hz), 11.58(1H, d, J=7.50Hz). (CDCl₃) |
| 2-19 | 171–174 | |
| 2-20 | 184–186 | 2.35–2.60(4H, m), 2.42(3H, s), 3.55–3.75(4H, m), 3.77(2H, s), 6.50(2H, m), 6.65(1H, d, J=3.0Hz), 6.95(1H, t, J=6.75Hz), 7.55(1H, br), 8.25(1H, d, J=6.75Hz), 8.47(1H, d, J=6.75 Hz), 11.45(1H, d, J=7.5Hz). (DMSOd₆) |
| 2-24 | 197–199 | 6.35–6.50(2H, m), 6.68(1H, d, J=3.75Hz), 6.95 (1H, t, J=6.75Hz), 7.35–7.65(4H, m), 7.70–7.90 (2H, m), 7.92(1H, s), 8.10–8.30(2H, m), 11.56 (1H, d, J=7.50Hz). (CDCl₃) |
| 2-25 | 187–189 | 6.76(1H, d, J=6.3Hz), 7.05–7.32(2H, m), 7.33–7.65(4H, m), 7.70–7.82(1H, m), 7.86–8.02(2H, m), 8.04–8.20(1H, m), 8.59(1H, s), 8.73–8.90 (1H, m), 11.34(1H, d, J=6.3Hz). (DMSOd₆) |
| 2-26 | 176–177 | 6.60(1H, d, J=7.5Hz), 7.14(1H, t, J=6.75Hz), 7.35–7.60(7H, m), 7.80–8.00(2H, m), 8.15(1H, d, J=6.75Hz), 8.67(1H, s), 8.84(1H, d, J=6.75 Hz), 11.48(1H, d, J=7.5Hz). (DMSOd₆) |
| 2-27 | 192–193 | 6.50(1H, d, J=6.6Hz), 7.14(1H, t, J=7.5Hz), 7.36–7.73(7H, m), 7.80–7.99(2H, m), 8.02–8.20 (1H, m), 8.56(1H, s), 8.72–8.89(1H, m), 11.30 (1H, d, J=6.6Hz). (DMSOd₆) |
| 2-28 | 205–206 | 6.36(1H, d, J=6.6Hz), 6.98–7.53(6H, m), 7.68–7.95(4H, m), 8.03–8.20(1H, m), 8.42(1H, s), 8.66–8.80(1H, m), 11.33(1H, d, J=6.6Hz). (CDCl₃+DMSOd₆) |
| 2-29 | 168–170 | 3.82(3H, s), 6.35(1H, d, J=6.3Hz), 7.03–7.66 (8H, m), 7.78–7.95(2H, m), 8.10 (1H, dd, J= |

TABLE 7-continued

| Compound No. | m.p. (°C.) | NMR (δ value) |
|---|---|---|
| 2-30 | 181–182 | 1.35Hz, 7.5Hz), 8.54(1H, s), 8.78(1H, dd, J=1.35Hz, 7.5Hz), 11.28(1H, d, J=6.3Hz). (DMSOd$_6$)<br>3.80(3H, s), 3.85(3H, s), 6.24(1H, d, J=6.3Hz), 7.04–7.53(7H, m), 7.70–7.91(2H, m), 8.10(1H, dd, J=1.5Hz, 7.2Hz), 8.53(1H, s), 8.79(1H, dd, J=1.5Hz, 7.2Hz), 11.22(1H, d, J=6.3Hz). (DMSOd$_6$) |
| 2-31 | 203–204 | 6.48(1H, d, J=6.45Hz), 7.12(1H, t, J=7.2Hz), 7.32–7.65(4H, m), 7.68–8.02(5H, m), 8.10(1H, dd, J=1.35, 7.2Hz), 8.55(1H, s), 8.80(1H, dd, J=1.35, 7.2Hz), 11.25(1H, d, J=6.45Hz). (DMSOd$_6$) |
| 2-32 | 219–220 | 6.55(1H, d, J=6.75Hz), 7.15(1H, t, J=7.05Hz), 7.24–7.65(6H, m), 7.88–8.03(2H, m), 8.10(1H, dd, J=1.35, 7.05Hz), 8.53(1H, s), 8.82(1H, dd, J=1.35, 7.05Hz), 11.30(1H, d, J=6.75Hz). (DMSOd$_6$) |
| 2-33 | 207–208 | 3.71(3H, s), 6.10–6.26(1H, m), 6.43–6.60(2H, m), 6.89–7.01(1H, m), 7.13(1H, t, J=7.5Hz), 7.31–7.58(3H, m), 7.72–7.92(2H, m), 8.11(1H, dd, J=1.35, 7.5Hz), 8.55(1H, s), 8.79(1H, dd, J=1.35, 7.5Hz), 11.13(1H, d, J=6.45Hz). (DMSOd$_6$) |
| 2-34 | 174–175 | 6.28(1H, d, J=7.5Hz), 6.95(1H, t, J=6.9Hz), 7.23–7.84(10H, m), 7.90(1H, s), 8.11–8.32(2H, m), 11.48(1H, d, J=7.5Hz). (CDCl$_3$) |
| 2-35 | 210–211 | 6.32(1H, d, J=7.5Hz), 7.03(1H, t, J=7.2Hz), 7.17–7.92(4H, m), 8.16(1H, dd, J=1.35Hz, 7.2Hz), 8.22(1H, s), 8.57(1H, dd, J=1.35Hz, 7.2Hz), 11.46(1H, d, J=7.5Hz). (DMSOd$_6$+CDCl$_3$) |
| 2-36 | 192–193 | 6.52(1H, d, J=7.35Hz), 7.05(1H, t, J=7.2Hz), 7.32–7.53(3H, m), 7.61–7.91(4H, m), 7.92–8.22(3H, m), 8.33(1H, s), 8.59(1H, dd, J=1.35Hz, 7.2Hz), 11.41(1H, d, J=7.35Hz). (CDCl$_3$+DMSOd$_6$) |
| 2-37 | 189–190 | 2.42(3H, s), 6.34(1H, d, J=6.3Hz), 7.14(1H, t, J=7.2Hz), 7.30–7.68(7H, m), 7.74–7.92(2H, m), 8.11(1H, dd, J=1.35Hz, 7.2Hz)8.55(1H, s), 8.79(1H, dd, J=1.35Hz, 7.2Hz), 11.25(1H, d, J=6.3Hz). (DMSOd$_6$) |
| 2-40 | 168–169 | 1.23(6H, d, J=7.2Hz), 2.12–2.50(1H, m), 5.05(1H, dd, J=6.9Hz, 7.5Hz), 7.16(1H, t, J=6.9Hz), 7.28–7.65(3H, m), 7.90–8.20(3H, m), 8.60(1H, s), 8.82(1H, dd, J=1.35Hz, 6.9Hz), 10.90(1H, d, J=7.5Hz). (DMSOd$_6$) |
| 2-41 | 181–182 | 6.37(1H, d, J=7.5Hz), 6.95(1H, t, J=7.2Hz), 6.27–8.37(11H, m), 8.79–8.94(1H, m), 11.97(1H, d, J=7.50Hz). (CDCl$_3$) |
| 2-42 | 213–215 | 6.58(1H, d, J=6.45Hz), 7.13(1H, t, J=7.2Hz), 7.31–7.71(4H, m), 7.80–8.30(4H, m), 8.55(1H, s), 8.68–8.87(2H, m), 8.96(1H, d, J=2.85Hz) 11.30(1H, d, J=6.45Hz). (CDCl$_3$) |
| 2-45 | 182–183 | 3.31(2H, d, J=7.5Hz), 5.32–5.62(1H, m), 6.93(1H, t, J=6.6Hz), 7.23–7.62(8H, m), 7.65–8.02(3H, m), 8.07–8.36(2H, m), 11.03(1H, d, J=8.7Hz). (CDCl$_3$) |
| 2-46 | 122–124 | 3.02(3H, br), 6.59(1H, br), 6.88–7.12(2H, m), 7.18–7.58(5H, m), 7.62–7.83(1H, m), 7.93–8.25(2H, m), 8.35(1H, s), 8.60(1H, d, J=7.2Hz). (CD$_3$COCD$_3$) |
| 2-47 | 190–192 | 2.22(3H, s), 6.62–6.75(1H, m), 6.82(1H, d, J=3.0Hz), 7.14(1H, t, J=6.9Hz), 7.31–7.63(3H, m), 7.76–8.19(4H, m), 8.56(1H, s), 8.72–8.90(1H, m), 11.48(1H, s). (DMSOd$_6$) |
| 2-48 | 192–193 | 2.42(3H, s), 6.20–6.31(1H, m), 6.56(1H, d, J=3.3Hz), 7.15(1H, t, J=7.2Hz), 7.28–7.63(3H, m), 7.89–8.06(3H, m), 8.12(1H, dd, J=1.35Hz, 7.2Hz), 8.59(1H, s), 8.81(1H, dd, J=1.35Hz, 7.2Hz), 11.37(1H, d, J=6.9Hz). (DMSOd$_6$) |
| 2-49 | 173–174 | 4.60(2H, d, J=6.3Hz), 7.12(1H, t, J=6.9Hz), 7.24–7.62(3H, m), 8.00–8.25(3H, m), 8.58(1H, s), 8.71–8.87(1H, m), 10.59(1H, t, J=6.3Hz). (DMSOd$_6$) |
| 2-50 | 109–110 | 1.27(3H, t, J=7.5Hz), 1.75(6H, s), 4.23(2H, q, J=7.5Hz), 6.92(1H, t, J=6.9Hz), 7.23–7.68(3H, m), 7.89–8.18(4H, m), 8.29–8.50(1H, m), 10.95(1H, br). (DMSOd$_6$+CDCl$_3$) |
| 2-52 | 196–197 | 2.41(3H, s), 6.49(1H, d, J=7.8Hz), 6.80–7.06(2H, m), 7.23–7.57(4H, m), 7.75–7.95(3H, m), 8.07–8.32(2H, m), 11.48(1H, d, J=7.8Hz). (CDCl$_3$) |
| 2-53 | 159–161 | 6.60(1H, d, J=6.6Hz), 7.12(1H, t, J=6.9Hz), 7.32–7.61(3H, m), 7.69(1H, d, J=9.3Hz), 7.82–8.14(3H, m), 8.22(1H, dd, J=1.2, 9.3Hz), 8.57(1H, s), 8.72–8.89(2H, m), 11.26(1H, d, J=6.6Hz). (DMSOd$_6$) |
| 2-54 | 175–177 | 2.54(3H, s), 6.55–6.70(2H, m), 6.75(1H, d, J=3.0Hz), 7.20(1H, t, J=6.75Hz), 7.30–7.50(3H, m), 7.80–8.00(2H, m), 8.15(1H, d, J=6.75Hz), 8.45(1H, s), 8.85(1H, d, J=6.75Hz), 11.35(1H, d, J=7.50Hz). (DMSOd$_6$) |
| 2-55 | 175–176 | 2.45(3H, s), 6.75(1H, d, J=7.5Hz)7.10–8.30(8H, m), 8.42(1H, s), 8.86(1H, d, J=6.75Hz), 11.27(1H, d, J=7.5Hz), (DMSOd$_6$) |
| 2-56 | 119–120 | 2.45(3H, s), 6.53(1H, d, J=7.5Hz), 7.10–7.90(9H, m), 8.15(1H, d, J=6.75Hz), 8.45(1H, s), 8.86(1H, d, J=6.75Hz), 11.28(1H, d, J=7.5Hz). (DMSOd$_6$) |
| 2-57 | 214–216 | 2.40(3H, s), 6.50–6.70(2H, m), 6.82(1H, d, J=3.0Hz), 7.00–7.55(3H, m), 7.65–7.95(3H, m), 8.12(1H, d, J=6.75Hz), 8.55(1H, s), 8.80(1H, d, J=6.75Hz), 11.45(1H, d, J=6.75Hz). (DMSOd$_6$). |
| 2-58 | 198–200 | 2.35(3H, s), 6.60–6.75(2H, m), 6.80(1H, d, J=3.0Hz), 7.15(1H, t, J=6.75Hz), 7.32(2H, d, J=8.35Hz), 7.75–8.003(1H, m), 8.10(1H, d, J=6.75Hz), 8.54(1H, s), 8.80(1H, d, J=6.75Hz), 11.52(1H, d, J=6.75Hz). (DMSOd$_6$) |
| 2-59 | 173–175 | 2.39(3H, s), 2.50(3H, s), 6.40(1H, d, J=6.6Hz), 6.41–6.58(2H, m), 6.72(1H, d, J=3.0Hz), 7.08(1H, t, J=6.0Hz), 7.18(1H, m), 7.52–7.72(2H, m), 8.05(1H, s), 8.27(1H, dd, J=7.5Hz, 0.3Hz)8.59(1H, dd, J=7.5Hz, 0.3Hz), 11.48(1H, d, J=6.6Hz). (CDCl$_3$) |
| 2-60 | 134–135 | 2.34(3H, s), 2.47(3H, s), 6.53(1H, d, J=7.5Hz), 6.90–7.25(4H, m), 7.31–7.48(2H, m), 7.80(1H, s), 7.18–7.40(2H, m), 11.56(1H, d, J=7.5Hz). (CDCl$_3$) |
| 2-63 | 167–169 | 4.01(3H, s), 6.55–6.70(2H, m), 6.80(1H, d, J=3.0Hz), 7.00–7.50(4H, m), 7.95(1H, br), 8.00–8.25(2H, m), 8.68(1H, s), 8.87(1H, t, J=6.75Hz), 11.51(1H, d, J=6.0Hz). (DMSOd$_6$) |
| 2-64 | 167–169 | 3.82(3H, s), 6.55–6.70(2H, m), 6.82(1H, d, J=3.0Hz), 6.85–7.60(5H, m), 7.89(1H, m), 8.13(1H, d, J=6.75Hz), 8.58(1H, s), 8.80(1H, d, J=6.75Hz), 11.42(1H, d, J=6.75Hz). (DMSOd$_6$) |
| 2-65 | 179–180 | 3.85(3H, s), 6.55–6.70(2H, m), 6.70(1H, d, J=3.0Hz), 7.00–7.25(3H, m), 7.85–8.05(3H, m), 8.12(1H, d, J=6.75Hz), 8.45(1H, s), 8.80(1H, d, J=6.75Hz), 11.45(1H, d, J=6.75Hz). (DMSOd$_6$) |
| 2-66 | 186–188 | 3.84(6H, s), 6.58–6.71(2H, m), 6.80(1H, d, J=3.0Hz), 7.43–7.68(2H, m), 7.10(1H, d, J=7.5Hz), 8.10(1H, d, J=6.75Hz), 8.50(1H, s), 8.80(1H, d, J=6.75Hz), 11.40(1H, d, J=7.5Hz). (DMSOd$_6$) |
| 2-67 | 140–141 | 3.83(3H, s), 3.90(3H, s), 6.40(1H, d, J=7.5Hz) 6.83–7.20(3H, m), 7.25–7.60(5H, m), 7.88(1H, s), 8.18(1H, dd, J=6.0Hz, 1.5Hz), 8.25(1H, dd, J=6.0Hz, 1.5Hz), 11.55(1H, d, J=7.5Hz). (CDCl$_3$) |
| 2-68 | 176–178 | 6.55–6.70(2H, m), 6.78(1H, d, J=3.0Hz), 7.18(1H, t, J=6.75Hz), 7.34–7.66(3H, m), 7.78(1H, br), 8.10–8.30(2H, m), 8.76(1H, s), 8.88(1H, d, |

TABLE 7-continued

| Compound No. | m.p. (°C.) | NMR (δ value) |
|---|---|---|
| | | J=6.75Hz), 11.30(1H, d, J=6.75Hz). (DMSOd₆) |
| 2-69 | 235~237 | 6.55–6.75(2H, m), 6.82(1H, d, J=3.0Hz), 7.20 (1H, t, J=6.75Hz), 7.35–7.70(2H, m), 7.88–8.30 (4H, m), 8.66(1H, s), 8.84(1H, d, J=6.75Hz), 11.32(1H, d, J=6.75Hz). (DMSOd₆) |
| 2-70 | 222~224 | 6.55–6.70(2H, m), 6.83(1H, d, J=3.0Hz), 7.18 (1H, t, J=6.75Hz), 7.53(2H, d, J=8.25Hz), 7.90–8.20(4H, m), 8.61(1H, s), 8.82(1H, d, J=6.75Hz), 11.38(1H, d, J=6.75Hz). (DMSOd₆) |
| 2-71 | 233~234 | 6.55–6.75(2H, m), 6.82(1H, d, J=3.0Hz), 7.16 (1H, t, J=6.75Hz), 7.78(2H, d, J=8.25Hz), 7.90(2H, d, J=8.25Hz), 7.98(1H, m), 8.15(1H, d, J=6.75Hz), 8.60(1H, s), 8.83(1H, d, J=6.75 Hz), 11.32(1H, d, J=6.75Hz). (DMSOd₆) |
| 2-72 | 249~251 | 6.55–6.70(2H, m), 6.78(1H, d, J=3.0Hz), 7.19 (1H, t, J=6.75Hz), 7.95–8.45(6H, m), 8.75–8.90 (2H, m), 11.25(1H, d, J=6.75Hz). (DMSOd₆) |
| 2-73 | 208~210 | 6.65(2H, m), 6.83(1H, d, J=3.0Hz), 7.21(1H, t, J=6.75Hz), 7.30–7.60(3H, m), 7.95(1H, m), 8.05–8.35(2H, m), 8.54(1H, d, J=4.5Hz), 8.90 (1H, d, J=6.75Hz), 11.46(1H, d, J=7.5Hz). (DMSOd₆) |
| 2-78 | 173~175 | 2.26(6H, s), 3.92(2H, s), 6.53(1H, d, J=8.1Hz), 6.90–7.11(2H, m), 7.32–7.55(4H, m), 7.63–7.84 (2H, m), 8.28(1H, dd, J=7.5Hz, 0.75Hz), 8.63 (1H, dd, J=7.5Hz, 0.75Hz), 11.65(1H, d, J= 8.1Hz). (CDCl₃) |
| 2-79 | 176~177 | 2.26(6H, s), 3.93(2H, s), 6.36(1H, d, J=8.1Hz), 6.91–7.34(2H, m), 7.43–7.60(6H, m), 7.66–7.85 (2H, m), 8.21–8.38(1H, m), 8.57–8.73(1H, m), 11.65(1H, d, J=8.1Hz). (CDCl₃) |
| 2-80 | ~125 | |
| 2-81 | 173 | 6.58–6.70(2H, m), 6.80(1H, d, J=3.3Hz), 7.32 (1H, t, J=6.9Hz), 7.40–7.73(3H, m), 7.88–8.29 (4H, m), 8.65(1H, dd, J=1.5Hz, 6.9Hz), 11.05 (1H, d, J=7.2Hz). (DMSOd₆) |
| 2-82 | 169~171 | 2.70(3H, s), 6.48(1H, d, J=6.3Hz), 7.18(1H, t, J=6.9Hz), 7.28–7.86(9H, m), 8.12(1H, dd, J=1.5Hz, 6.9Hz), 8.62(1H, dd, J=1.5Hz, 6.9Hz), 11.39(1H, d, J=6.3Hz). (DMSOd₆) |
| 2-83 | 129~131 | 6.32(1H, d, J=6.3Hz), 6.91(1H, t, J=6.3Hz), 7.15–7.75(14H, m), 8.05(1H, dd, J=6.3Hz, 1.5Hz), 8.25(1H, dd, J=6.3Hz, 1.5Hz), 11.68 (1H, d, J=6.3Hz). (CDCl₃) |
| 2-92 | 145~146 | 6.31(1H, d, J=8.4Hz), 7.12(1H, t, J=6.5Hz), 7.20–7.55(4H, m), 7.98(1H, s), 7.30(1H, dd, J=7.5Hz, 1.5Hz), 7.35(1H, dd, J=7.5Hz, 1.5Hz), 10.85(1H, d, J=8.4Hz). (CDCl₃) |
| 2-104 | 221~222 | 6.15–6.70(2H, m), 6.70–6.95(2H, m), 7.20(1H, t, J=6.5Hz), 7.80–7.95(1H, m), 8.27(1H, m), 7.5Hz, 1.5Hz), 8.41(1H, s), 8.83(1H, dd, J= 7.5Hz, 1.5Hz), 11.50(1H, d, J=6.0Hz). (DMSOd₆) |
| 2-109 | 197~198 | 2.42(3H, s), 6.29(1H, d, J=8.4Hz), 7.15–7.55(7H, m), 7.70–7.85(2H, m), 7.80(1H, s), 8.05(2H, s), 11.53(1H, d, J=8.4Hz). (CDCl₃) |
| 2-112 | 206~207 | 2.57(3H, s), 2.71(3H, s), 6.32(1H, d, J=6.0 Hz), 6.50(1H, d, J=6.3Hz), 6.54(1H, d, J= 6.3Hz), 6.67(1H, d, J=3.0Hz), 7.31–7.52 (3H, m), 7.55(1H, m), 7.62(1H, s), 7.71– 7.92(2H, m), 12.30(1H, d, J=6.0Hz). (CDCl₃) |
| 2-114 | 119~121 | 4.22(2H, s), 6.38(1H, d, J=9.0Hz), 6.92 (1H, t, J=8.0Hz), 7.10–7.50(9H, m), 7.55 (1H, s), 8.19(2H, d, J=6.3Hz), 11.23(1H, d, J=9.0Hz). (CDCl₃) |
| 2-115 | 138~139 | 5.28(2H, s), 6.44(1H, d, J=9.0Hz), 6.95 (1H, t, J=8.0Hz), 7.00–7.50(9H, m), 7.70 (1H, s), 8.25(2H, d, J=6.3Hz), 11.21(1H, d, J=9.0Hz). (CDCl₃) |
| 2-119 | 127~128 | 3.50(3H, s), 4.65(2H, s), 6.33–6.50(2H, m), 6.93(1H, t, J=6.3Hz), 7.49(1H, m), 7.62 (1H, s), 8.15–8.32(2H, m), 11.25(1H, d, J= 7.5Hz). (CDCl₃) |

TABLE 7-continued

| Compound No. | m.p. (°C.) | NMR (δ value) |
|---|---|---|
| 2-120 | 108~109 | 2.31–2.57(4H, m), 3.47(3H, s), 3.55–3.75 (4H, m), 3.90(2H, s), 4.63(2H, s), 6.37– 6.53(2H, m), 6.93(1H, t, J=6.3Hz), 7.48 (1H, m), 8.23(1H, dd, J=7.5Hz, 1.5Hz), 8.51(1H, dd, J=7.5Hz, 1.5Hz), 11.32(1H, d, J=7.5Hz). (CDCl₃) |
| 2-121 | 165~166 | 2.17(3H, s), 3.80(2H, s), 6.33–6.50(2H, m), 6.60–6.73(1H, m), 6.95(1H, d, J=6.0Hz), 7.50(1H, m), 7.60(1H, s), 8.12–8.30(2H, m), 11.27(1H, d, J=7.5Hz). (CDCl₃) |
| 2-122 | 214~216 | 2.61(3H, d, J=3.0Hz), 4.20(2H, s), 6.33– 6.51(2H, m), 6.58–6.75(1H, m), 7.08(1H, t, J=6.0Hz), 7.60(1H, m), 8.00(1H, s), 8.18 (1H, dd, J=6.0Hz, 1.5Hz), 8.60(1H, dd, J= 6.0Hz, 1.5Hz), 11.08(1H, d, J=6.3Hz). (CDCl₃+DMSOd₆) |
| 2-123 | 117~118 | 2.19(3H, s), 2.25(6H, s), 3.72(2H, s), 3.83(2H, s), 6.32–6.48(2H, m), 6.65(1H, d, J=3.0Hz), 6.98(1H, d, J=6.0Hz), 7.50(1H, m), 7.72(1H, dd, J=6.0Hz,, 1.5Hz), 8.50(1H, dd, J=6.0Hz, 1.5Hz), 11.40(1H, d, J=6.6Hz). (CDCl₃) |
| 2-127 | 169~171 | 3.38(3H, br), 3.55(3H, br), 4.75(2H, s), 6.36–6.51(2H, m), 6.59–6.70(1H, m), 6.93 (1H, t, J=6.0Hz), 7.45–7.55(1H, m), 7.78 (1H, s), 8.28(1H, d, J=7.5Hz), 11.21(1H, br). (CDCl₃) |
| 2-128 | 184~186 | 4.73(2H, s), 6.32–6.50(2H, m), 6.65(1H, d, J=3.0Hz), 6.98(1H, d, J=6.0Hz), 7.50(1H, m), 7.72(1H, s), 8.23(1H, d, J=7.5Hz), 11.10(1H, br). (CDCl₃) |
| 2-134 | 120–125 (hydrochloride) | 5.70(1H, br), 6.50(1H, d, J=6.3Hz), 7.16–7.82(8H, m), 7.82–8.10(2H, m), 8.16–8.32(1H, m), 8.68(1H, s), 8.82– 9.00(1H, m), 11.21(1H, d, J=6.3Hz). (DMSOd₆) |
| 2-135 | 112~115 | 2.40(3H, s), 6.35(2H, m), 6.63(1H, d, J= 3.0Hz), 7.20–7.60(8H, m), 8.55(1H, d, J= 6.75Hz), 9.80(1H, d, J=6.75Hz), 9.82 (1H, s), 11.07(1H, d, J=8.5Hz). (CDCl₃) |
| 2-136 | 171~172 | 6.50(1H, d, J=7.5Hz), 7.10–7.75(8H, m), 7.95(1H, m), 8.18(1H, d, J=6.75Hz), 8.50 (1H, d, J=4.5Hz), 8.90(1H, d, J=6.75Hz), 11.20(1H, d, J=7.5Hz). (DMSOd₆) |
| 2-137 | 190~191 | 6.75(1H, d, J=7.5Hz), 7.05–7.55(6H, m), 7.72(1H, d, J=6.0Hz), 7.95–8.25(1H, m), 8.15(1H, d, J=6.75Hz), 8.48(1H, d, J= 4.5Hz), 8.88(1H, d, J=6.75Hz), 11.25(1H, d, J=7.5Hz). (DMSOd₆) |
| 2-138 | 192~193 | 3.83(3H, s), 3.91(3H, s), 6.58(1H, d, J= 7.5Hz), 6.80–7.15(3H, m), 7.82(1H, s), 8.23(1H, m), 11.58(1H, d, J=7.5Hz) (CDCl₃) |
| 2-139 | 184~185 | 2.38(6H, s), 2.43(3H, s), 6.32(1H, d, J= 7.5Hz), 6.32–6.49(2H, m), 6.61(1H, m), 6.95–7.20(2H, m), 7.50(1H, m), 6.62(2H, m), 8.05(1H, m), 11.50(1H, d, J=7.5Hz). (CDCl₃) |
| 2-140 | 215~217 | 6.77(1H, d, J=7.5Hz), 7.08–7.45(4H, m), 7.52(1H, d, J=3.0Hz), 7.77(1H, dd, J=6.0, 3.0Hz), 7.85–8.20(3H, m), 8.58(1H, s), 8.80(1H, d, J=6.75Hz), 11.25(1H, d, J= 7.5Hz). (DMSOd₆) |
| 2-141 | 220~222 | 6.75(1H, d, J=7.5Hz), 7.10–7.50(5H, m), 7.77(1H, dd, J=3.75, 5.25Hz), 7.90–8.35 (2H, m), 8.50(1H, d, J=4.0Hz), 8.90(1H, d, J=6.75Hz), 11.13(1H, d, J=7.5Hz). (DMSOd₆) |
| 2-142 | 154~156 | 6.58(1H, d, J=7.5Hz), 6.80–7.50(7H, m), 8.05(1H, t, J=1.5Hz), 8.15–8.40(2H, m), 11.56(1H, d, J=7.5Hz). (CDCl₃) |
| 2-143 | 165~166 | 5.10(2H, s), 6.52(1H, d, J=7.5Hz), 7.00– 7.21(2H, m), 7.40–7.60(4H, m), 7.72– 7.88(2H, m), 8.28(1H, m), 8.68(1H, m), 11.63(1H, d, J=7.5Hz). (CDCl₃) |

TABLE 7-continued

| Compound No. | m.p. (°C.) | NMR (δ value) |
|---|---|---|
| 2-144 | 181~182 | 3.00(6H, s), 6.55(1H, d, J=7.5Hz), 6.73 (2H, d, J=9.0Hz), 6.82-7.15(2H, m), 7.20 (2H, d, J=9.0Hz), 7.32-7.50(2H, m), 7.74 (1H, s), 8.15(2H, m), 11.70(1H, d, J= 7.54Hz). (CDCl₃) |
| 2-145 | 202~204 | 6.70-6.85(1H, m), 7.03-7.19(1H, m), 7.38-7.50(1H, m), 7.60-7.83(2H, m), 8.08-8.63(5H, m), 9.67(1H, dd, J=1.35, 7.35Hz), 10.49(1H, d, J=6.75Hz). (DMSOd₆) |
| 2-146 | 182~184 (decomp.) | 6.35(1H, d, J=7.65Hz), 6.99-7.16(1H, m), 7.21-7.33(1H, m), 7.36-7.66(5H, m), 7.70-7.92(2H, m), 8.58(1H, dd, J=1.35, 7.5Hz), 9.83(1H, dd, J=1.35, 7.2Hz), 10.15(1H, s), 11.19(1H, d, J=7.65Hz). (CDCl₃) |
| 2-147 | 162~164 | 6.58(1H, d, J=7.5Hz), 6.80-7.50(7H, m), 8.05(1H, d, J=1.5Hz), 8.15-8.40(2H, m), 11.56(1H, d, J=7.5Hz). (CDCl₃) |
| 2-148 | 177~179 | 6.57(1H, d, J=7.8Hz), 6.99-7.12(1H, m), 7.15-7.62(11H, m), 7.68-7.86(2Hm), 8.50 (1H, dd, J=1.35, 7.5Hz), 8.88(1H, s), 10.30(1H, dd, J=1.35, 7.5Hz), 11.42(1H, d, J=7.8Hz). (CDCl₃) |
| 2-149 | 208~210 | 2.63(3H, s), 6.71(1H, d, J=7.5Hz), 7.00-7.18(1H, m), 7.38-7.50(1H, m), 7.56-7.82(3H, m), 8.14(1H, dd, J=1.35, 8.25Hz), 8.48-8.63(2H, m), 9.58-9.73(1H, m), 10.51(1H, d, J=7.5Hz). (DMSOd₆) |
| 2-150 | 149~151 | 2.43(3H, s), 6.60(1H, d, J=7.5Hz), 7.22(1H, t, J=6.75Hz), 7.40-7.80(5H, m), 7.94(1H, s), 8.15(1H, dd, J=6.75, 1.50Hz), 8.85(1H, dd, J=6.75, 1.50Hz), 11.28(1H, d, J=7.51Hz). (DMSOd₆) |
| 2-151 | 134~135 | 1.30(3H, t, J=7.0Hz), 2.80(2H, q, J=7.0Hz), 6.40(1H, d, J=7.5Hz), 6.93(1H, t, J=6.75Hz), 7.30-7.75(6H, m), 8.08-8.30(2H, m), 11.52(1H, d, J=7.5Hz). (CDCl₃) |
| 2-152 | 141~143 | 2.45(3H, s), 6.42(1H, d, J=7.5Hz), 7.05-7.38(4 H, m), 7.40-7.85(6H, m), 8.13(1H, d, J=6.75 Hz), 8.40(1H, s), 8.85(1H, d, J=6.75Hz), 11.18 (1H, d, J=7.5Hz). (DMSOd₆) |
| 2-153 | 235~237 | 6.40(1H, d, J=7.5Hz), 7.00-7.40(3H, m), 7.45-8.00(7H, m), 8.12(1H, d, J=6.75Hz), 8.50(1H, s), 8.80(1H, d, J=6.75Hz), 11.19(1H, d, J=7.5 Hz). (DMSOd₆) |
| 2-154 | | 2.85(3H, s), 6.55(1H, d, J=7.5Hz), 7.09(1H, m), 7.20-7.55(3H, m), 8.60(1H, d, J=6.75Hz), 9.60(1H, m), 7.49-7.64(1H, m), 10.85(1H, d, J= 7.5Hz). (CDCl₃) |
| 2-155 | 163~165 | 6.53(1H, d, J=7.5Hz), 6.95(1H, t, J=6.75 Hz), 7.00-7.30(1H, m), 7.32-7.76(1H, m), 7.92(1H, s), 8.21(2H, m), 11.57(1H, d, J= 7.5Hz). (CDCl₃) |
| 2-156 | 111~115 (hydrochloride) | 6.75(1H, d, J=6.75Hz), 6.68-7.11(1H, br), 7.11-7.82(7H, m), 7.88-8.11(2H, m), 8.23 (1H, dd, J=1.35, 7.5Hz), 8.68(1H, s), 8.92 (1H, dd, J=1.35, 7.5Hz), 11.26(1H, d, J= 6.75Hz). (DMSOd₆) |
| 2-157 | 174~175 | 6.52(1H, d, J=7.5Hz), 7.00-7.19(2H, m), 7.36-7.58(5H, m), 7.98-8.16(2H, m), 8.25-8.48(2H, m), 11.27(1H, d, J=7.5Hz) (CDCl₃) |
| 2-158 | 167~168 | 6.57(1H, d, J=8.4Hz), 7.02-7.18(1H, m), 7.38-7.70(3H, m), 8.63(1H, dd, J=1.35, 7.5Hz), 8.66(1H, s), 9.61(1H, dd, J=1.35, 7.5Hz), 10.70(1H, d, J=8.4Hz). (CDCl₃+DMSOd₆) |
| 2-159 | 238~240 (decomp.) | 2.58(3H, s), 6.68(1H, d, J=6.9Hz), 7.03-7.25(2H, m), 7.46-7.72(3H, m), 8.01-8.24 (2H, m), 8.45-8.52(1H, m), 8.63(1H, s), 8.70-8.86(1H, m), 11.11(1H, d, J=6.9Hz). (DMSOd₆) |
| 2-160 | 219~220 (decomp.) | 6.67(1H, d, J=7.2Hz), 6.92-7.10(1H, m), 7.27-7.39(1H, m), 7.49-7.64(1H, m), 7.68-8.02(3H, m), 8.19-8.38(1H, m), 8.52(1H, dd, J=1.35, 7.35Hz), 9.62(1H, dd, J=1.35, 7.35Hz), 10.37(1H, d, J=7.2Hz). (DMSOd₆) |
| 2-161 | 265 (decomp.) | 6.72(1H, d, J=6.6Hz), 7.10-7.57(3H, m), 7.66-8.01(5H, m), 8.23(1H, dd, J=1.35, 7.5Hz), 8.70(1H, s), 8.91(1H, dd, J=1.35, 7.5Hz), 11.09(1H, d, J=6.6Hz), 13.82(1H, s). (DMSOd₆) |
| 2-162 | 178~179 | 6.48(1H, d, J=6.5Hz), 7.00(1H, t, J=6.5Hz), 7.00-7.20(1H, m), 8.10(1H, m)8.20-8.35(2H, m), 8.41(1H, s), 11.18(1H, d, J=6.5Hz). (DMSOd₆) |
| 2-163 | 212~213 | 3.71(3H, s), 3.97(3H, s), 6.58(1H, d, J=6.5Hz), 6.85-7.25(4H, m), 7.45-7.75(3H, m), 8.21(1H, d, J=7.5Hz), 8.40(1H, s), 8.52(1H, d, J=7.5 Hz), 11.50(1H, d, J=6.5Hz). (DMSOd₆) |
| 2-164 | amorphus triethylamine | 1.36(9H, t, J=7.5Hz), 2.65(3H, s), 3.17(6H, q, J=7.5Hz), 6.56(1H, d, J=7.8Hz), 6.92-7.18 (2H, m), 7.28-7.50(2H, m), 8.28(1H, dd, J= 1.35, 7.5Hz), 9.00(1H, dd, J=1.35, 7.5Hz), 11.44(1H, d, J=7.8Hz). (CDCl₃) |
| 2-165 | 150~152 | 2.53(3H, s), 2.69(3H, s), 6.55(1H, d, J=7.5Hz), 7.01-7.32(2H, m), 7.36-7.81(3H, m), 8.32-8.50(1H, m), 8.97(1H, dd, J=1.35, 6.6Hz), 11.19(1H, d, J=7.5Hz). (DMSOd₆+CDCl₃) |
| 2-166 | 183~186 (P-toluenesulfonate) | 2.29(3H, s), 6.00-6.39(1H, br), 6.73(1H, d, J= 7.2Hz), 7.03-7.36(5H, m), 7.40-7.62(6H, m), 7.67-7.78(1H, m), 7.85-8.01(2H, m), 8.19(1H, dd, J=1.35, 7.5Hz), 8.62(1H, s), 8.87(1H, dd, J=1.35, 7.5Hz), 11.19(1H, d, J=7.2Hz). (DMSOd₆) |
| 2-167 | 195~196 | 6.73(1H, d, J=7.5Hz), 7.03-7.33(2H, m), 7.36-7.48(1H, m), 7.65(1H, dd, J=1.35, 5.4Hz), 8.17(1H, dd, J=1.35, 7.8Hz), 8.25(1H, s), 8.78(1H, dd, J=1.35, 7.2Hz), 10.42(1H, d, J=7.5Hz). (DMSOd₆) |
| 2-168 | 253~256 | 6.55-6.75(3H, m), 7.20(1H, t, J=6.75Hz), 8.00-8.50(5H, m), 8.75-8.90(2H, m), 11.25(1H, d, J=6.0Hz). (DMSOd₆) |
| 2-169 | 196~198 | 1.15(3H, t, J=7.0Hz), 2.80(3H, s), 3.67(2H, q, J=7.0Hz), 5.74(1H, d, J=9.0Hz), 7.40-7.90 (2H, m), 7.60(1H, t, J=6.75Hz), 8.50(1H, d, J=6.75Hz), 9.60(1H, d, J=6.75Hz), 10.50(1H, d, J=9.0Hz). (DMSOd₆) |
| 2-170 | 185~187 | 2.72(3H, s), 6.52(1H, d, J=7.5Hz), 7.40-7.75(6 H, m), 8.50(1H, d, J=6.75Hz), 10.72(1H, d, J=7.5Hz) (DMSOd₆) |
| 2-171 | 222~223 | 6.75(1H, d, J=6.5Hz), 7.10-7.30(2H, m), 7.55(1 H, m), 7.65-8.80(2H, m), 7.95(1H, d, J=3.5 Hz), 8.20(1H, d, J=6.75Hz), 8.64(1H, s), 8.85 (1H, d, J=6.75Hz), 10.98(1H, d, J=6.5Hz). (DMSOd₆) |
| 2-172 | 118~120 | 5.05(2H, br), 6.54(1H, d, J=7.2Hz), 7.21-7.85(6H, m), 8.16-8.31(1H, m), 8.72-8.98(2H, m), 10.48(1H, d, J=7.2Hz). (DMSOd₆) |
| 2-173 | 178~180 (hydrochloride) | 6.78(1H, d, J=6.5Hz), 7.20(1H, t, J=6.5Hz), 7.30-7.82(7H, m), 8.10(1H, m)8.56(1H, s), 8.84(1H, m), 11.18(1H, d, J=6.5Hz). (DMSOd₆) |
| 2-174 | 188~190 (hydrochloride) | 6.73(1H, d, J=6.5Hz), 6.95(1H, t, J=6.5Hz), 7.00-7.98(8H, m), 8.20(1H, m)8.25(1H, s), 8.61(1H, m), 11.25(1H, d, J=6.5Hz). (DMSOd₆) |
| 2-175 | 158~159 | 4.00(3H, s), 6.75(1H, d, J=7.5Hz), 6.93-7.45(5H, m), 7.55(1H, m), 7.75(1H, m), 7.95-8.30(2H, m), 8.58(1H, s), 8.85(1H, d, J=6.75Hz), 11.45(1H, d, J=7.5Hz). (DMSOd₆) |
| 2-176 | 160~161 | 3.75(3H, s), 6.78(1H, d, J=7.5Hz), 6.85-7.63(7H, m), 7.72(1H, dd, J=6.0, 1.0Hz), 8.17(1H, d, J=6.75, 1.5Hz), 8.59(1H, s), 8.82(1H, dd, 6.75, 1.5Hz), 11.35(1H, d, J= 7.5Hz). (DMSOd₆) |
| 2-177 | 229~230 | 3.86(3H, s), 6.74(1H, d, J=7.5Hz), 6.90-7.25(3H, m), 7.50(1H, m), 7.72(1H, dd, J= 6.0, 1.0Hz), 7.88(2H, d, J=8.5Hz), 8.12 (1H, dd, J=6.75, 1.5Hz), 8.42(1H, s), 8.88 |

TABLE 7-continued

| Compound No. | m.p. (°C.) | NMR (δ value) |
|---|---|---|
| 2-178 | 172~173 | (1H, dd, J=6.75, 1.5Hz), 11.40(1H, d, J= 7.5Hz), (DMSOd₆) 6.78(1H, d, J=7.5Hz), 7.15–7.85(6H, m), 8.00–8.35(3H, m), 8.85(1H, s), 8.95(1H, d, J=6.75Hz), 11.25(1H, d, J=7.5Hz). (DMSOd₆) |
| 2-179 | 225~226 | 6.75(1H, d, J=7.5Hz), 7.05–7.30(2H, m), 7.40–7.60(3H, m), 7.65–8.05(3H, m), 8.18 (1H, d, J=6.75Hz), 8.65(1H, s), 8.81 (1H, d, J=6.75Hz), 11.23(1H, d, J=7.5Hz). (DMSOd₆) |
| 2-180 | 228~229 | 6.75(1H, d, J=7.5Hz), 7.00–7.30(2H, m), 7.40–7.65(2H, m), 7.77(1H, dd, J=6.0, 1.0Hz), 7.95(2H, d, J=8.5Hz), 8.15(1H, dd, J=6.75, 1.5Hz), 8.63(1H, s), 8.84(1H, dd, J=6.75, 1.5Hz), 11.35(1H, d, J=7.5Hz). (DMSOd₆) |
| 2-181 | 179~180 | 2.37(3H, s), 2.48(3H, s), 6.67(1H, d, J= 7.5Hz), 6.91–7.18(4H, m), 7.33–7.45(2H, m), 7.60(1H, d, J=9.0Hz), 7.78(1H, s), 8.28–8.40(2H, m), 11.53(1H, d, J=7.5Hz). (CDCl₃) |
| 2-182 | 193~195 | 2.30(6H, s), 6.50(1H, d, J=7.5Hz), 6.91 (1H, t, J=6.0Hz), 7.03–7.30(3H, m)7.39– 7.51(2H, m), 7.53–7.65(1H, m), 7.85(1H, s), 8.10–8.28(2H, m), 11.60(1H, d, J=7.5Hz). (CDCl₃) |
| 2-183 | 205~207 | 2.50(6H, br), 6.75(1H, d, J=8.5Hz), 7.00– 7.30(4H, m), 7.38–7.53(1H, m), 7.65–7.85 (2H, m), 8.14(1H, d, J=6.75Hz), 8.35(1H, s), 8.85(1H, d, J=6.75Hz), 11.28(1H, d, J= 8.5Hz). (DMSOd₆) |
| 2-184 | 103~104 | 1.34(9H, s), 2.50(3H, s), 6.60(1H, d, J= 8.5Hz), 6.80–7.15(2H, m), 7.20–7.45(4H, m), 7.60–7.85(2H, m), 8.18(1H, d, J= 6.75Hz), 8.30(1H, d, J=6.75Hz), 11.59(1H, d, J=8.5Hz). (CDCl₃) |
| 2-185 | 129~130 | 1.32(9H, s), 2.45(3H, s), 6.65(1H, d, J= 8.5Hz), 6.80–7.20(2H, m), 7.21–7.51(4H, m), 7.75–7.90(2H, m), 8.21(1H, d, J= 6.75Hz), 8.32(1H, d, J=6.75Hz), 11.55(1H, d, J=8.5Hz). (CDCl₃) |
| 2-186 | 159~160 | 2.35(3H, s), 6.75(1H, d, J=8.5Hz), 7.08– 7.30(3H, m), 7.38–7.56(2H, m), 7.72(1H, d, J=4.5Hz), 7.90(1H, m), 8.18(1H, d, J= 6.75Hz), 8.78(1H, s), 8.92(1H, d, J=6.75 Hz), 11.18(1H, d, J=8.5Hz). (DMSOd₆) |
| 2-187 | 184~185 | 2.40(3H, s), 6.75(1H, d, J=7.5Hz), 7.00– 7.90(8H, m), 8.18(1H, d, J=6.75Hz), 8.58 (1H, s), 8.85(1H, d, J=6.75Hz), 11.43(1H, d, J=7.5Hz). (DMSOd₆) |
| 2-188 | 218~220 | 2.35(3H, s), 6.76(1H, d, J=7.5Hz), 7.00– 7.40(4H, m), 7.54(1H, m), 7.65–7.95(3H, m), 8.13(1H, dd, J=6.75, 1.5Hz), 8.50(1H, s), 8.83(1H, d, J=6.75, 1.5Hz), 11.38(1H, d, J=7.5Hz). (DMSOd₆) |
| 2-189 | 186~188 (decomp.) | 2.67(3H, s), 6.61(1H, d, J=7.8Hz), 6.92– 7.16(2H, m), 7.33–7.67(6H, m), 7.86– 8.07(2H, m), 8.23(1H, dd, J=1.35, 6.45Hz), 8.61(1H, dd, J=1.35, 6.45Hz), 8.71(1H, s), 11.33(1H, d, J=7.8Hz). (CDCl₃) |
| 2-190 | 132~134 | 6.49(1H, d, J=7.8Hz), 6.90–7.50(10H, m), 8.10–8.30(2H, m), 10.71(1H, d, J=7.8Hz). (CDCl₃) |
| 2-191 | 155~157 | 6.71(1H, d, J=7.5Hz), 6.99–7.19(2H, m), 7.20–7.53(6H, m), 7.60(1H, dd, J=1.35, 5.1Hz), 8.13(1H, dd, J=1.35, 7.5Hz), 8.38 (1H, s), 8.88(1H, dd, J=1.35, 6.75Hz), 10.80(1H, d, J=7.5Hz). (DMSOd₆) |
| 2-194 | 235~237 | 6.75(1H, d, J=6.3Hz), 7.05–7.34(2H, m), 7.50–7.60(3H, m), 7.78–8.07(5H, m), 8.15 (1H, dd, J=1.5, 6.45Hz), 8.39–8.47(1H, m), 8.69(1H, s), 8.83(1H, dd, J=1.5, 6.45Hz), 11.38(1H, d, J=6.3Hz). (DMSOd₆) |
| 2-195 | 170~172 | 2.37(3H, s), 3.02(2H, br), 6.60(1H, d, J= 8.1Hz), 6.70–7.14(2H, m), 7.35–7.51(2H, m), 8.00–8.29(2H, m), 11.49(1H, d, J= 8.1Hz). (CDCl₃) |
| 2-196 | 187~189 | 2.20–2.45(12H, m), 6.74(1H, d, J=8.5Hz), 7.00–7.28(2H, m), 7.35(1H, s), 7.45(1H, d, J=3.0Hz), 7.63(1H, d, J=6.0Hz), 8.05– 8.28(2H, m), 8.82(1H, d, J=6.75Hz), 11.40 (1H, d, J=8.5Hz). (DMSOd₆) |
| 2-197 | 118~120 | 1.35(3H, t, J=7.0Hz), 2.76(2H, q, J=7.0Hz), 6.62(1H, d, J=7.5Hz), 6.85–7.10(2H, m), 7.35(1H, m), 7.65(1H, d, J=4.5Hz), 7.75(1 H, s), 8.98(1H, d, J=6.75, 1.5Hz), 8.62(1H, d, J=6.75Hz), 11.27(1H, d, J=7.5Hz). (DMSOd₆) |
| 2-200 | 195~196 | 1.23(3H, t, J=7.0Hz), 2.66(2H, q, J=7.0Hz), 6.71(1H, d, J=8.5Hz), 7.00–7.40(4H, m), 7.52(1H, d, J=3.0Hz), 7.60–7.90(3H, m), 8.10(1H, d, J=6.75Hz), 8.43(1H, s), 8.75 (1H, d, J=6.75Hz), 11.40(1H, d, J=8.5Hz). (DMSOd₆) |
| 2-201 | 237~238 | 6.72(1H, d, J=8.5Hz), 7.05–7.27(2H, m), 7.45– 7.95(6H, m), 8.13(1H, dd, J=6.75, 1.5Hz), 8.55(1H, s), 8.80(1H, dd, J=6.75, 1.5Hz), 11.26 (1H, d, J=8.5Hz). (DMSOd₆) |
| 2-202 | 91~94 | 1.03–1.37(6H, m), 1.47–3.00(4H, m), 6.82(1H, d, J=7.5Hz), 7.05–7.31(4H, m), 7.38–7.49(1H, m), 7.52–7.61(1H, m), 7.63–7.76(1H, m), 8.15 (1H, d, J=1.35, 7.5Hz), 8.38(1H, s), 8.88(1H, dd, J=1.35, 6.95Hz), 11.21(1H, d, J=7.5Hz). (DMSOd₆) |
| 2-203 | 189~190 | 2.54(3H, s), 6.75(1H, d, J=8.5Hz), 7.05–7.40(4 H, m), 7.48(1H, m), 7.70(1H, m), 7.93(1H, m), 8.25(1H, d, J=6.75Hz), 8.50(1H, s), 8.85(1H, d, J=6.75Hz), 11.12(1H, d, J=8.5Hz). (DMSOd₆) |
| 2-204 | 141~142 | 1.18(3H, t, J=7.8Hz), 2.44(3H, s), 2.60(2H, q, J=7.8Hz), 6.77(1H, d, J=7.2Hz), 7.02–7.30 (3H, m), 7.40–7.52(1H, m), 7.63–7.77(2H, m), 8.13(1H, dd, 1.35, 7.5Hz), 8.41(1H, s), 8.83(1H, dd, J=1.35, 6.75Hz), 11.28(1H, d, J=7.2Hz). (DMSOd₆) |
| 2-209 | 195~197 | 2.62(3H, s), 2.81(3H, s), 6.65(1H, d, J=8.5Hz), 6.90–7.50(5H, m), 7.80–8.15(3H, m), 8.42(1H, s), 8.78(1H, d, J=6.75Hz), 11.08(1H, d, J=8.5 Hz). (DMSOd₆) |
| 2-210 | 237~238 | 2.61(3H, s), 3.22(3H, s), 6.74(1H, d, J= 8.5Hz), 7.05–7.35(2H, m), 7.48(1H, m), 7.65–8.22(5H, m), 8.58(1H, s), 8.88(1H, d, J=6.75Hz), 11.18(1H, d, J=8.5Hz). (DMSOd₆) |
| 2-211 | 201~202 | 2.30(3H, s), 3.94(3H, s), 6.49(1H, d, J= 7.5Hz), 6.91(1H, t, J=7.5Hz), 7.00–7.30 (3H, m), 7.35–7.52(3H, m), 7.89(1H, d, J= 2.0Hz), 8.22(1H, s), 8.18(1H, dd, J=7.5, 1.5Hz), 8.25(1H, dd, J=7.5, 1.5Hz), 11.62 (1H, d, J=7.5Hz). (CDCl₃) |
| 2-212 | 244~245 | 4.00(3H, s), 6.50(1H, d, J=7.5Hz), 6.99– 7.35(3H, m), 7.48–7.61(2H, m), 8.05–8.25 (2H, m), 8.35(1H, s), 8.59(1H, dd, J=7.5, 1.5Hz), 11.29(1H, d, J=7.5Hz). (DMSOd₆+CDCl₃) |
| 2-213 | 138~139 | 1.10–1.40(12H, m), 2.75–3.15(1H, m), 3.55–3.90(1H, m), 6.82(1H, d, J=8.5Hz), 7.05–7.70(7H, m), 8.18(1H, d, J=6.75Hz), 8.23(1H, s), 8.89(1H, d, J=6.75Hz), 11.20 (1H, d, J=8.5Hz). (DMSOd₆) |
| 2-214 | 153~154 | 1.12–1.31(6H, m), 1.30(3H, d, J=6.0Hz), 2.70–3.18(1H, m), 3.40–3.70(1H, m), 6.67 (1H, d, J=8.5Hz), 6.90–7.20(2H, m), 7.70 (1H, s), 8.15–8.40(2H, m), 11.42(1H, d, J= 8.5Hz). (CDCl₃) |
| 2-215 | 207~209 | 1.32(3H, d, J=7.5Hz), 2.75–3.15(1H, m), 6.55(1 H, d, J=7.5Hz), 6.98(1H, t, J=6.0Hz), 7.08– 7.18(1H, m), 7.28(1H, d, J=8.5Hz), 7.35–7.55 (2H, m), 7.75(2H, d, J=8.5Hz), 7.89(1H, s), |

TABLE 7-continued

| Compound No. | m.p. (°C.) | NMR (δ value) |
|---|---|---|
| 2-230 | 215~217 | 8.20(1H, dd, J=6.0, 1.5Hz), 8.25(1H, dd, J= 6.0, 1.5Hz), 11.60(1H, d, J=7.5Hz). (CDCl₆) 2.28(3H, s), 6.40–6.75(3H, m), 7.00–7.60(5H, m), 8.30(1H, d, J=6.75Hz), 9.75(1H, d, J= 7.0Hz). (DMSOd₆) |
| 2-231 | 175~176 | 6.50(1H, d, J=7.5Hz), 7.05–7.15(1H, m), 7.35– 7.50(4H, m), 7.80–8.00(1H, m), 7.85(1H, d, J= 4.5Hz), 8.32(1H, s), 8.50(1H, d, J=4.5Hz), 11.12(1H, d, J=7.5Hz). (CDCl₃) |
| 2-232 | 209~210 | 6.48(1H, d, J=7.5Hz), 7.05–7.20(1H, m), 7.35– 7.55(4H, m), 7.75–7.95(1H, m), 7.82(1H, s), 8.38(1H, s), 10.98(1H, d, J=7.5Hz). (CDCl₃) |

Formulation Example 1

Emulsifiable concentrates, as prepared by blending the following components:

| Compound No. 2-2 | 20% (by weight) |
|---|---|
| xylene | 75% |
| polyoxyethylenealkylaryl ether (Nonipol 85$^R$) | 5% |

Formulation Example 2

Wettable powders, as prepared by blending and grinding the following components:

| Compound No. 2-24 | 50% (by weight) |
|---|---|
| diatomaceus earth | 44% |
| polyoxyethylenealkylaryl ether (Nonipol 85$^R$) | 6% |

Formulation Example 3

Powders, as prepared by blending the following mixture:

| Compound No. 2-27 | 3% (by weight) |
|---|---|
| clay | 40% |
| talc | 57% |

What we claim is:

1. A condensed heterocyclic compound of the formula:

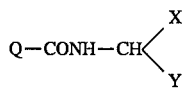

or an agriculturally acceptable salt thereof, wherein:

Q is a condensed heterocyclic group having the formula:

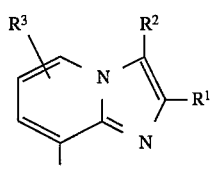

in which $R^1$ is a $C_{1-6}$ alkyl, halogen, $C_{1-4}$ alkoxy, $C_{1-4}$ alkylthio, $C_{6-10}$ aryloxy, $C_{6-10}$ arylthio, alkoxycarbonyl, phenyl, mono-, di-, tri-, or tetra-halogen-substituted phenyl, mono-, di-, tri-, or tetra-$C_{1-4}$ alkyl substituted phenyl, mono-, di-, tri-, or tetra $C_{1-4}$ alkoxy-substituted phenyl, mono-, di-, tri-, or tetra-$C_{1-4}$ alkylthio-substituted phenyl, 2-chloro-4-nitrophenyl, 4-nitrophenyl, 2-methyl-4-aminophenyl, 2-bromo-4-nitrophenyl, 2-nitro- 4-methylphenyl, pyridyl, furyl, thienyl, or thiazolyl;

$R^2$ and $R^3$ are hydrogen, $C_{1-6}$ alkyl, halogen, nitro, amino, sulfo, mono- or dialkylsulfamoyl, alkoxycarbonyl, formyl, cyano, phenyl, mono-, di-, tri-, or tetra-halogen-substituted phenyl, mono-, di-, tri-, or tetra-$C_{1-4}$ alkyl-substituted phenyl, mono-, di-, tri-, or tetra-$C_{1-4}$ alkoxy-substituted phenyl, mono-, di-, tri-, or tetra-$C_{1-4}$ alkylthio-substituted phenyl, 2-chloro-4-nitrophenyl, 4-nitrophenyl, 2-methyl-4-aminophenyl, 2-bromo-4-nitrophenyl, or 2-nitro-4-methylphenyl, or a 5 or 6 membered heterocyclic group selected from the group consisting of pyridyl, furyl, thienyl, and thiazolyl;

X is hydrogen; a group attached through a carbon atom selected from the group consisting of $C_{1-10}$ alkyl, $C_{2-4}$ alkenyl, $C_{1-10e}$ haloalkyl, $C_{3-6}$ cycloalkyl, $C_{3-6}$ cycloalkenyl, $C_{6-10}$ aryl, $C_{7-10}$ aralkyl and a heterocyclic ring of the formula:

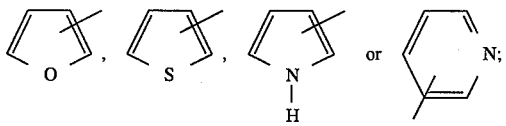

a group attached through an oxygen atom selected from the group consisting of $C_{1-10}$ alkoxy, $C_{6-10}$ aryloxy, and $C_{7-10}$ aralkyloxy; a group attached through a sulfur atom selected from the group consisting of $C_{1-10}$ alkylthio, $C_{6-10}$ arylthio, and $C_{7-10}$ aralkylthio; a group attached through a nitrogen atom selected from the group consisting of $C_{1-10}$ alkylamino, $C_{6-10}$ arylamino, $C_{7-10}$ aralkylamino, and a group of the formula:

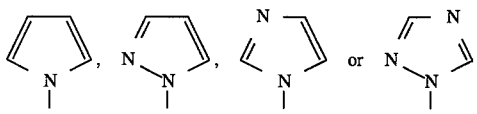

wherein each of said groups attached through a carbon atom, an oxygen atom, a sulfur atom or a nitrogen atom is unsubstituted or substituted with one to four substituents selected from the group consisting of nitro, amino, hydroxy, cyano, carboxyl, sulfonyl, halogen, $C_{1-4}$ alkoxy, $C_{1-4}$ alkylthio, phenylthio, and benzylthio; and Y is cyano, carbamoyl, thiocarbamoyl, or trichloromethyl.

2. A compound selected from the group consisting of

α-(2-phenylimidazo[1,2-a]pyridin-8-ylcarbonylamino)-(2-thienyl)acetonitrile,

α-{2-(2-methoxyphenyl)imidazo[1,2-a]pyridin-8-ylcarbonylamino}-( 2-thienyl)acetonitrile, α-{2-(3-methoxyphenyl)imidazo[1,2-a]pyridin-8-ylcarbonylamino}-( 2-thienyl)acetonitrile, α-{2-(2,4-dimethoxyphenyl)imidazo[1,2-a]pyridin-8-ylcarbonylamino}-( 2-thienyl)acetonitrile, α-{2-(2,4-di isopropylphenyl)imidazo[1,2-a]pyridin-8-ylcarbonylamino}-( 2-thienyl)acetonitrile, α-{2-(3-trifluoromethylphenyl)imidazo[1,2-a]pyridin-8ylcarbonylamino}-( 2-thienyl)acetonitrile, or an agriculturally acceptable salt thereof.

3. A condensed heterocyclic compound of the formula:

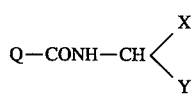

or an agriculturally acceptable salt thereof, wherein:

Q is a condensed heterocyclic group having the formula:

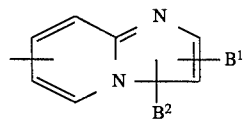

in which the substituents $B^1$ and $B^2$ on the condensed heterocyclic group Q may be the same or different from each other, and are hydrogen, nitro, amino, hydroxyl, cyano, $C_{1-3}$ acyl, carbamoyl, carboxyl, $C_{1-4}$ alkoxycarbonyl, sulfo, halogen, $C_{1-4}$ alkoxy, $C_{6-10}$ aryloxy, $C_{6-10}$ arylthio, $C_{7-10}$ aralkylthio, mono-, di-, tri-, or tetra-halogen-substituted phenyl, mono-, di-, tri-, or tetra $C_{1-4}$ alkyl-substituted phenyl, mono-, di-, tri-, or tetra-$C_{1-4}$ alkylthio-substituted phenyl, 2-chloro-4-nitrophenyl, 4-nitrophenyl, 2-methyl-4-aminophenyl, 2-bromo-4-nitrophenyl, 2-nitro- 4-methylphenyl, pyridyl, furyl, thienyl, or thiazolyl;

X is hydrogen; a group attached through a carbon atom selected from the group consisting of $C_{1-10}$ alkyl, $C_{2-4}$ alkenyl, $C_{1-10}$ haloalkyl, $C_{3-6}$ cycloalkyl, $C_{3-6}$ cycloalkenyl, $C_{6-10}$ aryl, $C_{7-10}$ aralkyl and a heterocyclic ring of the formula:

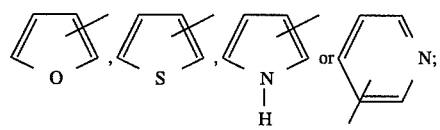

a group attached through an oxygen atom selected from the group consisting of $C_{1-10}$ alkoxy, $C_{6-10}$ aryloxy, and $C_{7-10}$ aralkyloxy; a group attached through a sulfur atom selected from the group consisting of 2-(4-sulfophenyl)imidazo[1,2-a]pyridine-8-carboxylic acid, $C_{1-10}$ alkylthio, $C_{6-10}$ arylthio, and $C_{7-10}$ aralkylthio; a group attached through a nitrogen atom selected from the group consisting of $C_{1-10}$ alkylamino, $C_{6-10}$ arylamino, $C_{7-10}$ aralkylamino, and a group of the formula:

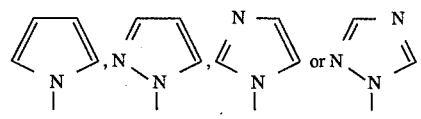

wherein each of said groups attached through a carbon atom, an oxygen atom, a sulfur atom or a nitrogen atom is unsubstituted or substituted with one to four substituents selected from the group consisting of nitro, amino, hydroxy, cyano, carboxyl, sulfonyl, halogen, $C_{1-4}$ alkoxy, $C_{1-4}$ alkylthio, phenylthio, and benzylthio; and Y is cyano, carbamoyl, thiocarbamoyl, or trichloromethyl.

4. A compound selected from the group consisting of methyl imidazo[1,2-a]pyridine-8-carboxylate, imidazo[1,2-a]pyridine-8-carboxylic acid, ethyl 3-chloroimidazo[1,2-a]pyridine-8-carboxylate, 3-chloroimidazo[1,2-a]pyridine-8-carboxylic acid, methyl 3-dimethylaminomethyl-2-methylimidazo[1,2-a]pyridine-8-carboxylate, 3-dimethylaminomethyl-2-methylimidazo[1,2-a]pyridine-8-carboxylic acid, 3-cyanoethyl-2-methylimidazo[1,2-a]pyridine-8-carboxylic acid, ethyl 3-chlorosulfonyl-2-methylimidazo[1,2-a]pyridine-8-carboxylate, ethyl 3-ethoxycarbonyl-2-hydroxyimidazo[1,2-a]pyridine-8-carboxylate, 2-chloroimidazo[1,2-a]pyridine-3,8-dicarboxylic acid, 3-benzylideneamino-2-methylimidazo[1,2-a]pyridine-8-carboxylic acid, or an agriculturally acceptable salt thereof.

5. A compound selected from the group consisting of

α-(imidazo[1,2-a]pyridin-8-ylcarbonylamino)-(2-furyl)acetonitrile,

α-(3-chloroimidazo[1,2-a]pyridin-8-ylcarbonylamino)-(2-furyl)acetonitrile,

α-(3-dimethylaminomethyl-2-methylimidazo[1,2-a]pyridin-8-ylcarbonylamino)-( 2-furyl)acetonitrile, α-(3-(1,1,2,2-tetrafluoroethyl)-2-methylimidazo[1,2-a]pyridin-8-ylcarbonylamino)-(2-furyl)acetonitrile, α-(3-dimethylaminomethyl-2-methylimidazo[1,2-a]pyridin-8-ylcarbonylamino)-( 2-thienyl)acetonitrile, α-(3-dimethylaminomethyl-2-methylimidazo[1,2-a]pyridin-8-ylcarbonylamino)- 3-fluorophenyl)acetonitrile, α-(3-dimethylaminomethyl-2-methylimidazo[1,2-a]pyridin-8-ylcarbonylamino)- 3-fluorophenyl)acetonitrile hydrochloride, α-(3-morpholinomethyl-2-methylimidazo[1,2-a]pyridin-8-ylcarbonylamino)-( 2-furyl)acetonitrile, α-(3-isopropylthiomethyl-2-methylimidazo[1,2-a]pyridin-8-ylcarbonylamino)-( 3-fluorophenyl)acetonitrile, α-(3-cyanoethyl-2-methylimidazo[1,2-a]pyridin-8-ylcarbonylamino)-( 3-fluorophenyl)acetonitrile, α-(3-(2-methyl-1-propenyl)-2-methylimidazo[1,2-a]pyridin-8-ylcarbonylamino)-( 3-fluorophenyl)acetonitrile, α-(3-dimethylaminomethyl-2-phenylimidazo[1,2-a]pyridin-8-ylcarbonylamino-( 3-fluorophenyl)acetonitrile, α-(3-dimethylaminomethyl-2-phenylimidazo[1,2-a]pyridin-8-ylcarbonylamino)-( 2-thienyl)acetonitrile, α-(3-dimethylaminomethyl-2-phenylimidazo[1,2-a]pyridin-8-ylcarbonylamino)-( 3-fluorophenyl)acetonitrile, α-(3-dimethylaminomethyl-2-phenylimidazo[1,2-a]pyridin-8-ylcarbonylamino)-( 3-fluorophenyl)acetonitrile oxalate, α-(3-(1,1,2,2-tetrafluoroethyl)-2-phenylimidazo[1,2-a]pyridin-8-ylcarbonylamino)-( 2-furyl)acetonitrile, α-(3-cyanoethyl-2-phenylimidazo[1,2-a]pyridin-8-ylcarbonylamino)- 2-furyl)acetonitrile, α-(3-(2-methyl-1-propenyl)-2-phenylimidazo[1,2-a]pyridin-8-ylcarbonylamino)-( 2-furyl) acetonitrile, α-(3-(2,2,2-trichloro-1-hydroxyethyl)-2-phenylimidazo [1,2-pyridin- 8-ylcarbonylamino)-(2-furyl)acetonitrile, α-(2-benzylimidazo[1,2-a]pyridin-8-ylcarbonylamino)-(2-furyl)acetonitrile, α-(2-trifluoromethylimidazo[1,2-a]pyridin-8-ylcarbonylamino)-(2-furyl)acetonitrile, α-(2-formylimidazo[1,2-a]pyridin-8-ylcarbonylamino)-(2-thienyl)acetonitrile, α-(2-cyanoimidazo[1,2-a]pyridin-8-ylcarbonylamino)-(2-thienyl)acetonitrile, α-(2-(2-methyl-1-propenyl)imidazo[1,2-a]pyridin-8-ylcarbonylamino)-( 2-thienyl)acetonitrile, α-(2-ethoxyiminomethylimidazo[1,2-a]pyridin-8-ylcarbonylamino)-(2-thienyl)acetonitrile, α-(3-methoxyimidazo[1,2-a]pyridin-8-ylcarbonylamino)-(2-furyl)acetonitrile, α-3-dimethylaminomethyl-2,5-dimethyl imidazo[1,2-a]pyridin-8-ylcarbonylamino)-(3-fluorophenyl)acetonitrile, α-5,7-di (trifluoromethyl)-2-phenylimidazo[1,2-a]pyridin-8-ylcarbonylamino)-(2-furyl)acetonitrile, α-2-phenoxymethylimidazo[1,2-a]pyridin-8-ylcarbonylamino)-(3-fluorophenyl)acetonitrile, α-2-phenylthiomethylimidazo[1,2-a]pyridin-8-ylcarbonylamino)-(3-fluorophenyl)acetonitrile, α-2-phenylsulfinylmethylimidazo[1,2-a]pyridin-8-ylcarbonylamino)-( 3-fluorophenyl)acetonitrile, α-2-phenylsulfonylmethylimidazo[1,2-a]pyridin-8-ylcarbonylamino)-( 3-fluorophenyl)acetonitrile, α-3-dimethylaminomethyl-2-phenoxymethylimidazo[1,2-a]pyridin-8-ylcarbonylamino)-( 3-fluorophenyl)acetonitrile, α-2-methoxymethylimidazo[1,2-a]pyridin-8-ylcarbonylamino)-(2-furyl)acetonitrile, α-3-morpholinomethyl-2-methoxymethylimidazo[1,2-a]pyridin-8-ylcarbonylamino)-( 2-furyl)acetonitrile, α-2-methylthiomethylimidazo[1,2-a]pyridin-8-ylcarbonylamino)-(2-furyl)acetonitrile, α-(2-methylsulfinylmethylimidazo[1,2-a]pyridin-8-ylcarbonylamino)-( 2-furyl)acetonitrile, α-(3-dimethylaminomethyl-2-methylthiomethylimidazo[1,2-a]pyridin-8-ylcarbonylamino)-( 2-furyl)acetonitrile, α-(2-methylsulfonylmethylimidazo[1,2-a]pyridin-8-ylcarbonylamino)-( 3-fluorophenyl)acetonitrile, α-(2-morpholinomethylimidazo[1,2-a]pyridin-8-ylcarbonylamino)-( 3-fluorophenyl)acetonitrile, α-(diethoxyphosphoxylmethylimidazo[1,2-a]pyridin-8-ylcarbonylamino)-( 3-fluorophenyl)acetonitrile, α-(2-dimethylaminodithiocarbonylmethylimidazo[1,2-a]pyridin-8-ylcarbonylamino)-( 2-furyl)acetonitrile, α-(2-chloromethylimidazo[1,2-a]pyridin-8-ylcarbonylamino)-(2-furyl)acetonitrile, α-(3-phenylcarbamoyl-2-trifluoromethylimidazo[1,2-a]pyridin-8-ylcarbonylamino)-( 3-fluorophenyl) acetonitrile, α-(3-benzoylimidazo[1,2-a]pyridin-8-ylcarbonylamino)-(2-thienyl)acetonitrile, α-(3-(1-hydroxyphenylmethyl)imidazo[1,2-a]pyridin-8-ylcarbonylamino)-( 2-thienyl)acetonitrile, α-(3-benzylimidazo[1,2-a]pyridin-8-ylcarbonylamino)-(2-thienyl)acetonitrile, α-(3-ethylimidazo[1,2-a]pyridin-8-ylcarbonylamino)-(2-thienyl)acetonitrile, α-(3-sulfomethyl-2-phenylimidazo[1,2-a]pyridin-8-ylcarbonylamino)-( 2-thienyl)acetonitrile, α-(2-(4-dimethylaminophenyl)imidazo[1,2-a]pyridin-8-ylcarbonylamino)-( 2-thienyl)acetonitrile, α-(3-benzylidenamino-2-phenylimidazo[1,2-a]pyridin-8-ylcarbonylamino)-(2-thienyl)acetonitrile, α-(2-biphenylylimidazo[1,2-a]pyridin-8-ylcarbonylamino)-(2-thienyl)acetonitrile, α-(3-nitroimidazo[1,2-a]pyridin-8-ylcarbonyl-amino)-(2-thienyl)acetonitrile, α-(3-(4-sulfophenyl)imidazo[1,2-a]pyridin-8-ylcarbonylamino)-(2-thienyl)acetonitrile, α-(2-trifluoroimidazo[1,2-a] pyridin-8-ylcarbonylamino)-(3-fluorophenyl)acetamide, α-(2-(3-hydroxyphenyl)imidazo[1,2-a]pyridin-8-ylcarbonylamino)-(2-thienyl)acetonitrile, α-(2-(2-hydroxyphenyl)imidazo[1,2-a]pyridin-8-ylcarbonylamino)-(2-thienyl)acetonitrile, α-(3-benzylidenamino-2-methylimidazo[1,2-a]pyridin-8-ylcarbonylamino)-( 2-thienyl)acetonitrile, α-(2-phenyl-5-hydroxy-6-chloroimidazo[1,2-a]pyridin-8-ylcarbonylamino)-( 2-thienyl)acetonitrile, α-(2-(β-naphthyl)imidazo[1,2-a]pyridin-8-ylcarbonylamino)-(2-thienyl)acetonitrile, α-(2-(2-dimethylcarbamoylphenyl(imidazo[1,2-a]pyridin-8-ylcarbonylamino)-( 2-thienyl]acetonitrile, α-(2-(2-methoxymethylphenyl)imidazo[1,2-a]pyridin-8-ylcarbonylamino)-( 2-thienyl)acetonitrile, α-(2-(2-methyl-4-methylsulfinylphenyl)imidazo[1,2-a]pyridin-8-ylcarbonylamino)-( 2-thienyl)acetonitrile, α-(2-(2-methyl-4-sulfonylphenyl)imidazo[1,2-a]pyridin-8-ylcarbonylamino)-( 2-thienyl)acetonitrile, α-(2-hexylimidazo[1,2-a]pyridin-8-ylcarbonylamino)-(2-thienyl)acetonitrile, α-2-(4-cyanophenyl)imidazo[1,2-a]pyridin-8-ylcarbonylamino)-(2-thienyl)acetonitrile, α-2-(2-trifluoromethyl)imidazo[1,2-a]pyridin-8-ylcarbonylamino)-( 2-thienyl)acetonitrile, α-(2-(3-trifluoromethylphenyl)imidazo[1,2-a]pyridin-8-ylcarbonylamino)-( 2-thienyl)acetonitrile and α-2-(5-trifluoromethyl-2-methylphenyl)imidazo[1,2-a]pyridin-8-ylcarbonylamino)-( 2-thienyl)acetonitrile or an agriculturally acceptable salt thereof.

6. A compound of claim 1 wherein Q is

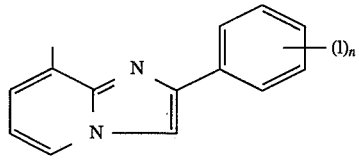

wherein n is 0, 1, 2, 3, or 4 and 1 is the same or different $C_{1-4}$ alkyl, $C_{1-4}$ alkoxy, $C_{1-4}$ alkylthio or halogen.

7. A method for controlling plant blight comprising applying to a plant a fungicidally effective amount of a compound of claim 1 or an agriculturally acceptable salt thereof.

* * * * *